(12) United States Patent
Ghosh

(10) Patent No.: US 12,405,269 B2
(45) Date of Patent: Sep. 2, 2025

(54) BIOSENSORS FOR MEASURING METASTATIC POTENTIAL AND CHEMORESISTANCE OF SINGLE CANCER CELLS

(71) Applicant: The Regents of the University of California, Oakland, CA (US)

(72) Inventor: Pradipta Ghosh, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1076 days.

(21) Appl. No.: 17/051,293

(22) PCT Filed: May 13, 2019

(86) PCT No.: PCT/US2019/031954
§ 371 (c)(1),
(2) Date: Oct. 28, 2020

(87) PCT Pub. No.: WO2019/222071
PCT Pub. Date: Nov. 21, 2019

(65) Prior Publication Data
US 2021/0239686 A1      Aug. 5, 2021

Related U.S. Application Data

(60) Provisional application No. 62/670,905, filed on May 14, 2018.

(51) Int. Cl.
*G01N 33/542*      (2006.01)
*G01N 33/574*      (2006.01)

(52) U.S. Cl.
CPC ..... *G01N 33/542* (2013.01); *G01N 33/57496* (2013.01)

(58) Field of Classification Search
CPC ........... G01N 33/542; G01N 33/57496; G01N 2800/52; G01N 2800/56; G01N 33/574
See application file for complete search history.

(56) References Cited

U.S. PATENT DOCUMENTS

2014/0234872 A1* 8/2014 Ghosh ................... C07K 16/18
                                                          435/7.1
2018/0104307 A1   4/2018 Ghosh

FOREIGN PATENT DOCUMENTS

WO      2013/016465 A1    1/2013
WO      2018/156697 A1    8/2018

OTHER PUBLICATIONS

Midde, KK et. al. "Multimodular biosensors reveal a novel platform for activation of G proteins by growth factor receptors", 2015, PNAS, 112(9), E937-E946. (Year: 2015).*
Lin, C et. al. "Tyrosine Phosphorylation of the Gα-Interacting Protein GIV Promotes Activation of Phosphoinositide 3-Kinase During Cell Migration", 2011, Cell Biology, 4(192), 1-14. (Year: 2011).*
Hirata, E and Kiyokawa, E, "Future Perspective of Single-Molecule FRET Biosensors and Intravital FRET Microscopy", 2016, Biophysical Journal, 111, 1103-1111. (Year: 2016).*
PCT International Search Report and Written Opinion for PCT Application No. PCT/US2019/031954 mailed Jul. 30, 2019 (10 pages).
Getz et al., "A Predictive Computational Model Reveals that GIV/Girdin Serves as a Tunable Valve for EGFR-Stimulated Cyclic AMP Signals," Molecular Biology of the Cell, 2019, 30(13):1-2.
Midde et al., "Single-Cell Imaging of Metastatic Potential of Cancer Cells," iScience, 2018, 10:53-65 with Supplemental Information (34 pages).

* cited by examiner

*Primary Examiner* — Nelson B Moseley, II
*Assistant Examiner* — Alyssa Rae Stonebraker
(74) *Attorney, Agent, or Firm* — Eversheds-Sutherland (US) LLP

(57) ABSTRACT

The present invention provides a Fluorescence Resonance Energy Transfer (FRET) biosensor that measures the metastatic potential and/or chemoresistance of single living cancer cells, and/or cells associated with fibrogenesis, diabetes, aging, and/or infertility.

6 Claims, 55 Drawing Sheets
Specification includes a Sequence Listing.

IMP-Y1764

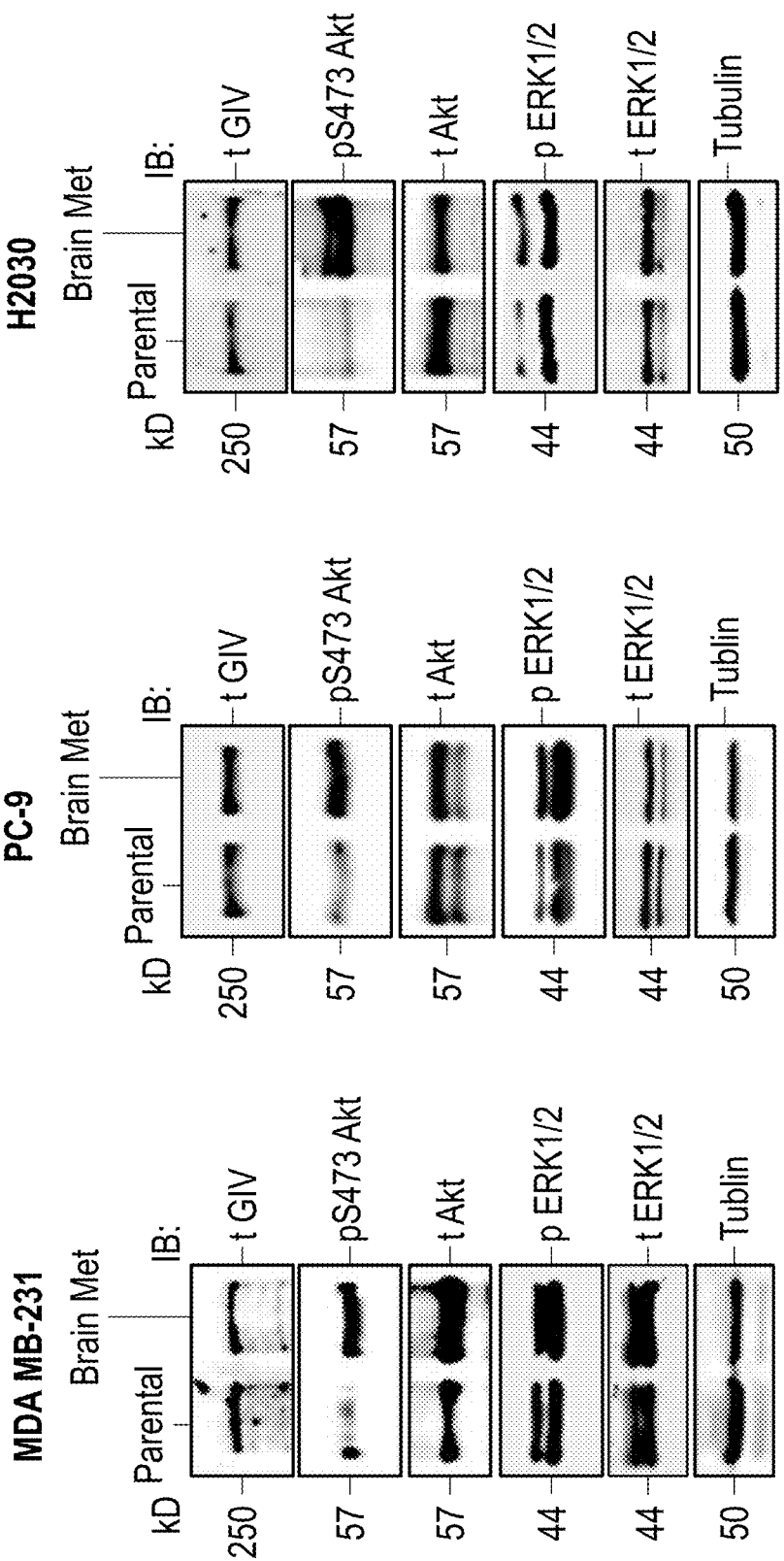

| Schematic of GIV Substrates | Probe Name |
|---|---|
| Y1764 — GIV Peptide | IMP-Y1764 |
| F1764 — GIV Peptide | IMP-Y1764F |
| Y1798 — GIV Peptide | IMP-Y1798 |
| F1798 — GIV Peptide | IMP-Y1798F |
| 1714 — GIV SH2-Like (Y1764, Y1798) — 1815 | IMP-GIV-SH2 |
| 1714 — GIV SH2-Like (F1764, F1798) — 1815 | IMP-GIV-SH2-2YF |
| 1660 — GIV-CT (F1685, Y1764, Y1798) — 1870 | IMP-GIV-CT |
| 1660 — GIV-CT (F1685, F1764, F1798) — 1870 | IMP-GIV-CT-2YF |
| 1660 — GIV-CT (A1685, F1764, F1798) — 1870 | IMP-GIV-CT-2YF/FA |

FIG. 5B

| Paired Cell Lines | Type of Cancer | Pathways Upregulated During drug Resistance | Known Genetic Abnormalities | Ref PMID (Source Lab) |
|---|---|---|---|---|
| MDAMB231 (Parental and Brain Metastatic Clone) | Human Breast Adenocarcinoma | Metastatic Pleural Effusion | KRAS G13D BRAFG464V PMID:17314276 | 24581498 (J.Massague) |
| PC-9 (Parental and Brain Metastatic Clone) | Human Lung Adenocarcinoma | Metastatic Clone from lymph node | KRAS (G12C) PMID:880692 | 19576624 24581498 (J.Massague) |
| H230 (Parental and Brain Metastatic Clone) | Human Lung Adenocarcinoma | Metastatic Clone from lymph node | EGFRΔexon19 PMID: 15761868, PMID: 1847845 | 19576624 24581498 (J. Massague) |
| 21T (16N, NT, MT2) | Human Breast Infiltrating and Intraductal Mammary Carcinoma (ER-/PR; Node +) PMID: 1977518 | 16N = Normal, Contralateral Breast<br>NT = Primary Tumor<br>Mt2 = Metastatic Pleural Effusion | In NT and Mt2 - p53 (frameshift mutation, loss of function (PMID: 7923592) | 20198662 20458274 17545609 (A. Pardee) |

FIG. 6B

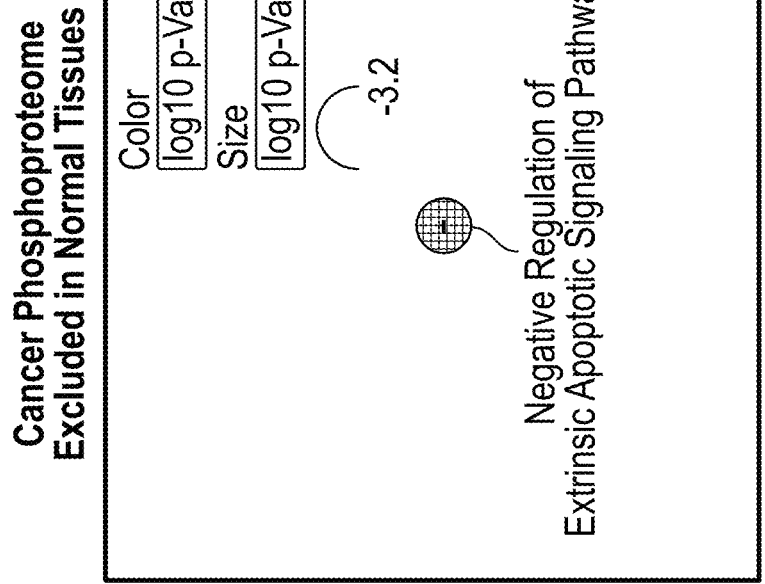
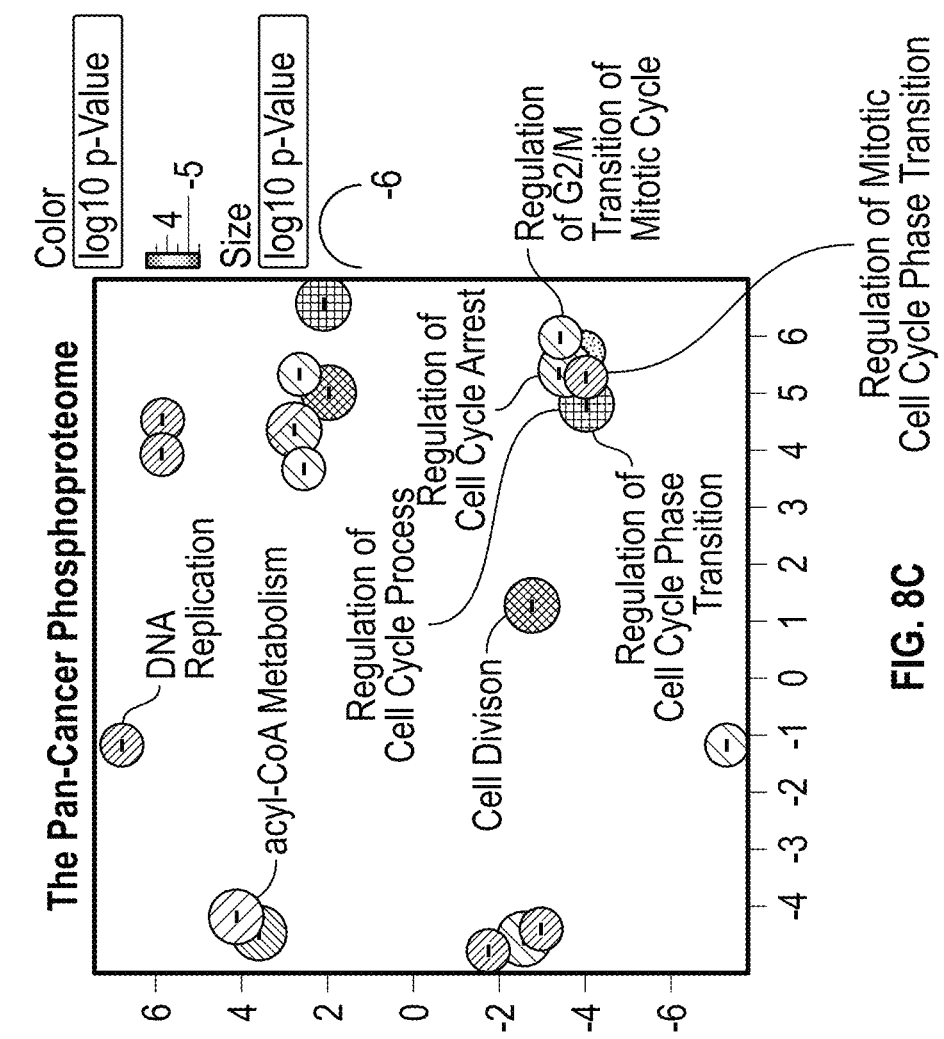
FIG. 8D
FIG. 8C

| Paired Cell Lines | Type of Cancer | Pathways Upregulated During Drug Resistance | Known Genetic Abnormalities | Ref PMID (Source Lab) |
|---|---|---|---|---|
| Hs578T (Docetaxel Sensitive vs Resistant) | Human Breast | Multiple Pathways, Including mTOR and TNF-Dependent NF-kB Survival Pathways | ER -ve: Hypotriploid Human Cell Line with a Modal Chromosome Number of 59 (ATCC.org) (PMID: 864756) | ATCC |
| HCC827 (Erlotinib Sensitive vs Resistant) | Human Lung Adenocarcinoma | PI3K (PMID: 21220474) Non-RTK Signaling (Src/FAK) (PMID:25193862; 19804422) Gowth Factor RTK Signaling (cMet, VEGF, IGFR) (PMID:24828661; 22133747; 21062933; 19921194; 19447865) STAT3 (PMID: 23894143) mTOR (PMID: 23690929) | EGFR Tyrosine Kinase Domain (E746 - A750 Deletion) (ATCC.org) | Frank Furnari (UCSD) |
| HCC827 (Lapatinib Sensitive vs Resistant) | Human Lung Adenocarcinoma | -- | EGFR Tyrosine Kinase Domain (E746 - A750 Deletion) (ATCC.org) | David Cheresh (PMID: 24747441) |

FIG. 15A

BIOSENSORS FOR MEASURING METASTATIC POTENTIAL AND CHEMORESISTANCE OF SINGLE CANCER CELLS

CROSS REFERENCE TO RELATED APPLICATIONS

This application claims the priority benefit of PCT/US2019/031954 filed on May 13, 2019 which claims the priority benefit of U.S. Provisional Application No. 62/670,905, filed May 14, 2018, the entire contents of which are incorporated herein by reference.

STATEMENT OF GOVERNMENT INTEREST

The invention was made with support under CA160911 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 11, 2025, is named 24978-0587_SL.txt and is 912 bytes in size.

BACKGROUND

Metastasis is dissemination of highly invasive cancer cells from the primary tumor to distant vital organs and the principal cause of cancer-related deaths (1). However, not all tumors are metastatic and determining the metastatic proclivity of single tumor cells remains a major challenge due to several reasons. First, and arguably the biggest hurdle is tumor molecular heterogeneity because finding the few cells (0.02% (1)) which have the potential to metastasize, interspersed within a mass of tumor cells that will not metastasize requires precise tools that can pick up a few 'signals' amid the thunderous 'noise'. Second, the understanding of what imparts metastatic potential remains incomplete despite increased comprehension of a more detailed signaling network with central control nodes (1), and biomarkers which can detect such potential across different carcinomas are still lacking. Third, the genome of the cancer cell is rewired and signaling networks are reprogrammed during this process of metastatic progression, either to adapt to the changing tumor microenvironment or to overcome the cytotoxicity of drugs (2), and biomarkers/tools that monitor any given pathway may lose significance due to the changing/evolving tumor dependency from that pathway to unknown pathway(s) (the so-called 'addiction switch') (3). Consequently, pathway-specific biomarkers that monitor the 'known' in the setting of the so-called 'unknown-unknowns' of tumor biology introduce bias in the short run and prove ineffective in the long run. Last, but not least, single-cell studies have shown that when stochastic, invasive and proliferative events are triggered by perturbations (e.g., mechanical or chemical signals), each individual cell adapts on their own, i.e., cancer cells go solo (4-13). Hence, any effective biomarker/assay must be sensitive enough to detect the plasticity of metastatic programming within a few sparsely distributed tumorigenic cells, i.e., cells that can metastasize and initiate new tumors at distant sites, within a large population of non-tumorigenic cells.

Despite these shortfalls, experts agree that estimating metastatic potential is a problem that only molecular imaging can resolve, rather than conventional techniques, e.g., IHC (14). So far, improved imaging platforms have helped detect established metastases (15) and assessed tumor cell properties as surrogate markers of metastatic potential [e.g., glucose consumption, hypoxia, angiogenesis, integrin expression patterns, or MMP activities; reviewed in (14)] and even visualize the metastatic process in real-time in vivo (16). However, single cell-based assays to measure the dynamic pro-metastatic signaling programs that contribute to the potential for metastasis remain elusive. This is largely because conventional approaches (immunofluorescence and IHC) employed to study most biomarkers on fixed tissues are fraught with technical limitations (17, 18). Even when live cells or tissue are used in the above approaches, one serious flaw remains, i.e., the loss of vital information pertinent to individual cells due to averaging over an ensemble of readouts (19). The concept of single-cell studies has gained traction in the fields of metabolomics (20), signal transduction (21, 22) and among cell biologists who seek to explore how cellular processes are organized and regulated in vivo (23), but has not been applied to study metastatic potential.

Molecular imaging of metastatic potential remains a challenge, thus, there is a need for methods to measure metastatic potential and chemoresistance of single cancer cells.

SUMMARY OF THE INVENTION

In embodiments, the present invention provides a method and system for measuring metastatic potential in single living cancer cells.

In embodiments, the present invention provides a Fluorescence Resonance Energy Transfer (FRET) biosensor that measures the metastatic potential of single living cancer cells.

In other embodiments, the present invention provides a FRET biosensor that measure the metastatic potential of single living cells associated with fibrogenesis, diabetes, aging, and/or infertility.

In embodiments, the present invention provides a FRET biosensor that accounts for the unknown-unknowns of an evolving tumor biology and eliminates the averaging-losses associated with conventional molecular imaging.

The present invention provides compositions and method for analysis of the pan-cancer phosphoproteome to identify actin-remodelers required for cell migration, that are enriched in cancers, but excluded in normal cells. In exemplary embodiments, the invention provides for the identification of the phosphoprotein, tyr-phosphorylated CCDC88A (GIV/Girdin), a metastasis-related protein, across a variety of solid tumors. The invention provides in embodiments, multi-modular biosensors that are partly derived from GIV. GIV integrates pro-metastatic signaling by multiple oncogenic receptors, and the biosensors are termed Integrator-of-Metastatic-Potential (IMP). IMPs captured the heterogeneity of metastatic potential within tissues such as primary lung and breast tumors at steady-state, detected those few cells which have acquired the highest metastatic potential and tracked their enrichment during metastasis.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIG. 1A depicts the pan-cancer phosphoproteome. FIG. 1B depicts the Phosphoproteomic map of GIV/Girdin. Tyrosine-phosphorylated peptides are most frequently detected by HTP MS studies. While tyrosines 1764 and 1798 are known to bind and activate PI3K, the role of Y1743 remains unknown. FIG. 1C depicts a schematic illustrating the modular makeup of IMP probes. A previously validated (53) nuclear export signal (NES) was incorporated to maintain most of the probe in the cytosolic compartment. FIG. 1D depicts immunoblots showing expression and ligand-induced phosphorylation of various IMP probes in Cos7 cells after EGF stimulation. FIG. 1E depicts immunoblots showing the phosphorylation status of WT IMP-Y1764 and Y1798 and their corresponding YF mutants after EGF stimulation. FIG. 1F depicts serum-starved Cos7 cells expressing IMP-Y1764 were stimulated with various growth factors prior to lysis. Lysates were immunoprecipitated with anti-GFP mAb and tyrosine phosphorylation of IMP was analyzed by immunoblotting (IB). FIGS. 1G and 1H depict lysates of Cos7 cells co-expressing IMP-Y1798 and wild-type (WT) or kinase-dead (KD) Src-HA (g) or FAH-HA (h) were immunoprecipitated and analyzed for tyrosine phosphorylation of IMP as in FIG. 1F. FIG. 1I depicts lysates of Cos7 cells expressing IMP-Y1764 or Y1798 and stimulated with Lysophosphatidic acid (LPA) were immunoprecipitated and analyzed for tyrosine phosphorylation of IMP as in FIG. 1F. FIG. 1J depicts lysates of Cos7 cells expressing IMP-Y1764 and wild-type (WT) or catalytically dead (CD) SHP1-HA were immunoprecipitated and analyzed for tyrosine phosphorylation of IMP as in FIG. 1F. FIG. 1K depicts whole cell lysates of Cos7 cells expressing various IMP probes were analyzed for phospho(p) and total(t) Akt and ERK, tubulin and GFP(IMPs) by immunoblotting (IB).

FIG. 2A depicts serum starved Cos7 cells expressing Akt-PH-YFP (pseudocolored green) were stimulated with EGF, fixed and stained for tyrosine phosphorylated GIV (anti-pY1764GIV; red) and analyzed by confocal microscopy. FIG. 2B depicts serum starved Cos7 cells expressing IMP-Y1764 or Y1798, or their corresponding YF mutants were stimulated with EGF and analyzed by confocal live-cell FRET imaging. Representative freeze-frame images from movies (SM1-4) are shown. FIG. 2C depicts time traces display the dynamic changes in FRET efficiency in b; 12-15 cells were analyzed in 3 independent assays. FIG. 2D depicts serum starved Cos7 cells expressing IMP-Y1764 or the YF mutant were stimulated with LPA and analyzed by confocal live-cell FRET imaging. Representative freeze-frame images from movies (SM5, 6) are shown. FIG. 2E depicts time traces display the dynamic changes in FRET efficiency in 12-15 cells that were analyzed in 3 independent assays. FIG. 2F depicts immunoblots showing the contribution of serum (10%) on the phosphorylation status of WT-IMP-1764 and WT-IMP-1798 probes expressed in Cos7 cells at a steady state. Phosphorylation of the IMP peptides and Akt was exclusively observed in fed state (10% FBS) but not in starved (0% FBS) conditions. FIG. 2G depicts representative steady-state FRET images of Cos7 cells expressing IMP-1764 probe and its phosphorylation triggered by 10% serum. Higher FRET efficiency signals were detected in cells with 10% serum but not in cells without serum. FIG. 2H depicts scatter plots comparing the FRET efficiency at the PM in FIG. 2G. Results are expressed as mean±S.D. FIG. 2I depicts lysates of control and GIV-depleted MDA-MB-231 cells were analyzed for GIV depletion by immunoblotting. Depletion estimated as ~85% by band densitometry. FIG. 2J depicts representative steady-state FRET images of MDA-MB-231 cells in FIG. 2I expressing the IMP-1764 probe. FIG. 2K depicts scatter plots comparing the FRET efficiency at the PM in FIG. 2J. Results are expressed as mean±S.D.

FIGS. 3A-3I provide a steady-state FRET imaging using IMP-Y1764 in isogenic cancer cells with variable metastatic potentials: FIGS. 3A-3C depict lysates of parental MDA-MB-231 (FIG. 3A), PC-9 (FIG. 3B) and H2030 (FIG. 3C) cancer cells and their brain metastatic (met) counterparts were analyzed for phospho(p) and total(t) Akt, ERK, tubulin and GIV by immunoblotting (IB). FIGS. 3D-3F depict parental and brain metastatic clones of MDA-MB-231 (FIG. 3D), PC-9 (FIG. 3E) and H2030 (FIG. 3F) cells expressing IMP-Y1764 were analyzed for steady-state FRET by confocal live-cell imaging. Representative FRET images (left) and scatter plots (right) comparing the FRET efficiency in parental vs brain met clones are displayed. FIG. 3G depicts Gaussian fits of composite histograms comparing F.E in parental (blue) vs brain metastatic (met; red) clones of cancer cells in d-f are displayed. FIG. 3H depicts a schematic summarizing the clinical course of patient #21, the source of 21T series of normal(NT-ci), primary(PT-ci) and metastatic(MT-1) breast cancer cells (50). FIG. 3I depicts graphs displaying the average FRET efficiency (left Y axis) and invasive properties (right Y axis; (54) of the 21T cell lines.

FIGS. 4A-4C depict lysates of Hs578T (FIG. 4A) and HCC827 (FIGS. 4B-4C) cancer cells, sensitive or resistant to docetaxel (DTX), Lapatinib (Lap) or Erlotinib were analyzed by immunoblotting (IB). FIGS. 4D-4F depict sensitive and resistant Hs578T (FIG. 4D) and HCC827 (FIGS. 4E-4F) cancer cells expressing IMP-Y1764 were analyzed for steady-state FRET by confocal live-cell imaging. Representative FRET images and scatter plots comparing the F.E in sensitive vs resistant cells is shown. FIGS. 4G-4H depict a summary of findings. Schematic [FIG. 4G; modified and adapted from (55)] showing that few tumorigenic cells are chemoresistant and account for tumor recurrence and metastasis, whereas most tumor cells are non-tumorigenic and are typically sensitive to chemotherapy. Schematic in FIG. 4H summarizes how single-cell FRET-based imaging with IMPs can detect those few cells with tumorigenic potential within the primary tumor (blue; right peak within the bimodal distribution) that are enriched later during the process of metastasis (single red peak).

FIGS. 5A-5B provide a rationale for the modular design of IMP probes. FIG. 5A depicts previously validated (3) structural basis for activation of PI3K by GIV is displayed. Phosphotyrosines 1764 and 1798 on GIV directly bind p85α (SH2-domains) and activate Class 1 PI3Ks. FIG. 5B depicts various GIV-derived IMPs generated and tested in this work; they either contain the two short stretches of sequence flanking either tyrosine 1764 or 1798 alone, or together (entire SH2 module) or in combination with GIV's GEF module (entire C-Term). Non-phosphorylatable phenylalanine mutants were generated in each case to serve as negative controls. These GIV substrates were inserted within the IMP probe shown in FIG. 1C.

FIGS. 6A-6B depict sources of various paired cancer cell lines used in the study: FIG. 6A is a schematic representing the technique that was employed by Massague et al (7) to generate paired primary and Brain metastatic clones. Briefly, 105 of metastatic lung or breast cancer cells isolated from lymphatic duct or pleural effusions of cancer patients were injected into arterial circulation of nude mice. Subsequently, tumor cells were isolated from lesions formed at secondary site i.e. brain or bone, followed by expansion of the cells and reinjection of the cells into mice circulation for two more rounds to select for highly metastatic clones. FIG. 6B is a list of paired (parental and brain mets) lung and breast cancer cell lines with variable metastatic proclivity used in the study, their varying genetic background, and known mutations and the sources of cells.

FIGS. 8A-8D show mining the PhosphositePlus (PSP) database and visualizing GO enrichment in the cancer-specific phosphoproteome. FIG. 8A-8B show a list of 72 phosphoproteins from the PSP database that fit the criteria for being found in cancers but excluded in normal tissues were subjected to an enrichment analysis using analysis tools from the PANTHER Classification System. Pathways (FIG. 8A) and GO biological processes (FIG. 8B) enriched among these 72 proteins compared to the entire human phosphoproteome as reference are displayed. FIG. 8C-8D show the list of phosphoproteins observed in cancers and the list of phosphoproteins observed in cancers but excluded in normal tissues were submitted to the Reduce+Visualize Gene Ontology (REVIGO) analysis tool and GO terms were visualized in a semantic similarity-based scatterplots on left and right, respectively. GO-biological process enriched in the pan-cancer phosphoproteome (left) is notable for regulators of cell cycle, DNA replication and multiple metabolic pathways. By contrast, negative regulation of apoptotic signaling pathway is the only GO-biological process that is enriched in the cancer-specific phosphoproteome (i.e., phosphoproteins observed in cancers, not in normal tissues). The colors do not reflect pathway direction but rather the degree of statistical significance. Red circles indicate regulated pathways that are different to a highly significant degree; green and blue also indicate significant difference, but to a lesser degree. The greyscales color intensity represents the negative log 10 p value for each of the statistically enriched pathways shown on the scatterplot.

FIG. 9A shows immunoblots showing the phosphorylation status of WT IMP-GIV-SH2 and its corresponding YF mutant after EGF stimulation. Only WT IMP peptides are phosphorylated but not its corresponding YF mutants. FIG. 9B shows immunoblots showing the phosphorylation status of WT IMP-GIV-CT and their corresponding YF and YF/FA mutants after EGF stimulation. Only WT IMP-GIV-CT probe gets phosphorylated but not its corresponding YF mutant. FIG. 9C shows serum-starved Cos7 cells expressing WT IMP-GIV-SH2 were stimulated with various growth factors prior to lysis. Lysates were immunoprecipitated with anti-GFP mAb and tyrosine phosphorylation of IMP-GIV-SH2 probe was analyzed by immunoblotting (IB). Phosphorylation of the peptide was observed in fed state (10% FBS) or when stimulated with EGF or Insulin or PDGF but not in overnight starved conditions. FIG. 9D shows serum-starved Cos7 cells expressing WT IMP-GIV-CT were stimulated with EGF or Insulin prior to lysis. Lysates were immunoprecipitated with anti-GFP mAb and tyrosine phosphorylation of IMP was analyzed by immunoblotting (IB). Phosphorylation of the IMP-GIV-CT-WT probe was only observed in cells when stimulated with either EGF or insulin but not in starved cells. FIG. 9E shows lysates of Cos7 cells co-expressing IMP-GIV-SH2 and wild-type (WT) or kinase-dead (KD) Src-HA were immunoprecipitated and analyzed for tyrosine phosphorylation of IMP as in FIG. 9D. Phosphorylation of the IMP-GIV-SH2 probe was only observed in cells co-transfected with Src-HA-WT but not in cells transfected with kinase dead Src-HA-KD cells. FIG. 9F shows lysates of Cos7 cells expressing IMP-GIVY1798 and wild-type (WT) or Kinase Dead (KD) FAK-HA were immunoprecipitated and analyzed for tyrosine phosphorylation of IMP as in FIG. 9D. Phosphorylation of the IMP-GIV-SH2 probe was only detected in cells expressing WT-FAK-HA but in kinase dead FAK-HA expressing cells. FIG. 9G shows lysates of Cos7 cells expressing IMP-GIV&1798 and wild-type (WT) or catalytically dead (CD) SHP1-HA were immunoprecipitated and analyzed for tyrosine phosphorylation of IMP as in FIG. 9D. Phosphorylation of the IMP-GIVY1798 probe was only detected in cells expressing SHP1-HA-CD but in SHP1-HA-WT expressing cells.

FIG. 11A-11B show representative steady state FRET images of PC-9 parental and BrM cells expressing IMP-Y1764F mutant probe. IMP Y1764F mutant peptide shows no differential FRET signal when expressed in paired cancer cell lines; very little FRET was observed in both the parental and BrM PC-9 cell groups at steady state in 10% serum, indicating that tyrosine phosphorylation of the IMP probe is essential for the differential FRET observed in these cells using the WT probe 2e. FIG. 11B shows scatter plots display the FRET efficiency at the PM in FIG. 11A. Results are expressed as mean±S.D. FIG. 11C shows whole cell lysates from paired PC-9, H2030 and MDA-MB-231 cells were immunoblotted with total phosphorylated tyrosine antibody. Full-length phosphotyrosine immunoblot shows no discernable differences in either global tyrosine phosphorylation or tyrosine phosphorylation at any given molecular weight between the parental and the BrM clones. Results indicate that the differences in FRET in these paired cells observed using the IMP-Y1764 probe in FIG. 2D-2F does not merely reflect global differences in tyrosine phosphorylation. FIGS. 11D-11F show replacement of the GIV substrate sequence with a sequence derived from IRS1 abolishes the ability of IMP probes to distinguish cancer cells with high from low metastatic potential. FIG. 11D is a schematic showing the substrate sequence of GIV used in IMP-Y1764 (RKTEDTYFISSAG (SEQ ID No: 1)) and IMP-Y1798 (SKDSNPYATLPRA (SEQ ID No: 2)) probes, and the sequence of IRS1 (ETGTEEYMKMDLG (SEQ ID No: 3)) that was used to substitute the residues flanking the Y substrate. Previous work has shown that this site is phosphorylated by multiple growth factors (EGF, PDGF and Insulin) and is a binding site for p85α(PI3K) and induces FRET when used in similar probe design as IMPs. FIG. 11E shows parental and brain metastatic (BrM) clones of PC-9 lung cancer cells expressing IMP-Y941 IRS were analyzed for steady-state FRET by confocal live-cell imaging. Representative CFP, YFP and FRET images are shown. Boxed area on the left is magnified on the right. FRET is frequently observed at the PM in parental, but not in BrM clones. FIG. 11F shows scatter plots display the FRET efficiency at the PM in FIG. 11E. Results are expressed as mean±S.D.

FIG. 12A shows whole cell lysates of MCF7 and MDA-MB-231 cells were analyzed for GIV, phospho(p)Akt, total(t)Akt and tubulin by immunoblotting (IB). FIG. 12B shows immunoprecipitation was carried out from lysates of MCF7 and MDA-MB-231 cells expressing IMP-Y1764 with anti-GFP mAb and analyzed for tyrosine phosphorylation of IMP by immunoblotting (IB). FIG. 12C shows MCF7 and MDA-MB-231 cells expressing IMP-Y1764 were analyzed for steady-state FRET by confocal live-cell imaging. Representative CFP, YFP and FRET images are shown. Boxed area on the left is magnified on the right. FIG. 12D shows bar graphs display the FRET efficiency (F.E) in FIG. 12C. The cut-off F.E of 0.14 (based on the cumulative histograms in FIG. 4G) denotes that MCF7 cells with low F.E and MDA-MB-231 cells with high F.E have low and high metastatic potentials, respectively. Results are expressed as mean±S.D.

FIG. 13A is a schematic summarizing the characteristics of the 21T series of breast cancer cells. These isogenic cells were derived from the same patient (#21) during breast cancer progression (FIG. 3H). FIG. 13B depicts 21T cells expressing IMP-Y1764 were analyzed for steady-state FRET by confocal live-cell imaging. Representative FRET images are shown as a montage of single-cells images. Quantifications are displayed as scatter plots in FIG. 3I.

FIGS. 15A-15B depict tyrosine phosphorylation of GIV at the PM is enhanced during drug resistance. FIG. 15A is a table of paired (sensitive vs resistant) breast (Hs578T) and lung (HCC827) cancer cells used in this study, the underlying pathways implicated in the development of drug resistance, the genetic background and the source of cells. FIG>15B depicts Docetaxel (DTX)-sensitive and resistant pairs of Hs578T, and Lapatinib/Erlotinib sensitive and resistant pairs of HCC827 cells were fixed, stained for tyrosine phosphorylated GIV (pYGIV; red greyscales) and DAPI (nucleus; blue greyscales) and analyzed by confocal microscopy. Representative images of cells are shown. Bar=10 μm.

DETAILED DESCRIPTION

Figure 1A:
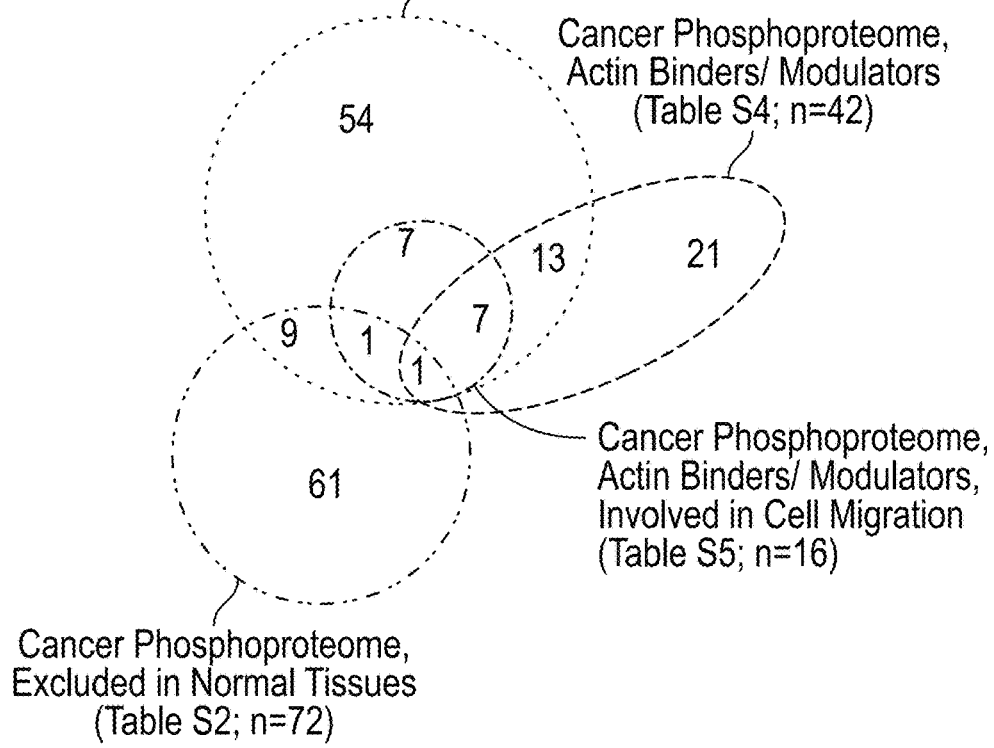
FIGS. 1A-1K provide a rationale, design and biochemical validation of IMPs.

The present invention provides a method for detecting metastatic potential and/or chemoresistance in single cells, comprising: providing one or more multi-modular biosensors; providing a sample comprising a cell; contacting said sample with the one or more biosensors under conditions that allow folding of probe donor and acceptor fluorescent proteins into close proximity; and detecting fluorescence resonance energy transfer (FRET) signal to detect said interacting molecules.

In embodiments, the present invention provides a method for detecting metastatic potential and/or chemoresistance in single cells, wherein the one or more multi-modular biosensors target short stretches of the C-terminus of GIV flanking one or both of tyrosines, Y1764 and Y1798, and N—SH2 domain of p85α(PI3K).

In embodiments, the present invention provides a method for detecting metastatic potential and/or chemoresistance in single cells, wherein the multi-modular biosensor consists of two modules.

In embodiments, the present invention provides a method for detecting metastatic potential and/or chemoresistance in single cells, wherein the two modules are separated by a flexible linker and sandwiched by eCFP (donor) and eYFP (acceptor) proteins, such that binding of the N-SH2-p85α (PI3K) to phosphotyrosine (pY) GIV ligand leads to folding of the probe bringing donor and acceptor in proximity sufficient to generate a detectable FRET signal.

In embodiments, the present invention provides a method for detecting metastatic potential and/or chemoresistance in single cells, wherein the single cells, are cancer cells.

In embodiments, the present invention provides a method for detecting metastatic potential and/or chemoresistance in single cells, wherein the single cells, are cells associated with fibrogenesis, diabetes, aging, and/or infertility.

The present invention provides a method for identifying agents specifically targeting a GNAI:GIV interface, comprising: providing one or more multi-modular biosensors; providing a sample comprising a cell; contacting said sample with the one or more biosensors to form a first mixture under conditions that allow the folding of probe donor and acceptor fluorescent proteins into close proximity; detecting a first FRET signal to detect said interacting molecules; contacting said first mixture with an agent under said conditions that allow the folding of probe donor and acceptor fluorescent proteins into close proximity; detecting a second FRET signal to detect said interacting molecules; and determining the difference between said first and said second FRET signal.

In embodiments, the present invention provides a method for identifying agents specifically targeting the GNAI:GIV interface, wherein the one or more biosensors target short stretches of the C-terminus of GIV flanking one or both of tyrosines, Y1764 and Y1798, and the N—SH2 domain of p85α(PI3K).

In embodiments, the present invention provides a method for identifying agents specifically targeting the GNAI:GIV interface, wherein the multi-modular biosensor consists of two modules.

In embodiments, the present invention provides a method for identifying agents specifically targeting the GNAI:GIV interface, wherein the two modules are separated by a flexible linker and sandwiched by eCFP (donor) and eYFP (acceptor) proteins, such that binding of N-SH2-p85α (PI3K) to phosphotyrosine (pY) GIV ligand leads to folding of the probe bringing donor and acceptor in proximity sufficient to generate a detectable FRET signal.

In embodiments, the present invention provides a method for identifying agents specifically targeting the GNAI:GIV interface, wherein the sample comprises cancer cells.

In embodiments, the present invention provides a method for identifying agents specifically targeting the GNAI:GIV interface, wherein sample comprises cells associated with fibrogenesis, diabetes, aging, and/or infertility.

The present invention provides a biosensor device for detecting metastatic potential and/or chemoresistancy of single cells comprising a biosensor that targets short stretches wherein the one or more multi-modular biosensors target short stretches of the C-terminus of GIV flanking one or both of tyrosines, Y1764 and Y1798, and N—SH2 domain of p85α(PI3K).

In embodiments, the present invention provides a biosensor device for detecting metastatic potential and/or chemoresistancy of single cells, wherein the multi-modular biosensor consists of two modules.

In embodiments, the present invention provides a biosensor device for detecting metastatic potential and/or chemoresistancy of single cells, wherein the two modules are separated by a flexible linker and sandwiched by eCFP (donor) and eYFP (acceptor) proteins, such that binding of the N-SH2-p85α(PI3K) to phosphotyrosine (pY) GIV ligand leads to folding of the probe bringing donor and acceptor in proximity sufficient to generate a detectable FRET signal.

The present methods can also include the subsequent step of treating the cells, or subject providing the cell, with an effective amount of a composition or therapy to inhibit the cancer.

All publications, patents, and patent applications mentioned in this specification are herein incorporated by reference to the same extent as if each individual publication, patent, or patent application was specifically and individually indicated to be incorporated by reference. Citations to publications herein is intended to reference the latest edition available.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as Molecular Cloning: A Laboratory Manual, second edition (Sambrook et al., 1989) Cold Spring Harbor Press; Oligonucleotide Synthesis (MJ. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and CC. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (CA. Janeway and P. Travers, 1997); Antibodies (P. Finch, 1997); Antibodies: a practical approach (D. Catty., ed., IRL Press, 1988-1989); Monoclonal antibodies: apractical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

EXAMPLES

Provided herein are exemplary methods for measuring single cell imaging of metastatic potential of cancer cells.

Figure 7A:
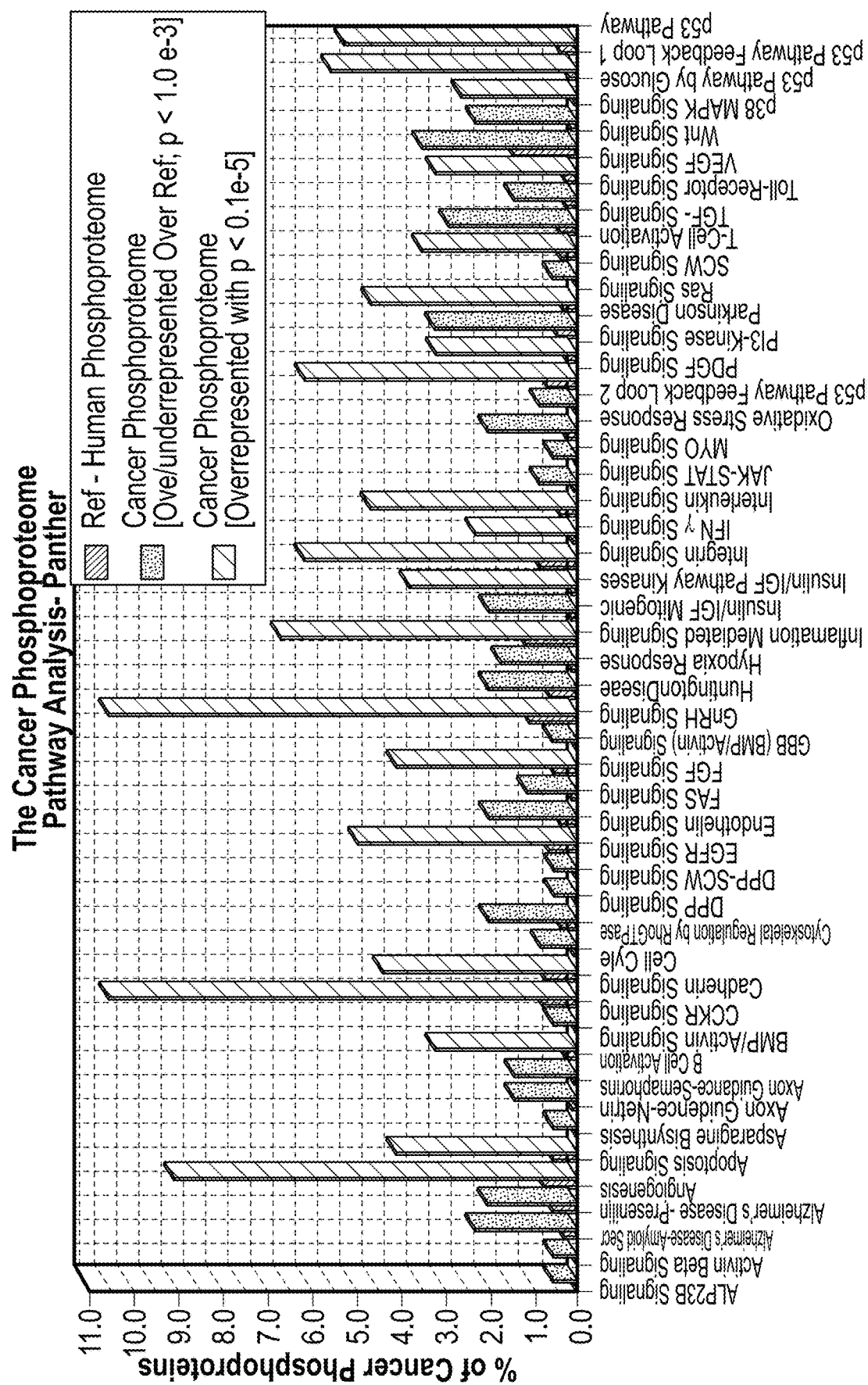
FIGS. 7A and 7B show mining the PHOSPHOSITEPLUS (PSP) database for pan-cancer phosphoproteome. 324 proteins whose phosphosites are observed in cancers were subjected to an enrichment analysis using analysis tools from the PANTHER Classification System. Pathways (FIG. 7A) and GO-biological processes (FIG. 7B) enriched among these 324 proteins compared to the entire human phosphoproteome as reference are displayed. % of protein in the category is calculated for each list (the human phosphoproteome reference list and the pan-cancer phosphoproteome list) as: (#proteins for the category/ #proteins in the list)× 100. Underrepresented pathways are highlighted in green greyscales.
Figure 7B:
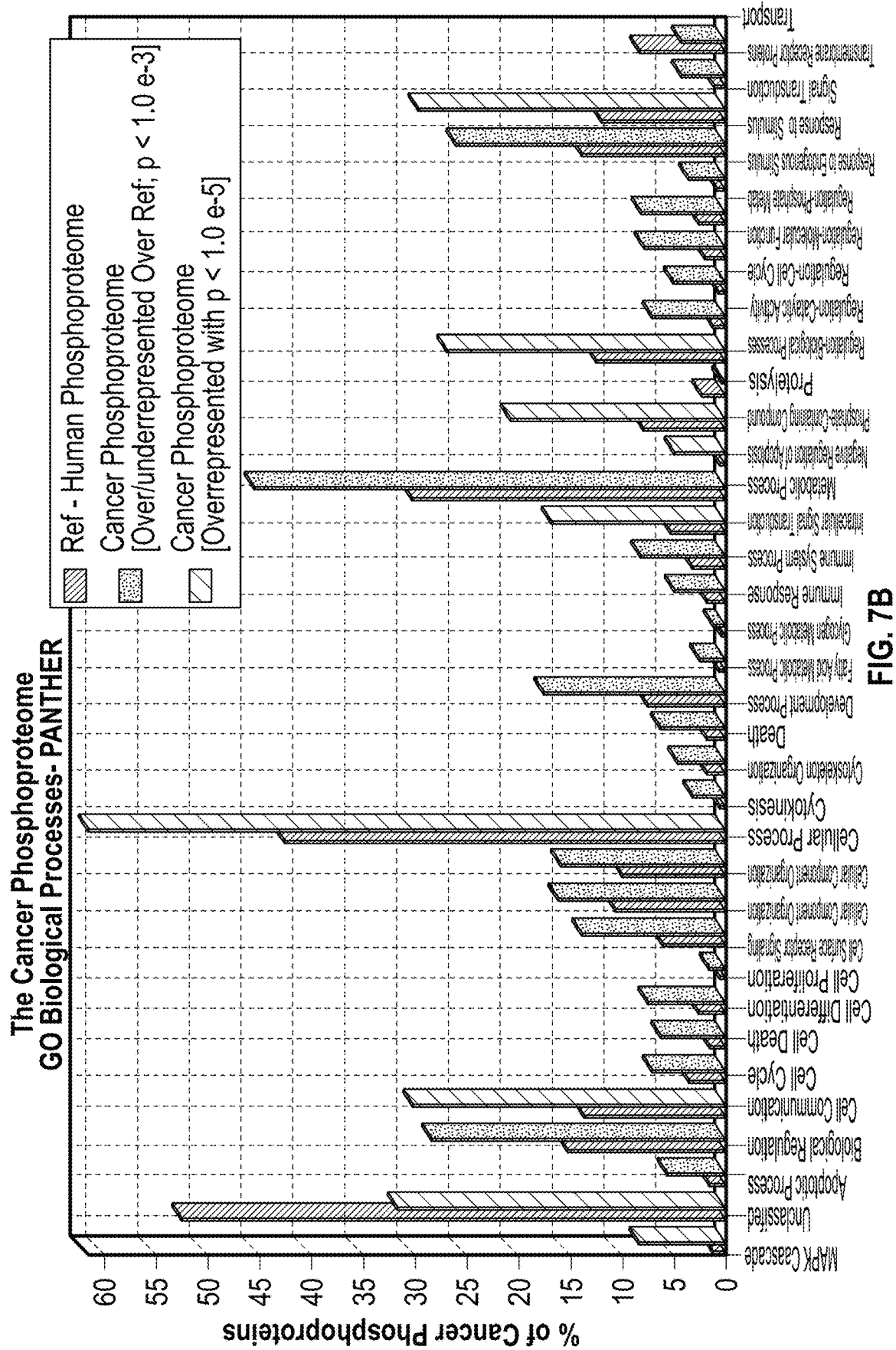
Figure 8A:
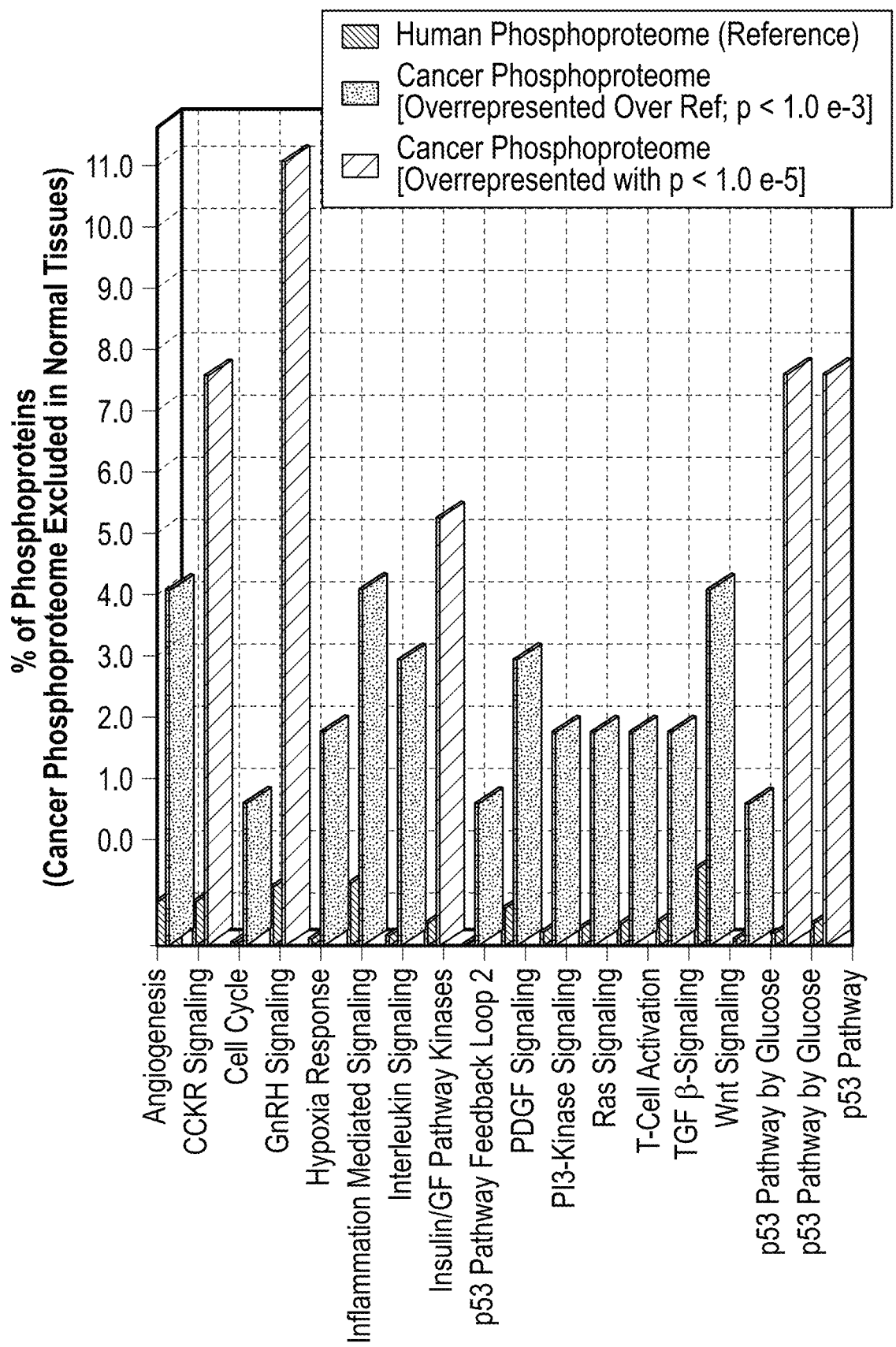
Figure 8B:
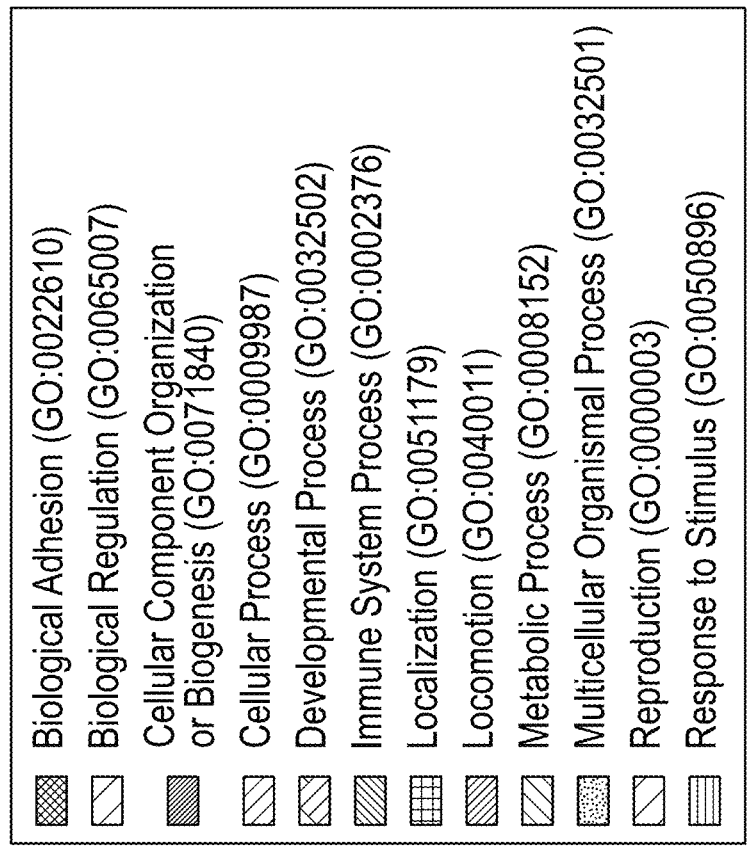
Figure 8B:
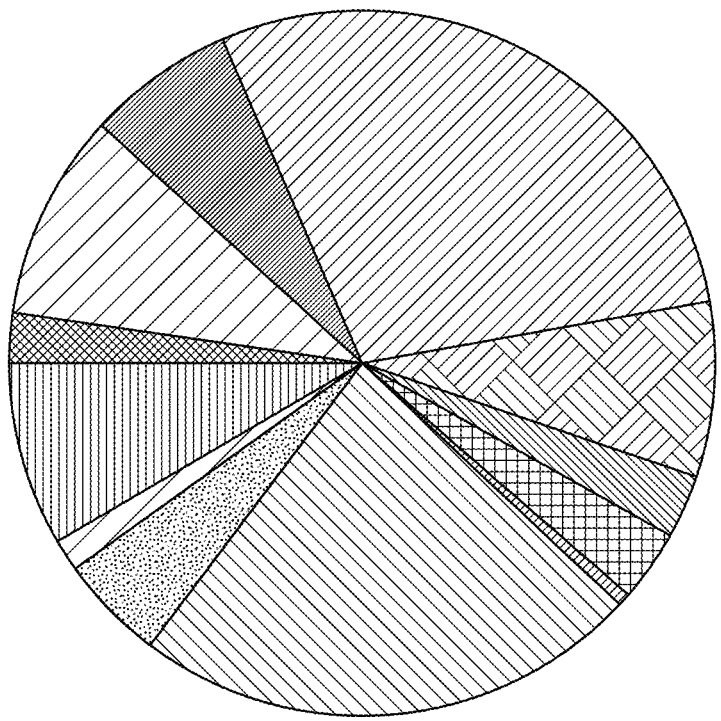

In search of an ideal target, a comprehensive analysis of the pan-cancer phosphoproteome using the NIH-supported, continuously-curated, and interactive systems biology resource, PHOSPHOSITEPLUS (PSP) (24-26) was perfomed to study experimentally observed post-translational modifications in the regulation of biological processes. Using powerful gene ontology (GO)-analytical tools [PANTHER(27), GOrilla(28) and REVIGO(29)] for mining, interpreting and visualizing this data several pathways and biological processes were noted as being overrepresented in the pan-cancer phosphoproteome above the pan-human phosphoproteome set as reference (see FIG. 7). A handful of pathways (FIG. 8A) and biological processes (FIG. 8B-8C) were over- or under-represented over the reference set, and only one GO term enriched over others, i.e., negative regulators of apoptosis (FIG. 8D). Because high-resolution imaging of metastasizing cancer cells has underscored the importance of the actin cytoskeleton remodeling as a fundamental prerequisite for cancer invasion (16). The pan-cancer phosphoproteome was searched using a combination of different criterions for enriching for either 'cellular processes' (the largest GO-biological process enriched in cancer-specific phosphoproteins; FIG. 8B), actin binders/modulators and those involved in cell migration (the most important property of tumor cells that has marked effects on tumor growth, resistance and spread (30)), and is excluded from normal tissues (FIG. 7). Only one phosphopeptide, pY1798 in a protein named GIV/GRDN (Gα Interacting Vesicle-associated; a.k.a Girdin; gene: CCDC88A) fit all the criteria.

Figure 1B:
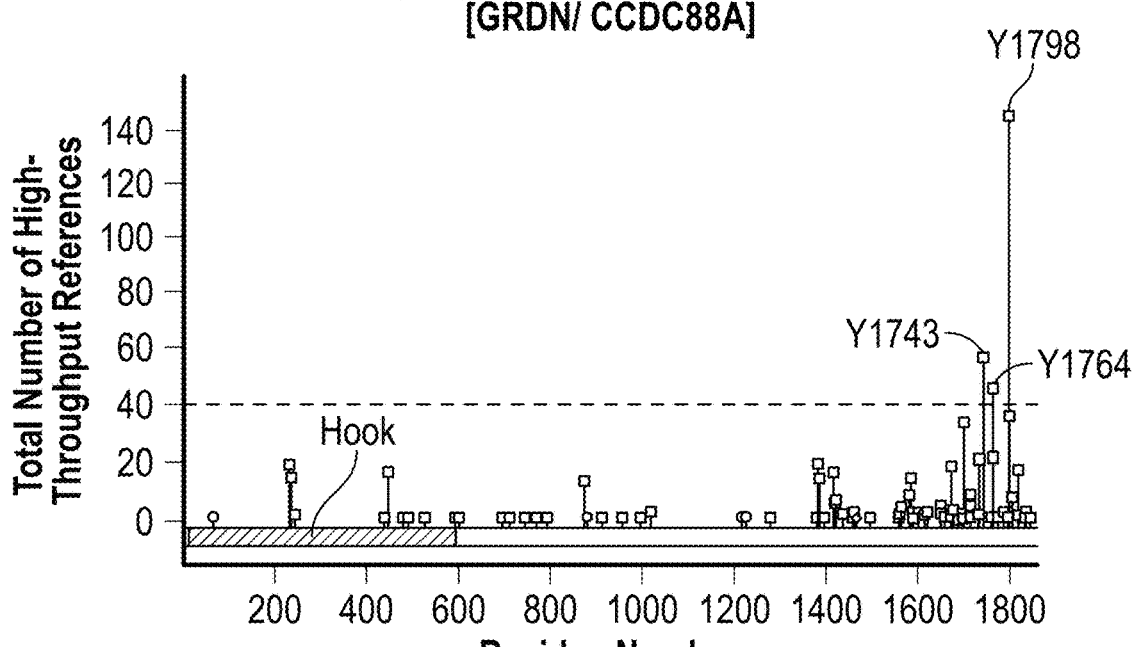
Figure 5A:
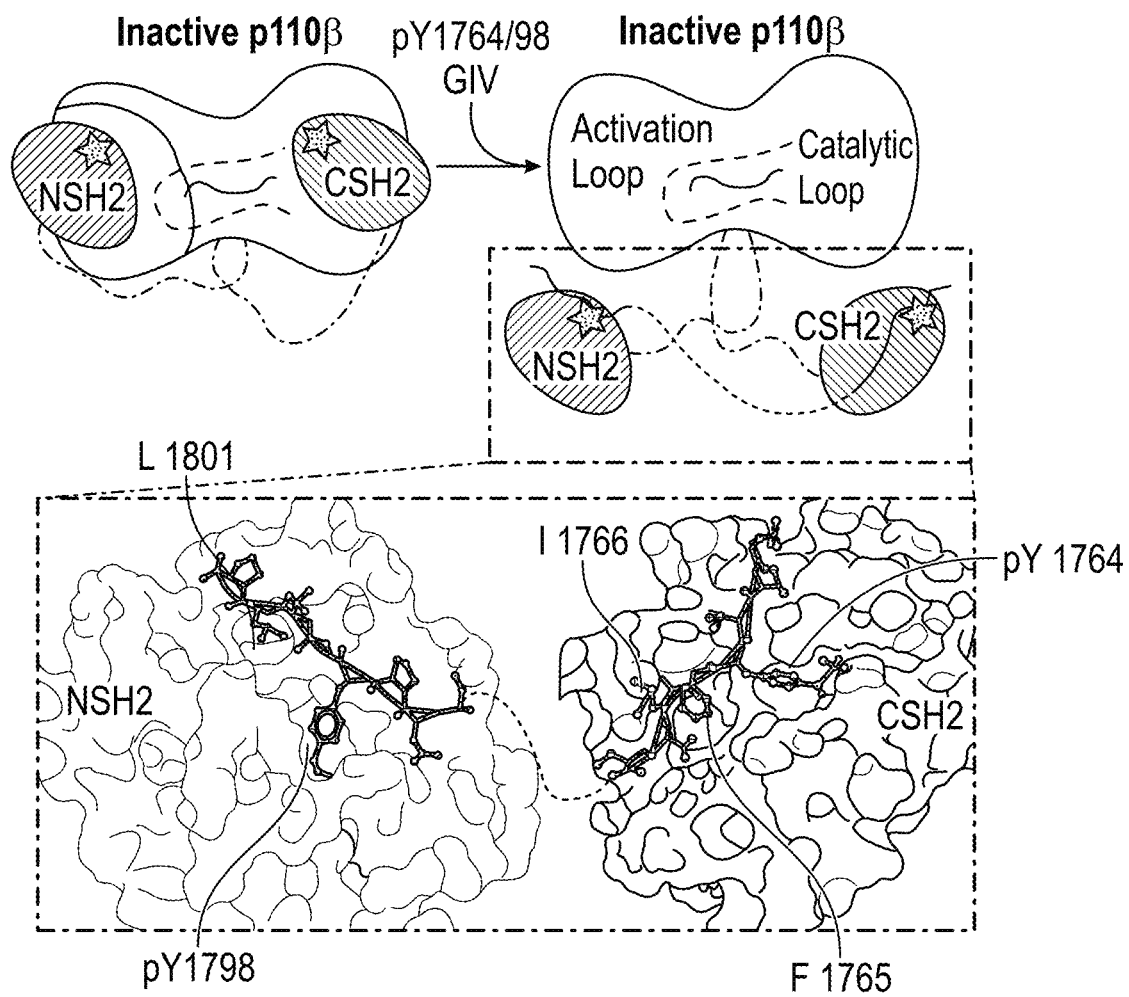

GIV, a cytosolic guanine nucleotide exchange modulator (GEM), is a bona fide metastasis-related protein known to integrate signals downstream of multiple classes of receptors by coupling ligand-activated receptors to activation of trimeric GTPases (31-33). Consequently, receptor-initiated signals are modulated by G protein intermediates (34). Ligand stimulation of a variety of receptors directly [as in the case of growth factor receptor tyrosine kinases (RTKs)] or indirectly [via non-RTKs, as in the case of GPCRs, TLRs, Integrins]trigger phosphorylation of GIV on two key tyrosines (Y1764 and Y1798) within its C-terminus (FIG. 1B), which directly bind and activate Class 1 PI3Ks, and subsequently, Akt (35) (FIG. 5). Multiple groups have independently validated the role of this multi-receptor-GIV-PI3K axis in driving metastasis and/or enhancing prometastatic features of tumor cells across a variety of solid cancers [summarized in (36)]. These studies have established causal links between GIV and several ominous traits that aid in the acquisition of metastatic potential, e.g., invasiveness, survival, stemness, and chemoresistance [summarized in (31)].

Figure 1C:
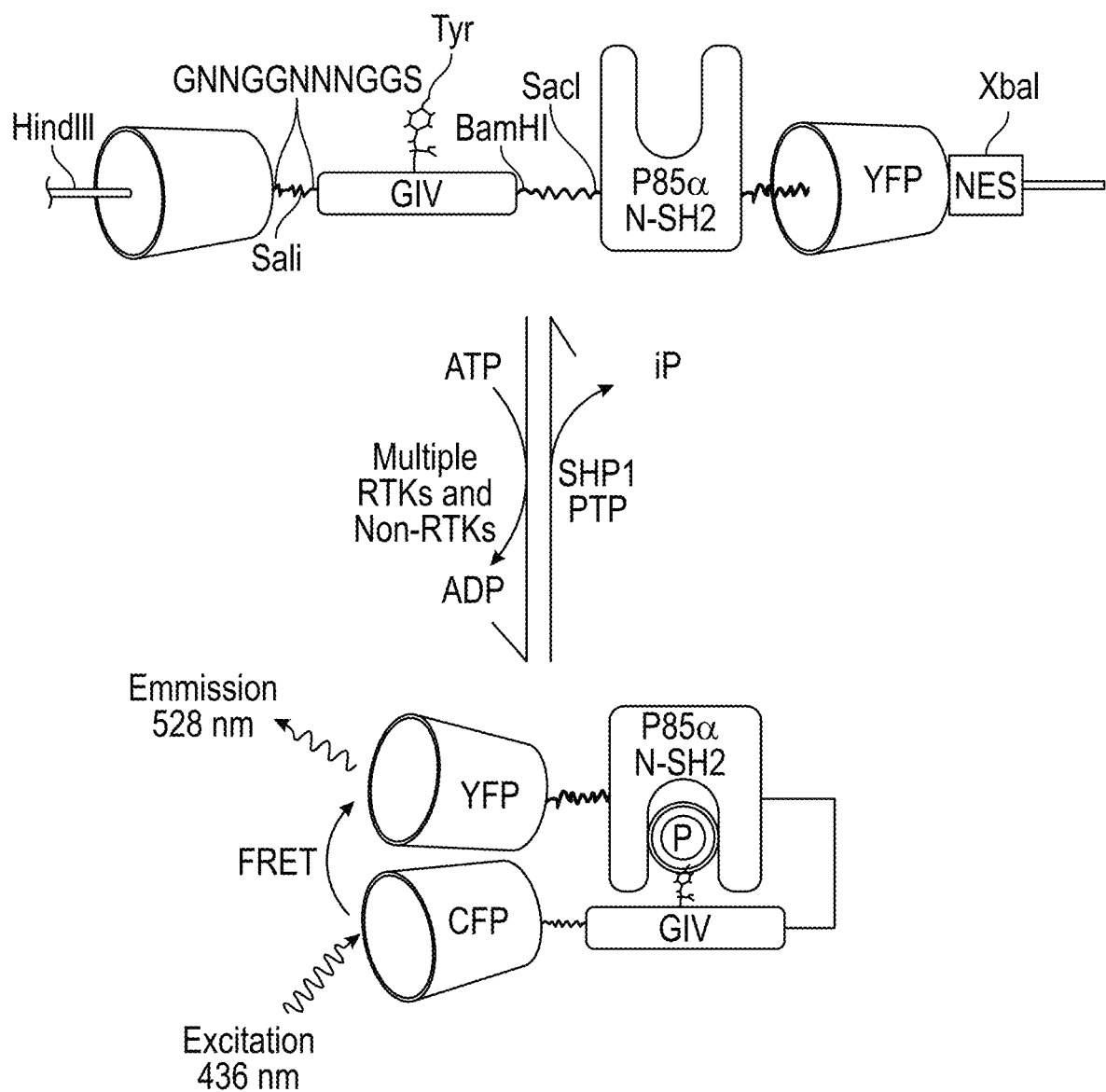

In order to determine that the measurement of the intensity of functional phosphorylation of GIV within the multi-receptor-GIV-PI3K axis in individual living cells will serve as a surrogate to assess the extent of multi-receptor-driven prometastatic signaling via the GIV-PI3K node, intramolecular FRET probes with 2 modules was designed (FIG. 1C). Short stretches of GIV flanking either one or both critical tyrosines, Y1764 and Y1798 (FIG. 5B), and 2)N—SH2 domain of p85α(PI3K); the former serves as a target substrate for multiple tyrosine kinases, and when phosphorylated serves as the ligand for recognition by N-SH2-p85α(PI3K). The two modules are separated by a flexible linker and sandwiched by eCFP (donor) and eYFP (acceptor) proteins, such that binding of the N-SH2-p85α(PI3K) to phosphotyrosine (pY) GIV ligand leads to folding of the probe bringing donor and acceptor fluorescent proteins into close proximity, with resultant gain in FRET. These synthetic probes were built to assess multireceptor-GIV-PI3K signaling, and are referred to as 'Integrators of Metastatic Potential (IMPs)'.

Figure 1D:
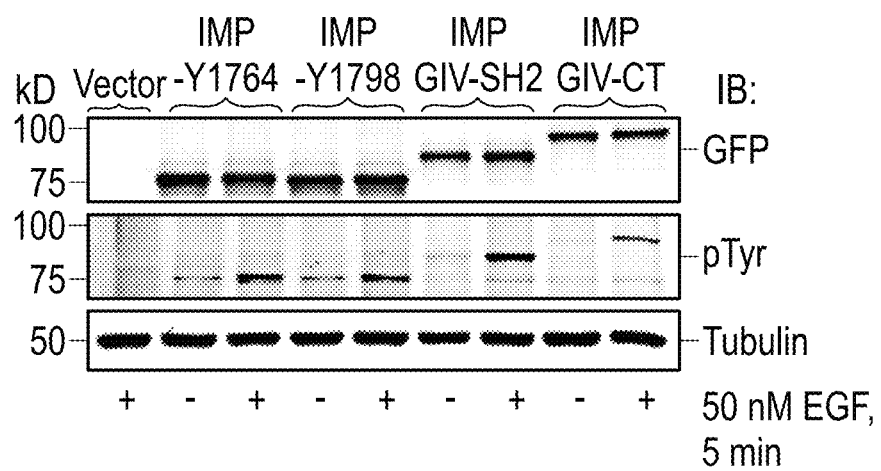
Figure 1E:
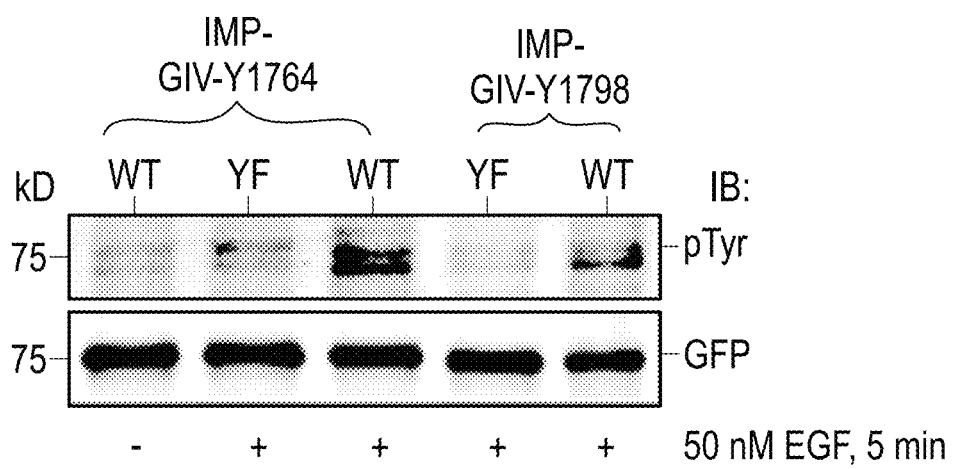
Figure 1F:
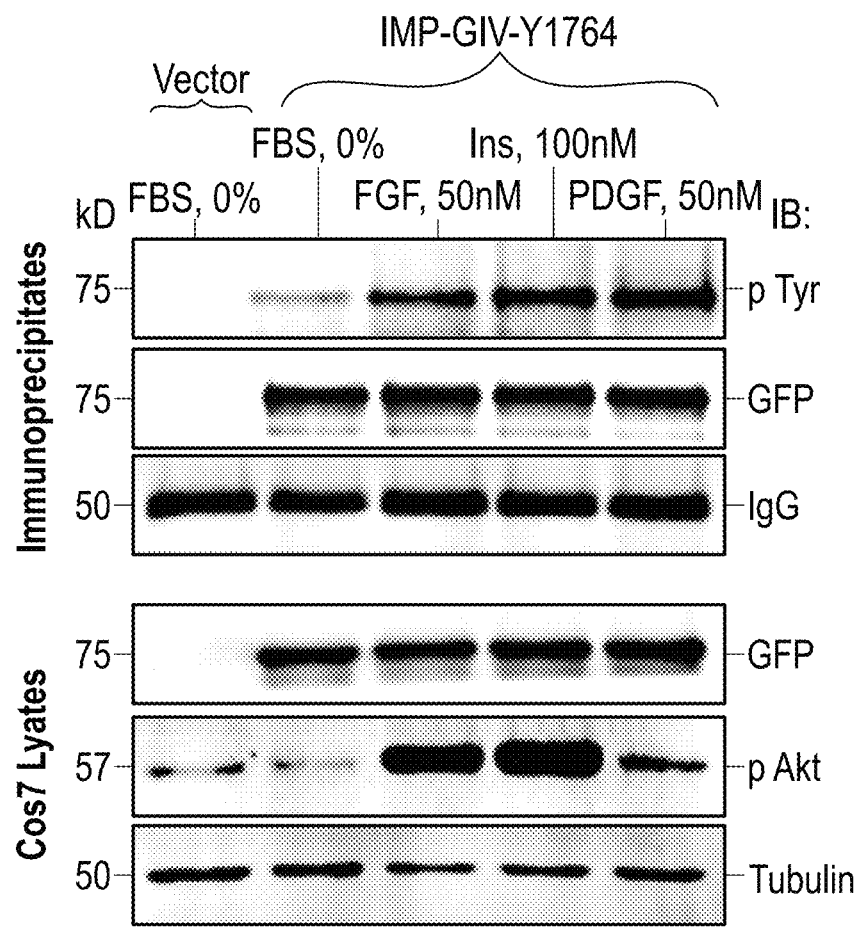
Figure 1G:
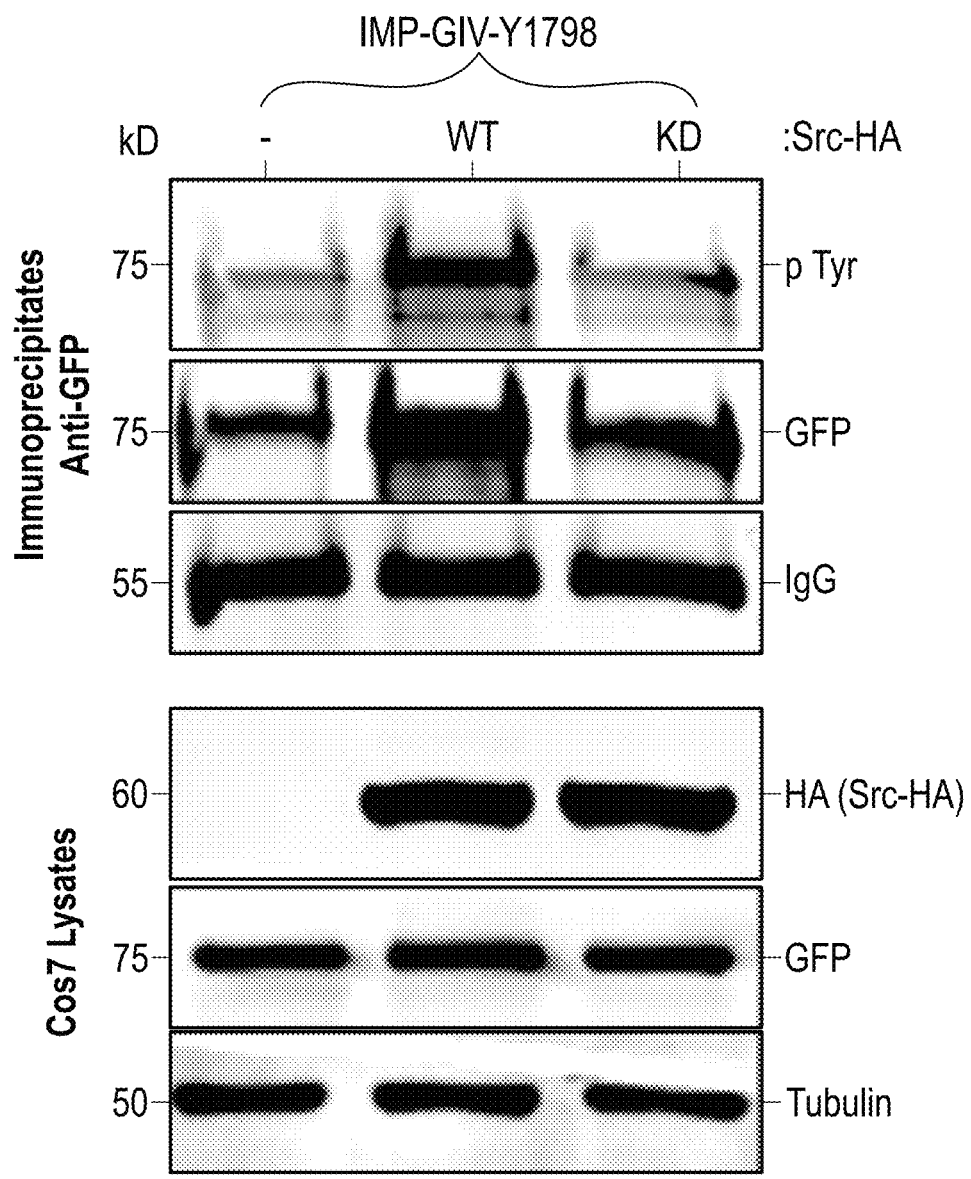
Figure 1H:
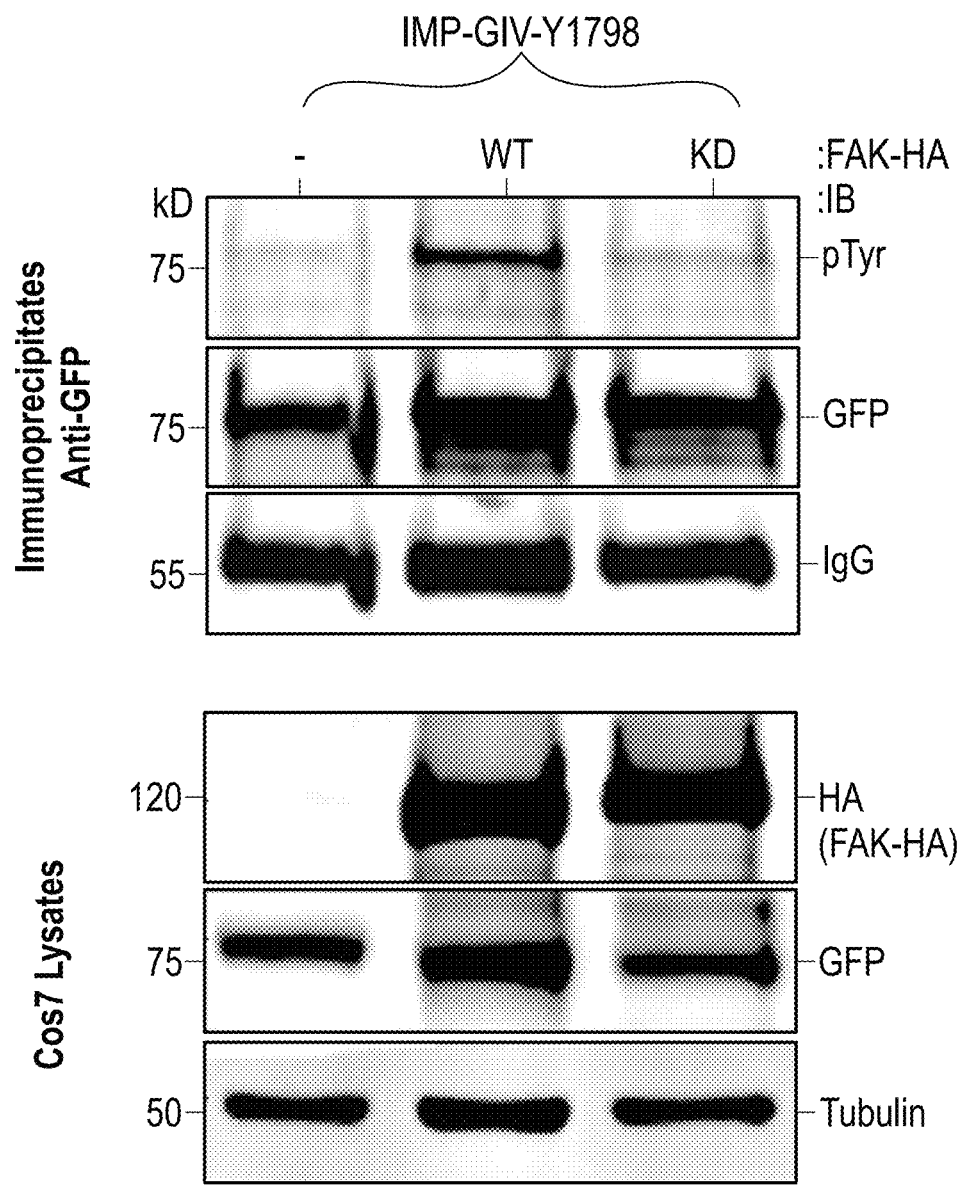
Figure 1I:
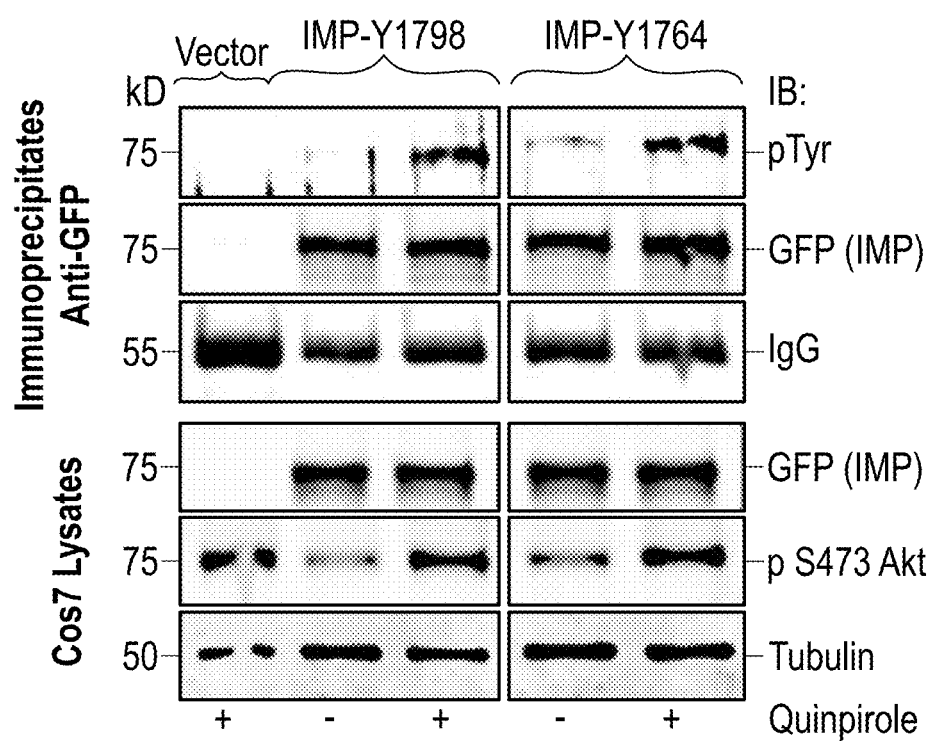
Figure 1J:
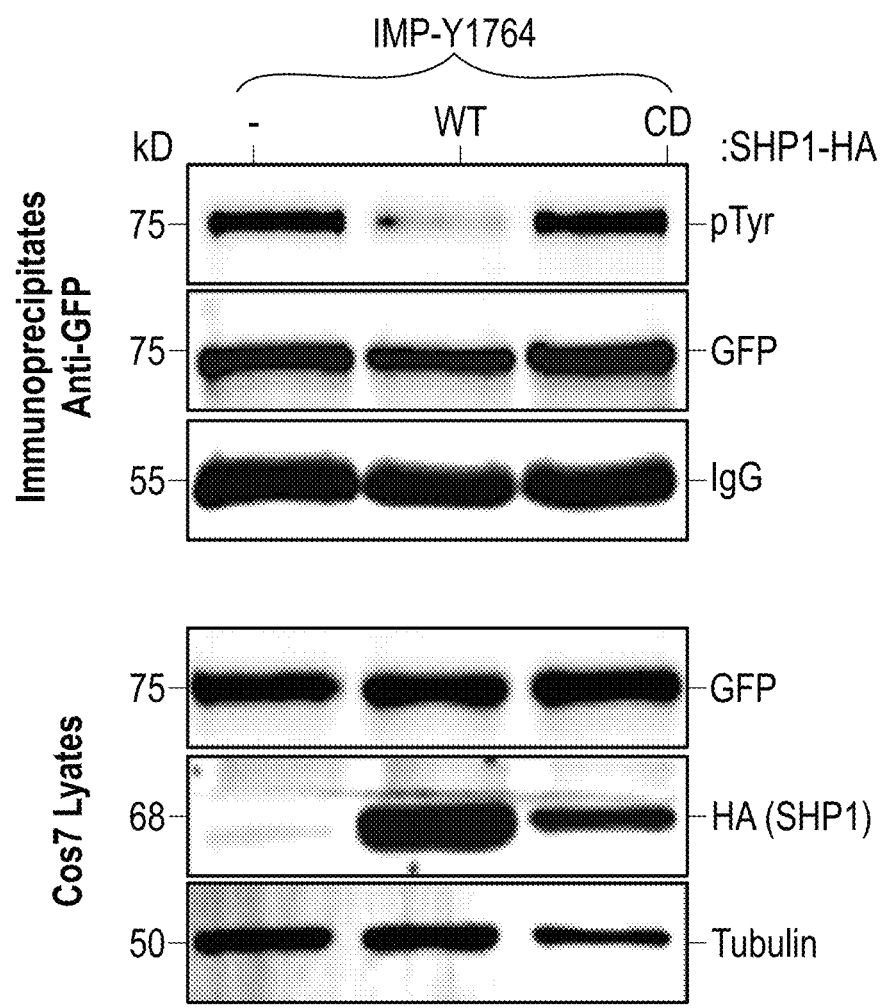
Figure 1K:
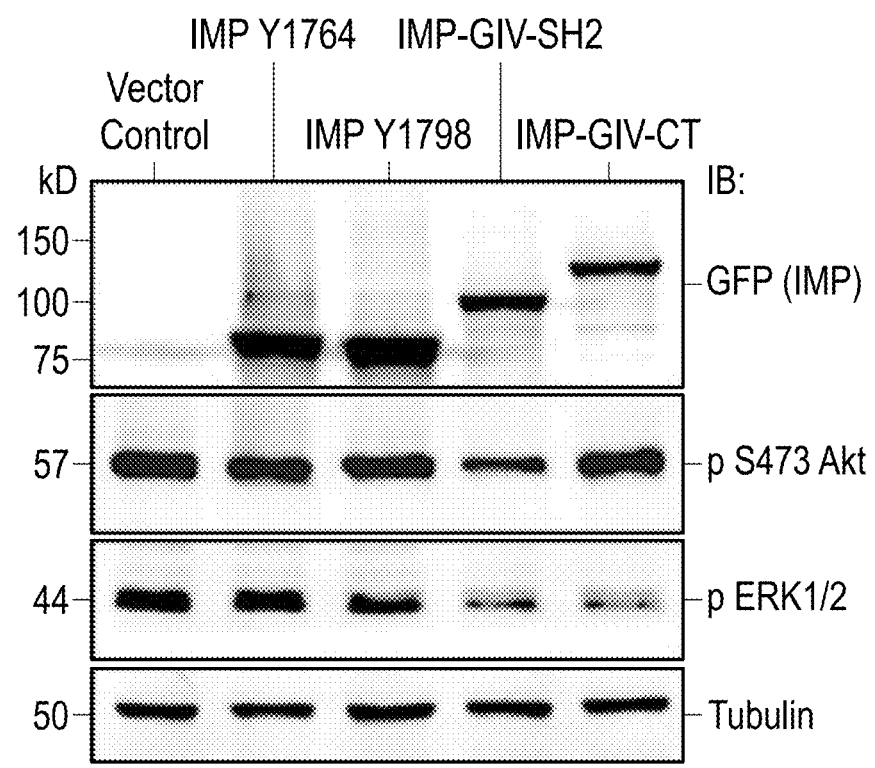
Figure 9A:
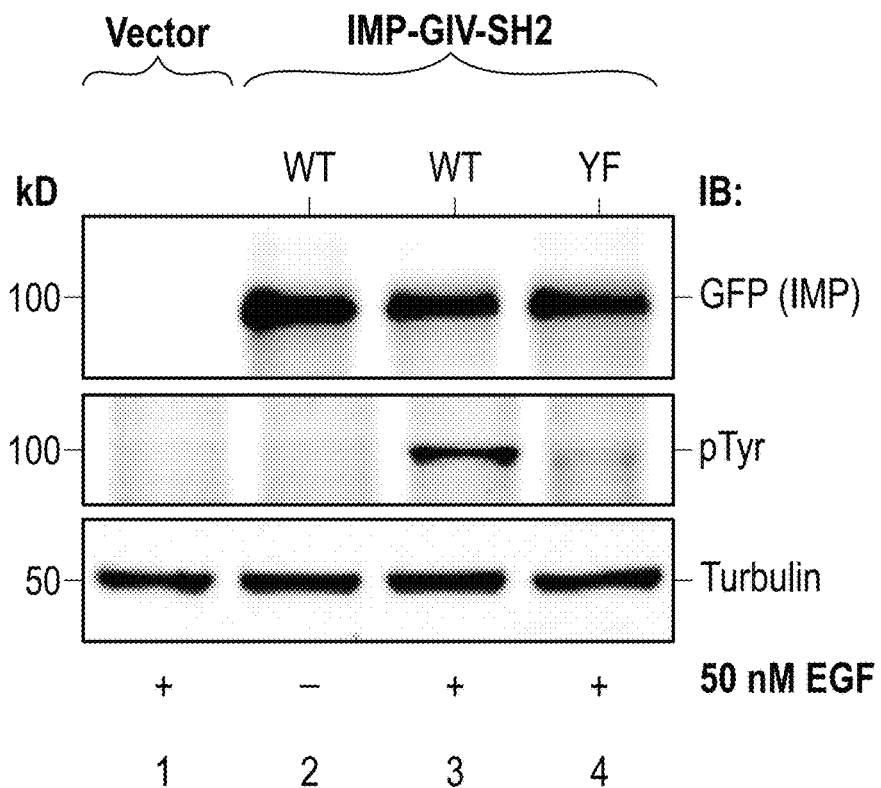
FIGS. 9A-9G show GIV-derived IMP probes are reversibly tyrosine phosphorylated in cells.
Figure 9B:
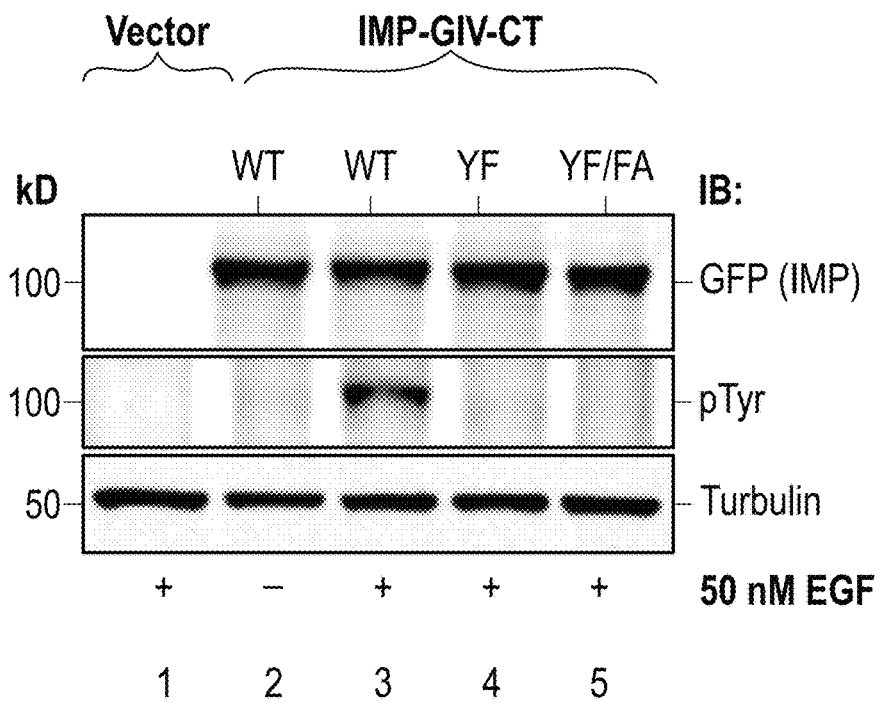
Figure 9C:
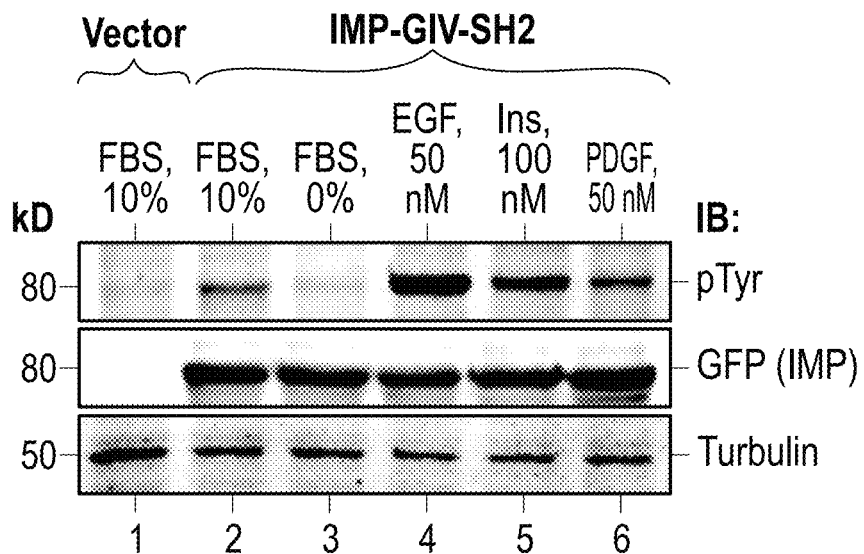
Figure 9D:
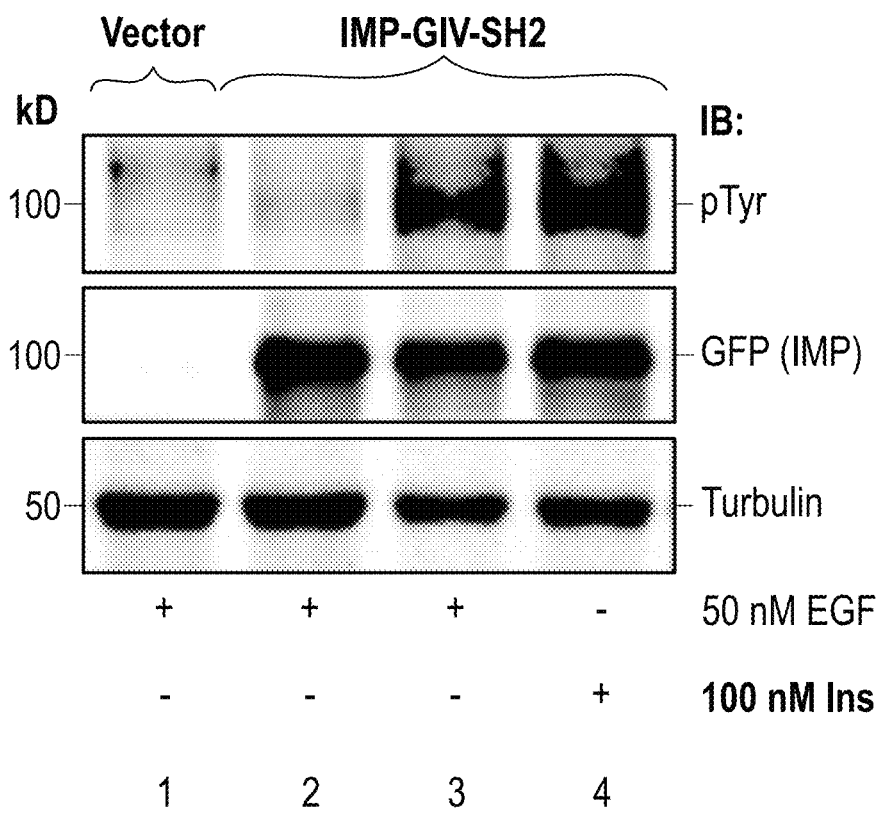
Figure 9E:
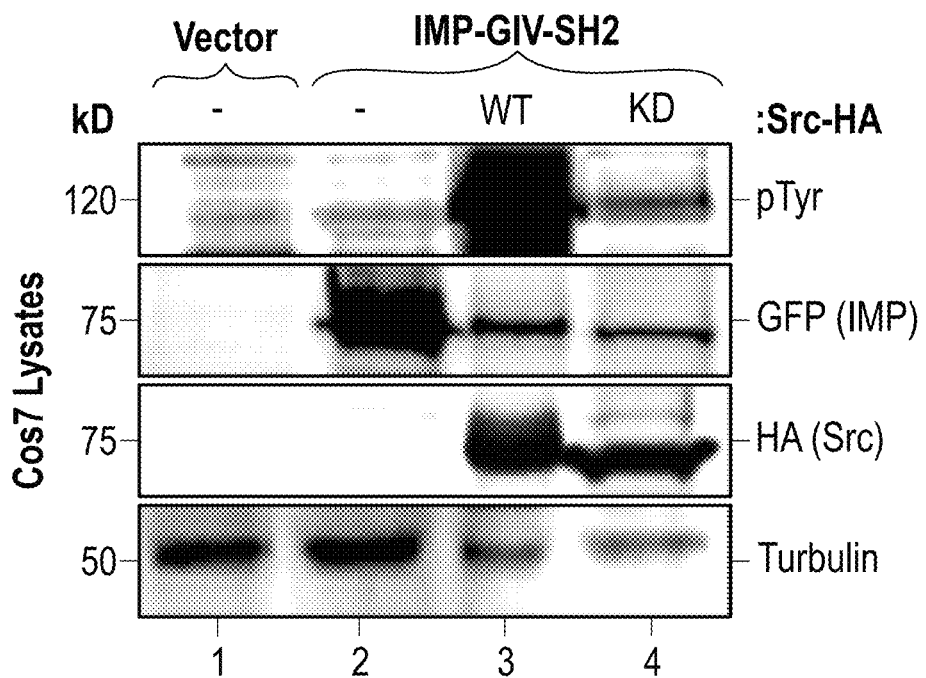
Figure 9F:
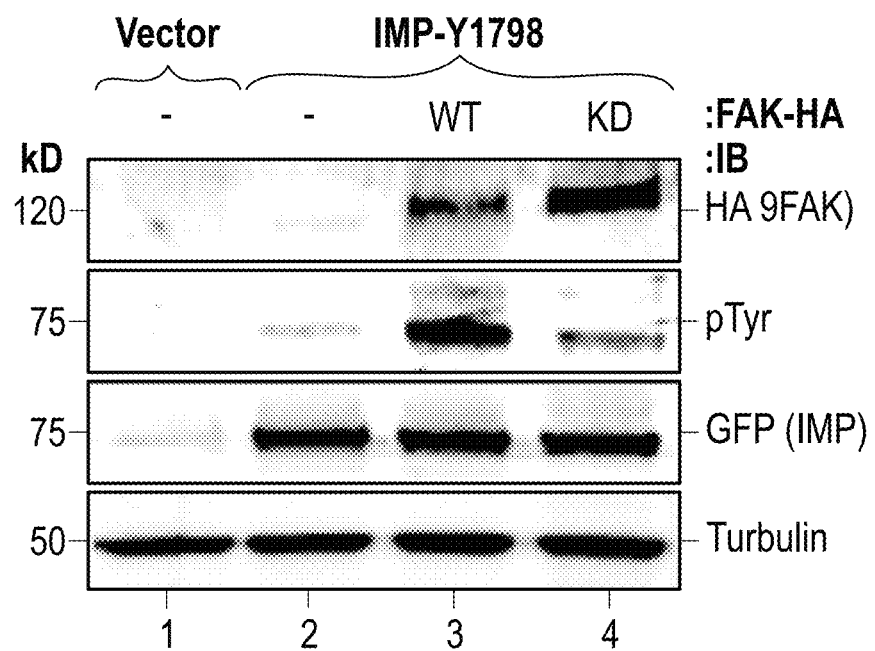
Figure 9G:
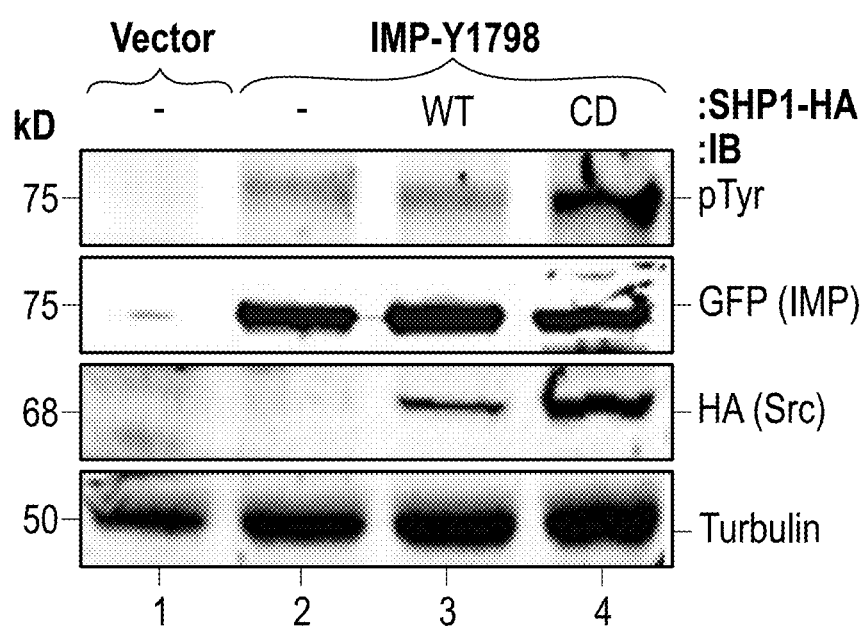

The IMP-probes were validated biochemically by confirming that they are expressed as fluorescent-tagged proteins of expected size and that they are phosphorylated on tyrosines after ligand (EGF) stimulation (FIG. 1D). Ligand-dependent phosphorylation was virtually abolished when the corresponding phosphorylation-deficient IMPs were expressed in which Tyr (Y) were substituted by Phe (F) (henceforth referred to as YF) (FIGS. 1E, 9A, and 9B). Consistent with the fact that multiple pathways converge on GIV, IMPs were phosphorylated upon stimulation with multiple growth factors (EGF, Insulin, PDGF) (FIGS. 1F, 9C, and 9D), non-receptor tyrosine kinases Src and FAK (FIGS. 1G, 1H, 9E, and 9F) and ligand for LPAR, a G-protein coupled receptor (FIG. 1I). Expression of catalytically active SHP-1, a protein tyrosine phosphatase that dephosphorylates GIV's tyrosines (37), abolished tyrosine phosphorylation of IMPs (FIGS. 1J and 9G). Ideal biosensors do not perturb the system under test (38), and isolated domains of GIV that can bind RTKs or activate G proteins can display a range of biologic activity (39) and alter the ratio of Akt and ERK signals. In the presence of a functional Src-homology-2 (SH2)-like or GEF module (39, 40) IMP-SH2 and IMP-GIV-C-terminus (IMP-CT) constructs (shown in FIG. 5B) altered the levels of Akt and ERK signals at baseline steady-states, whereas, under the same conditions the IMP-1764 or IMP-1798 constructs that contain merely 13 aa of GIV appeared inert (FIG. 1K). Hence, these two minimalist IMPs were deemed appropriate for further evaluation. While both Y1764/98 cooperatively activate PI3Ks, Y1764 is a target for both RTKs and non-RTKs, whereas Y1798 is exclusively phosphorylated by non-RTKs (35).

Figure 2A:
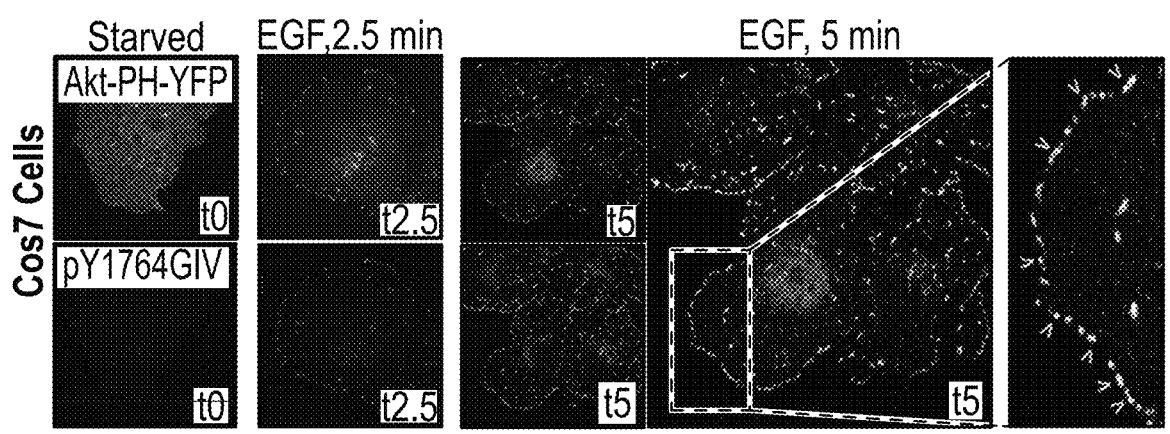
FIGS. 2A-2K provide a validation of the IMPs using single-cell FRET imaging.
Figure 2B:
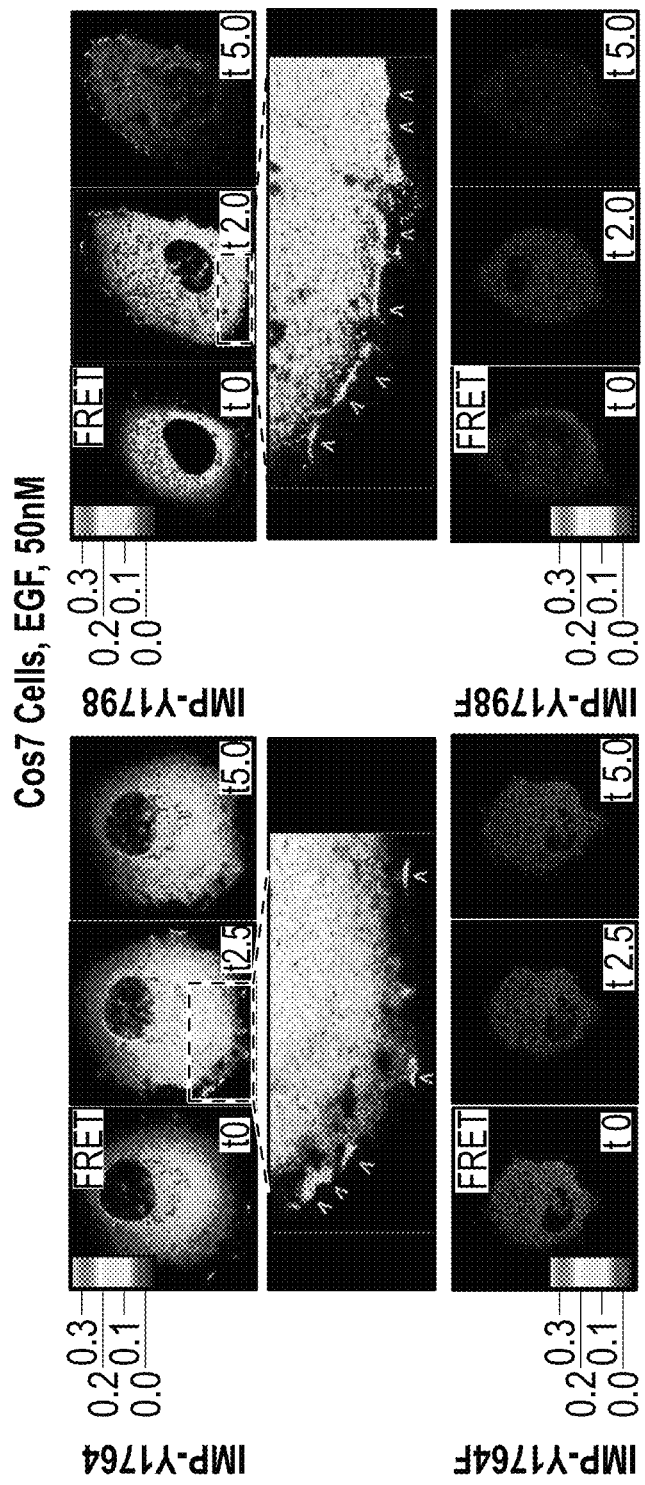
Figure 2C:
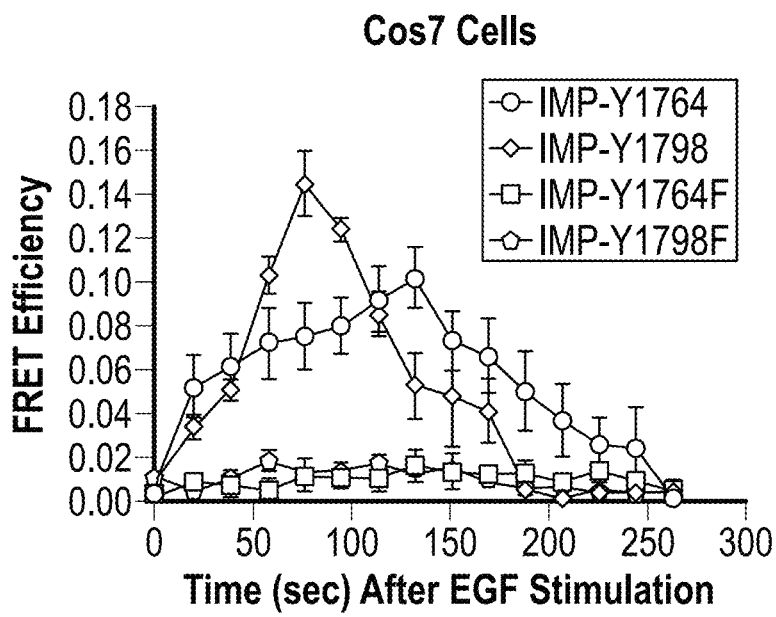
Figure 2D:
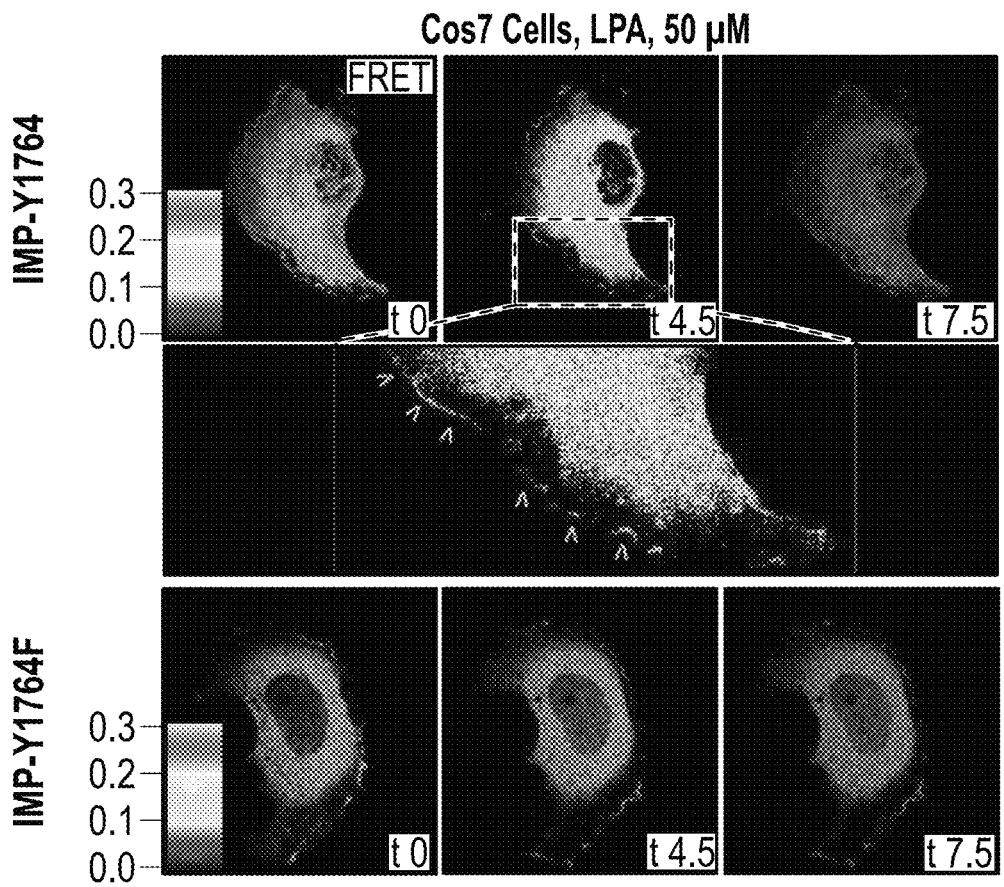
Figure 2E:
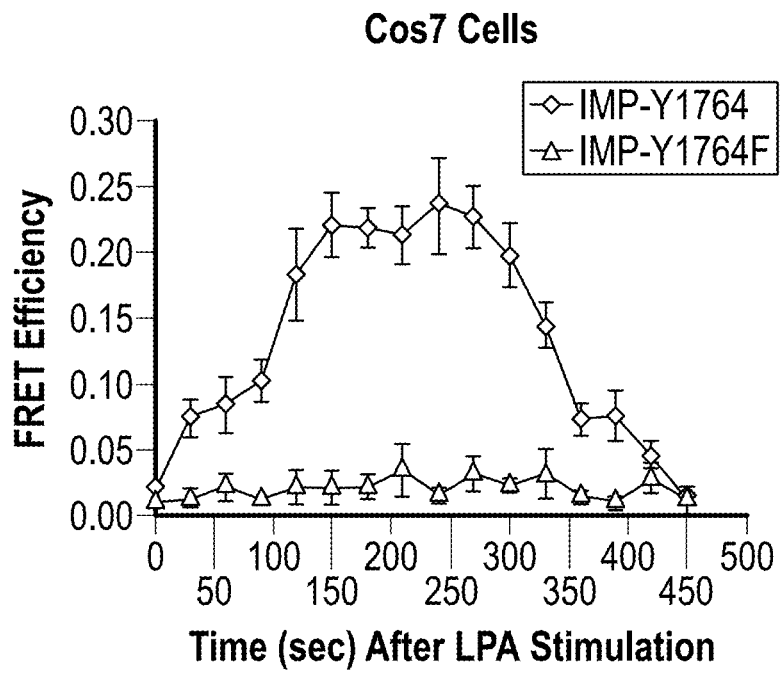
Figure 2F:
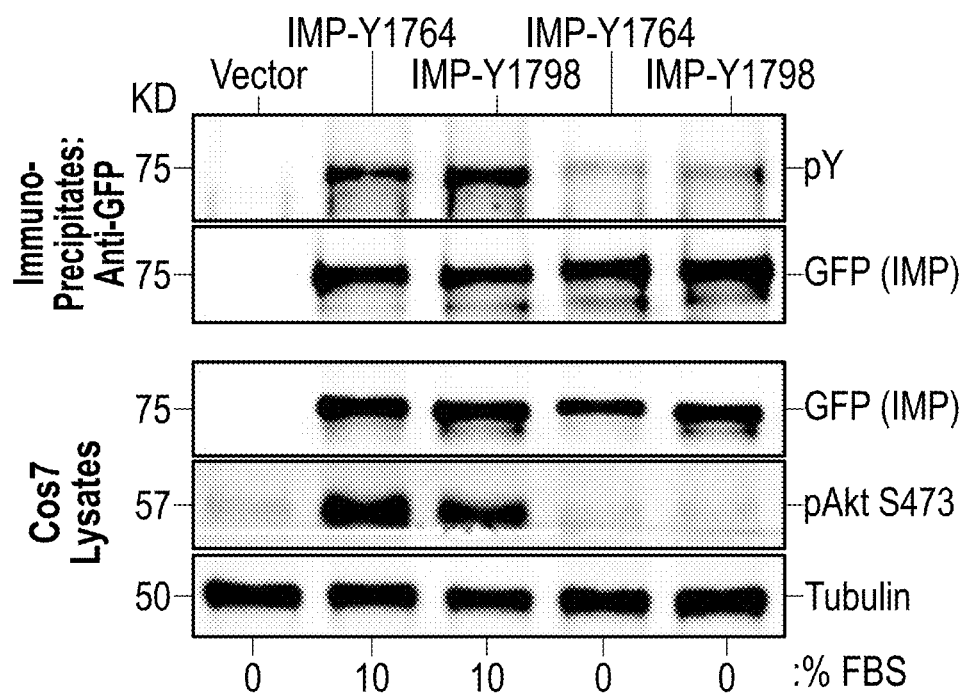
Figure 2G:
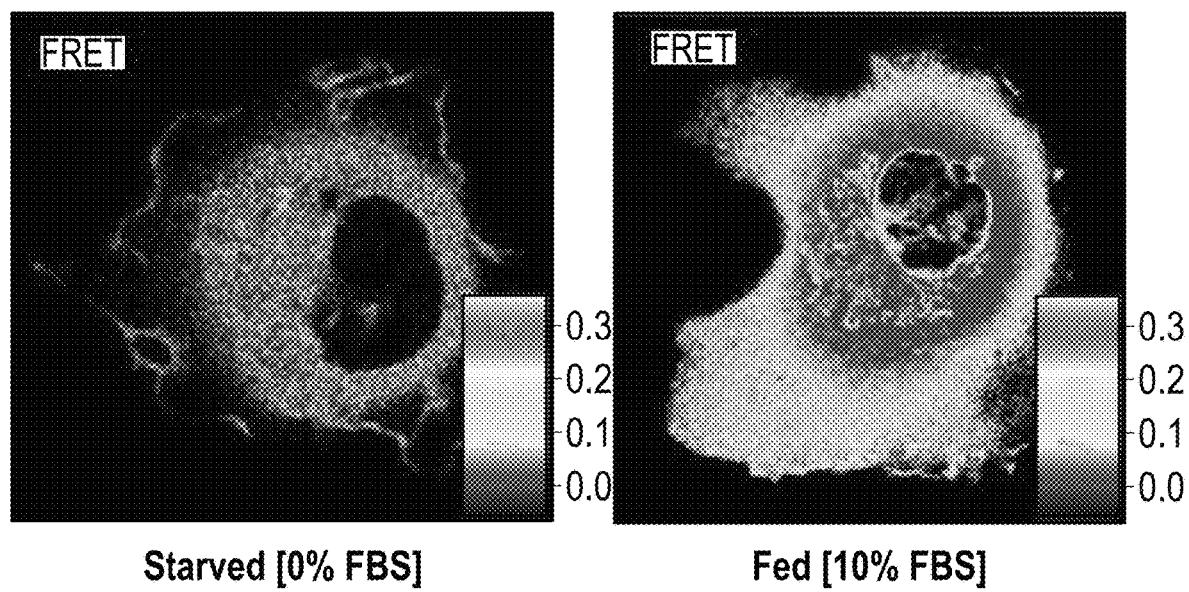
Figure 2H:
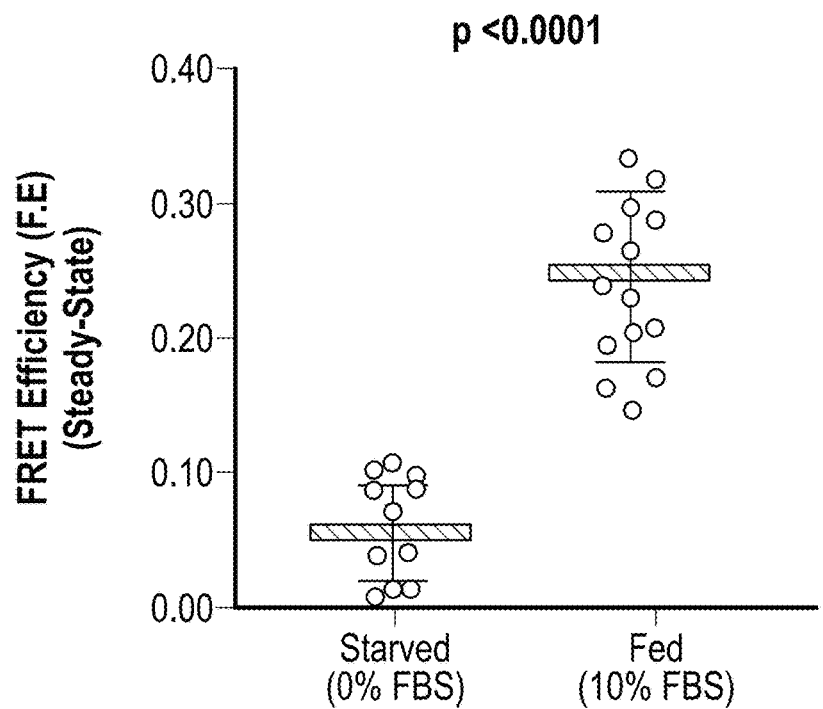
Figure 2I:
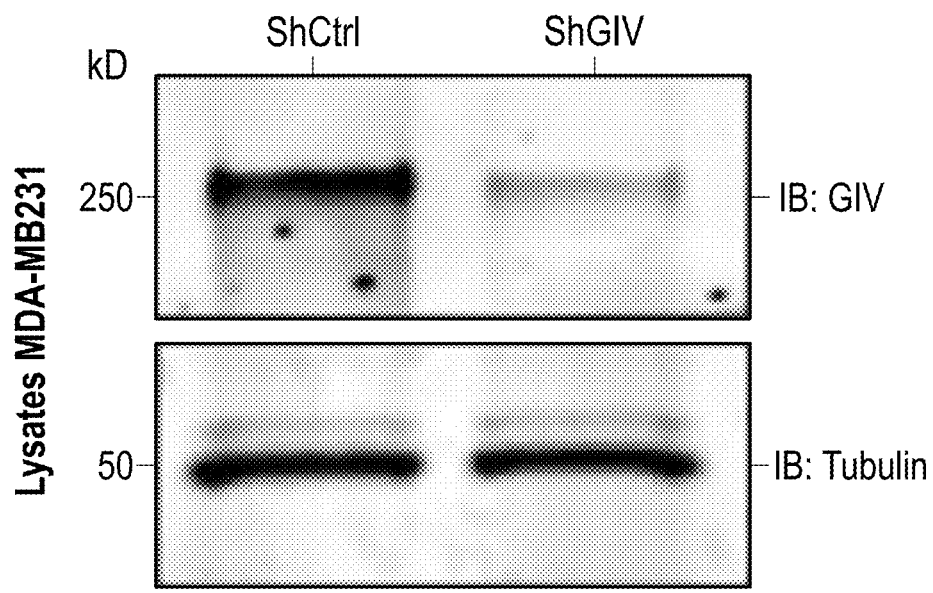
Figure 2J:
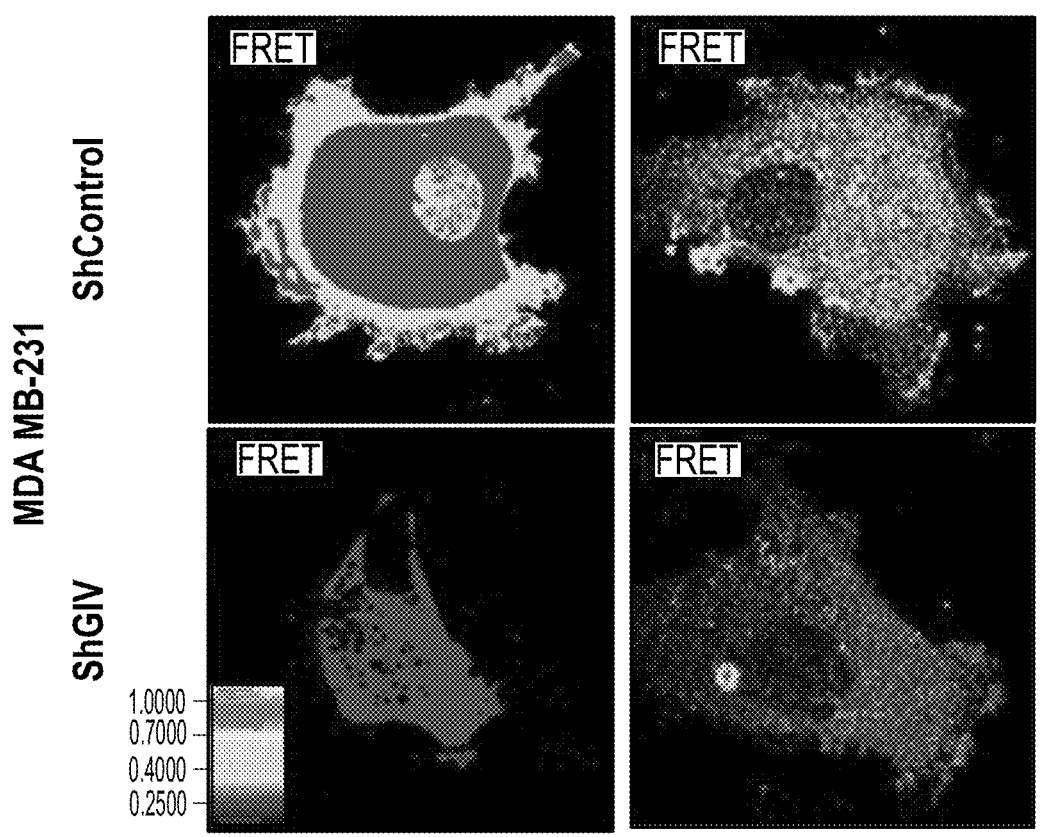
Figure 2K:
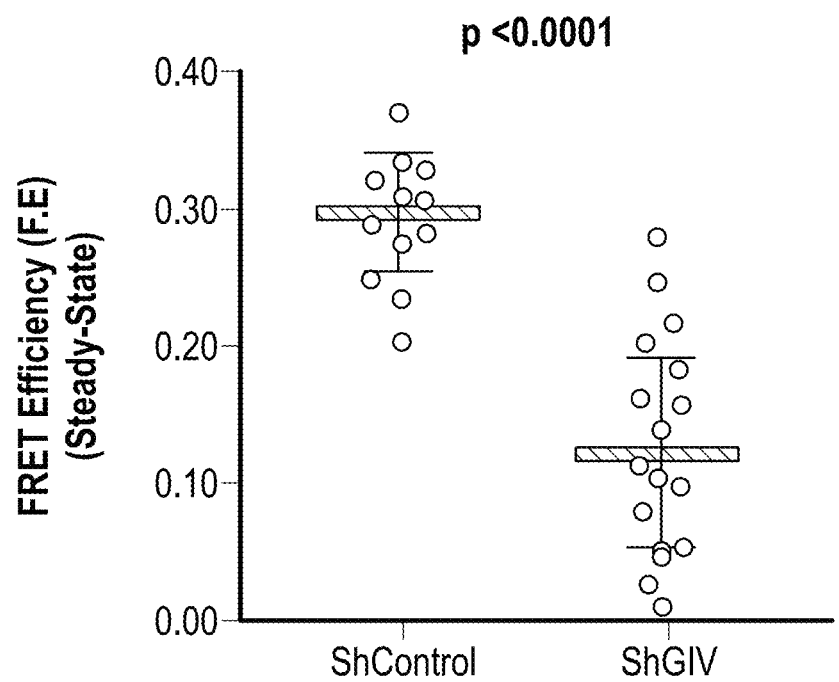

These probes were then validated in live cells to determine if ligand-induced tyrosine phosphorylation was also accompanied by intramolecular folding and FRET. FRET signals were analyzed exclusively at the PM because Class IA PI3Ks activated by tyrosine phosphorylated GIV transduce signals primarily by phosphorylating phosphatidylinositol-4,5-bisphosphate (PIP2) at the PM (41), and because tyrosine phosphorylation of GIV [as determined by immunofluorescence using anti-pYGIV antibody (42)] coincided temporally and spatially with the activation of PI3K [as determined using the fluorescent reporter, YFP-tagged PH-domain of Akt (35)] on microdomains at the PM (FIG. 2A). These temporal and spatial patterns were reproduced using IMP probes in living cells responding to either EGF (FIGS. 2B and 2C) or LPA (FIGS. 2D and 2E). Regardless of the pathway activated, FRET was observed at the PM within 2-2.5 min for both IMP-1764 and IMP-1798, albeit with a few notable differences. While FRET at the PM was transient in the case of growth factors, a more delayed (peak 4.5 min) and sustained response was seen in the case of LPA. These findings are consistent with the differential kinetics of Akt activation downstream, i.e., Akt phosphorylation typically peaks at 5 min after stimulation with growth factors, but at 15 min after stimulation of GPCRs (43). No FRET was observed when each IMP was substituted in the above assays with its non-phosphorylatable YF counterpart, indicating that ligand-stimulated tyrosine phosphorylation of GIV is essential for gaining FRET in each instance. Furthermore, compared to starved (0% FBS) cells, increased ambient signals in serum-fed cells (10% FBS) was accompanied by a higher steady-state probe phosphorylation (FIG. 2F) and FRET efficiency (F.E) (FIGS. 2G and 2H), indicating that IMPs can detect ambient multi-receptor driven signal flow at a steady-state without the need to acutely activate a given receptor/pathway. Furthermore, depletion of GIV in MDA-MB-231 cells, which require GIV for their ability to form lung metastases when xenografted in nude mice (44), was accompanied by a reduction in F.E (FIGS. 2I and 2K). The IMPs are the minimal platforms that can measure the timing, intensity and location of functional phosphorylation of GIV in living cells at steady-state.

Figure 3D:
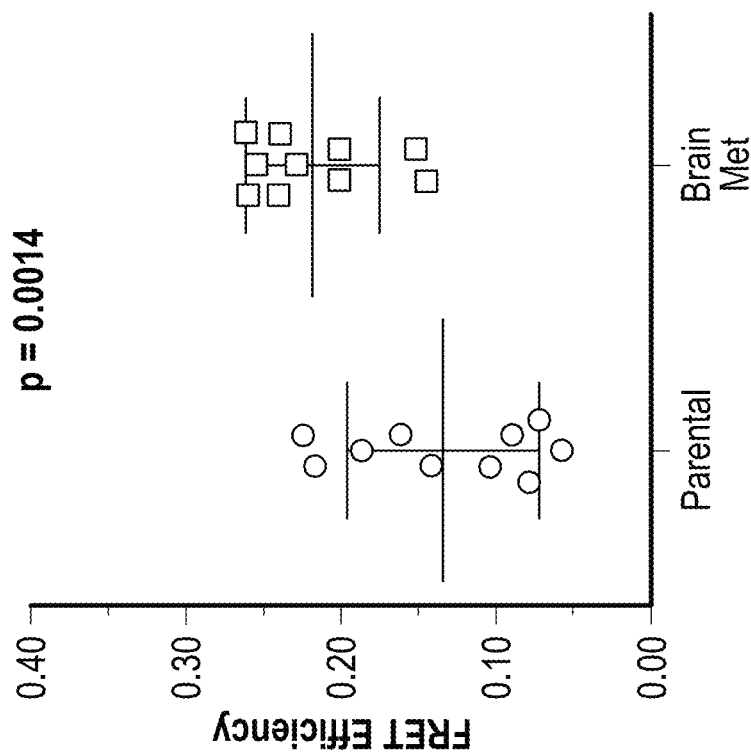
Figure 3D:
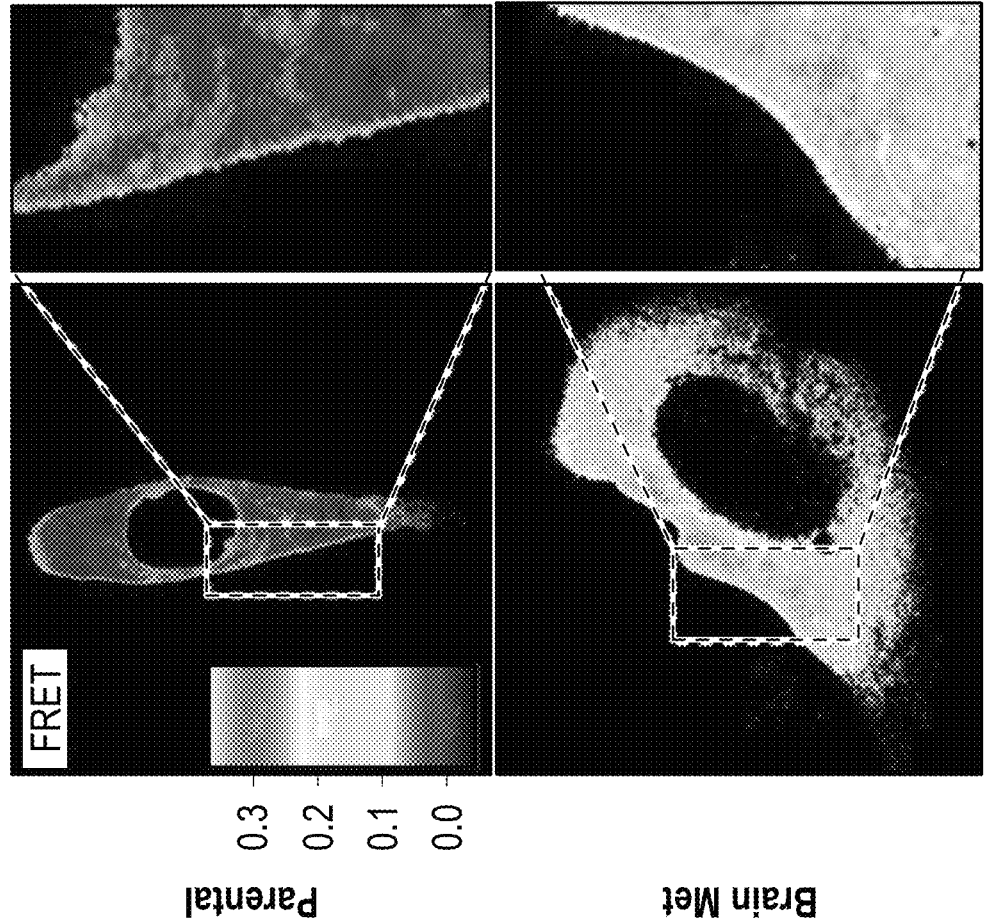
Figure 3E:
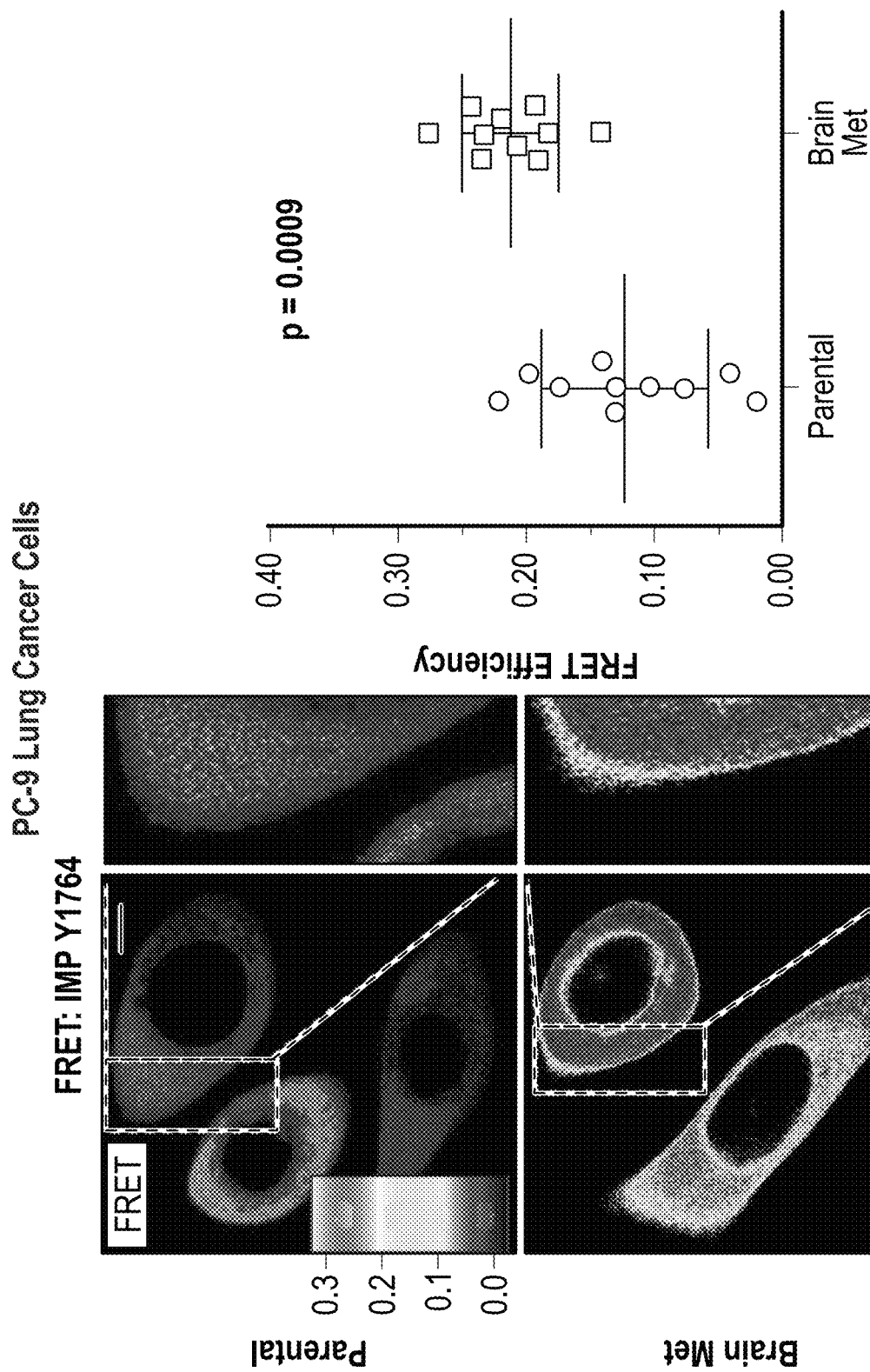
Figure 3F:
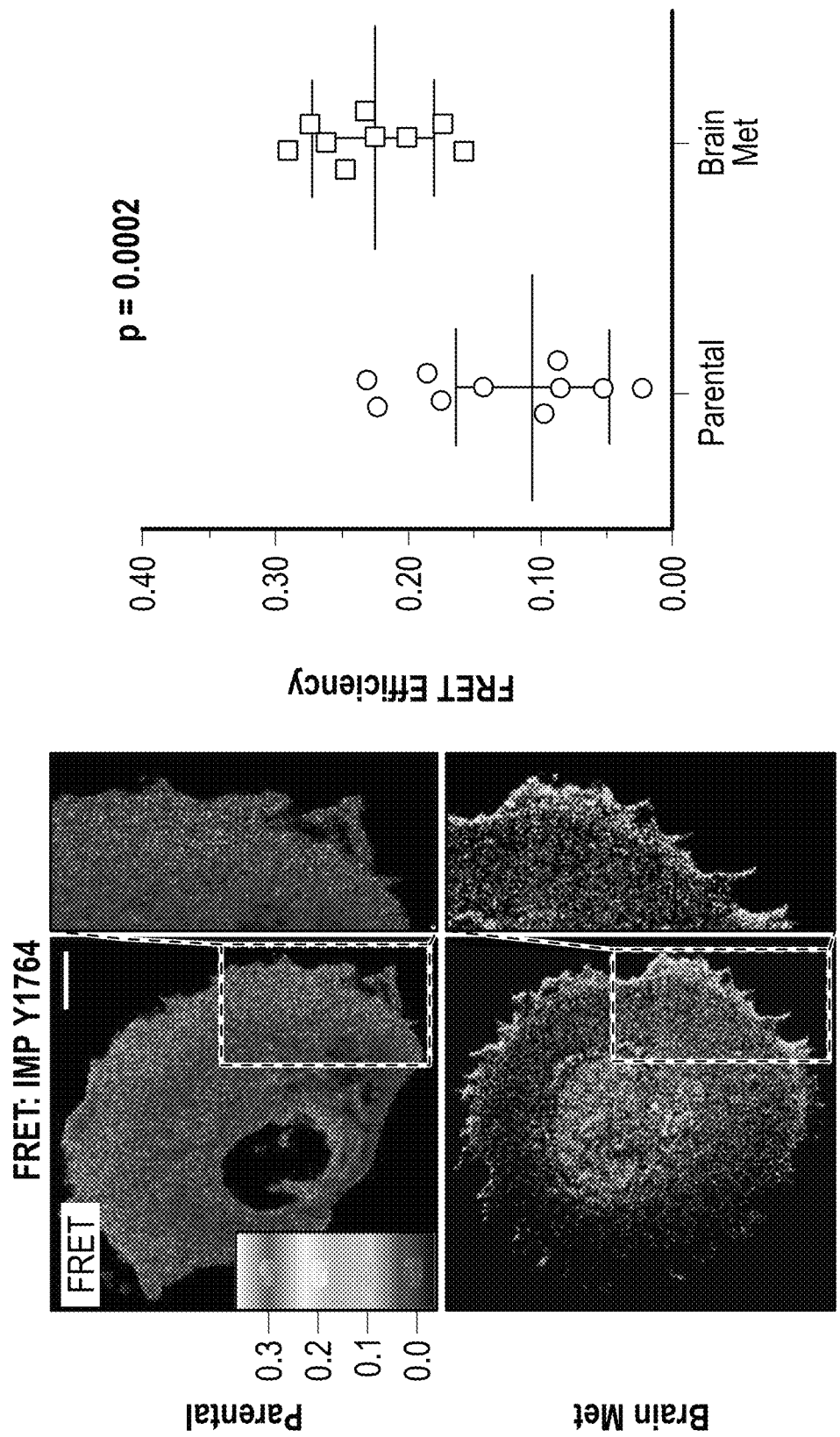
Figure 3G:
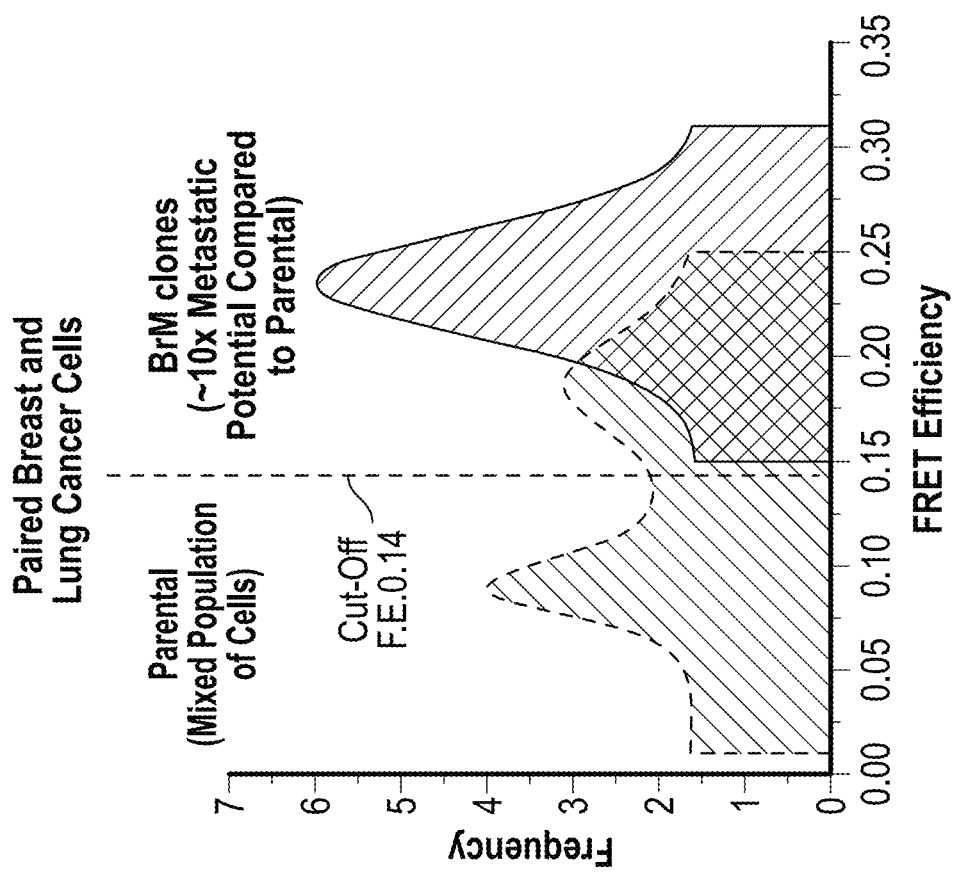
Figure 6A:
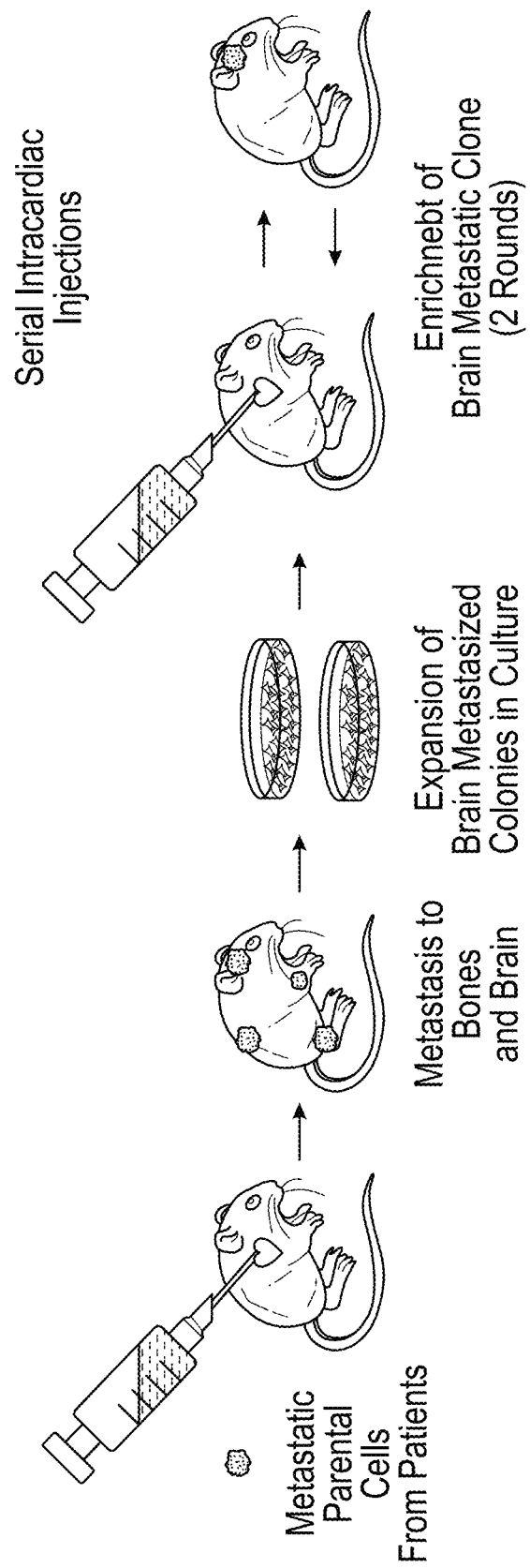
Figure 10:
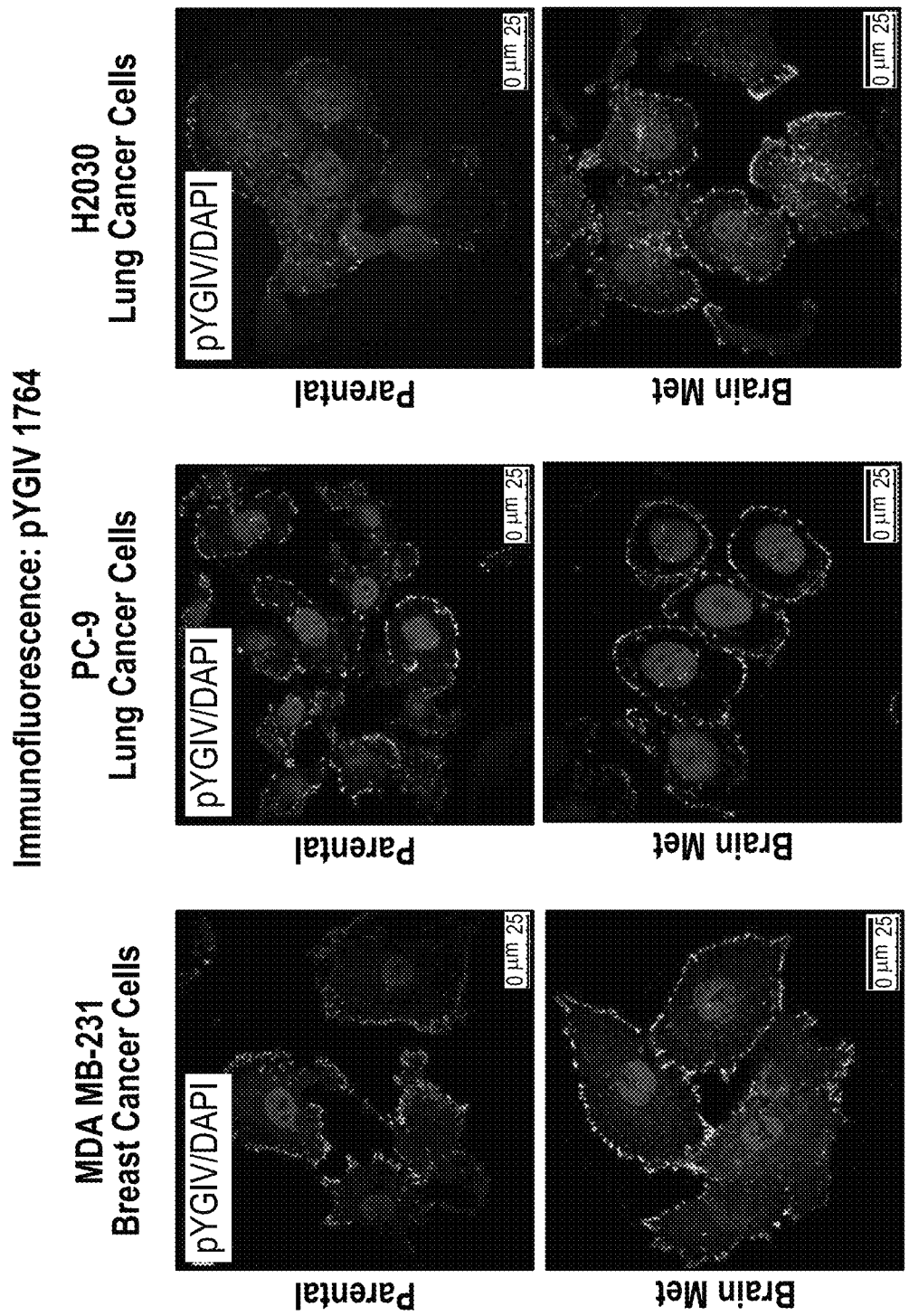
FIG. 10 shows tyrosine phosphorylation of GIV is indistinguishable among paired primary and BrM breast and lung cancer cells by Immunofluorescence. PC-9, H2030, MDA-MB-231 primary and their BrM counterparts were fixed, stained for tyrosine phosphorylated GIV (pYGIV; red greyscales) and DAPI (nucleus; blue greyscales) and analyzed by confocal microscopy. Representative images of cells are shown. Although cell-to-cell heterogeneity in intensity of staining was encountered, no discernable differences in patterns of staining was observed between the parental and BrM clones. Bar=10 μm.
Figures 11A, 11B:
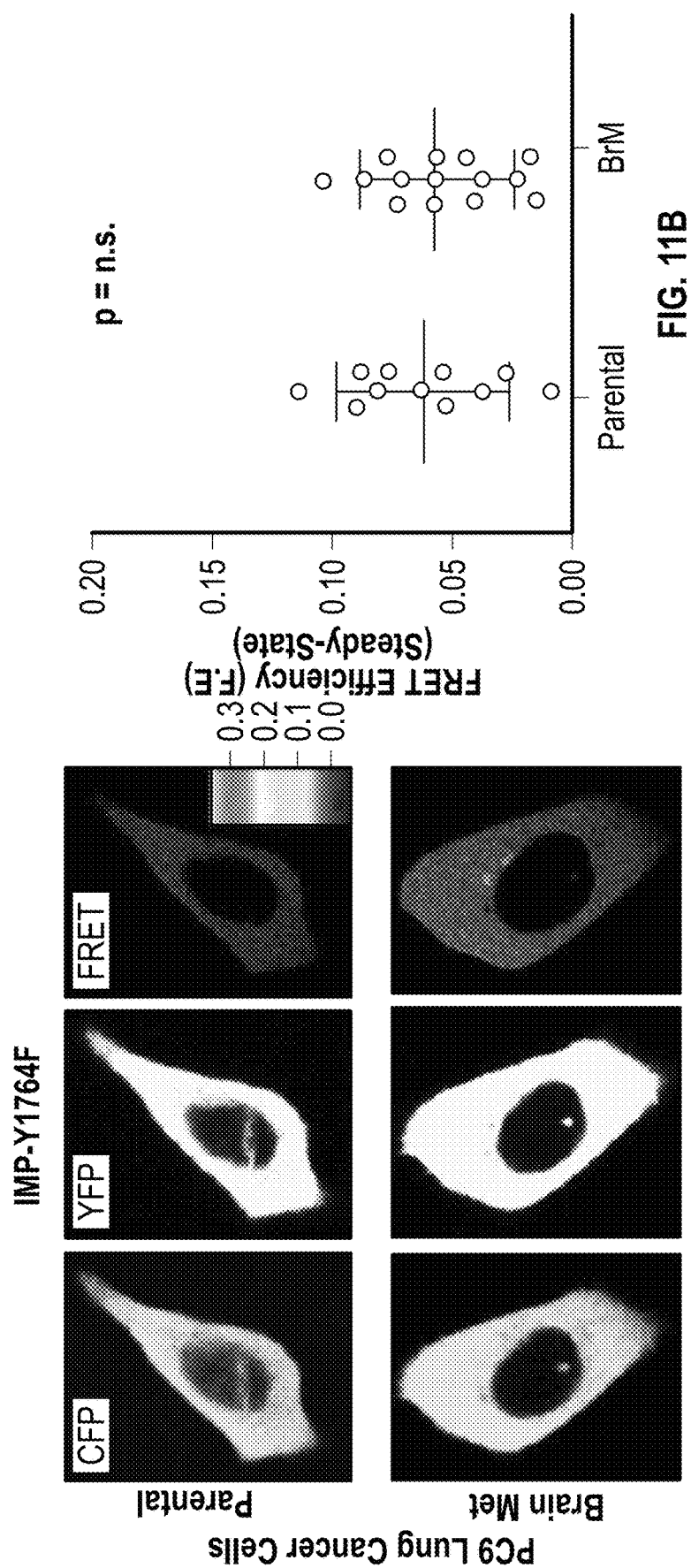
FIGS. 11A-11E show control experiments that show the specificity of IMP probes to detect meaningful, context-dependent signals.
Figures 11C, 11D:
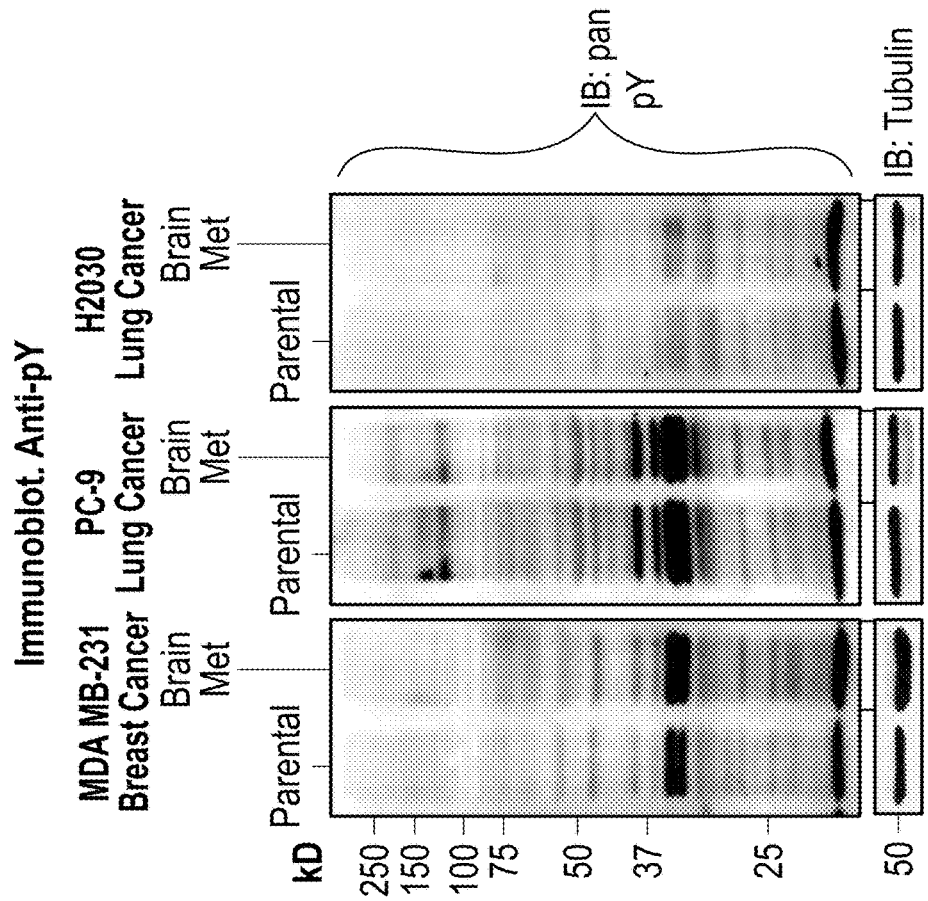
Figure 11E:
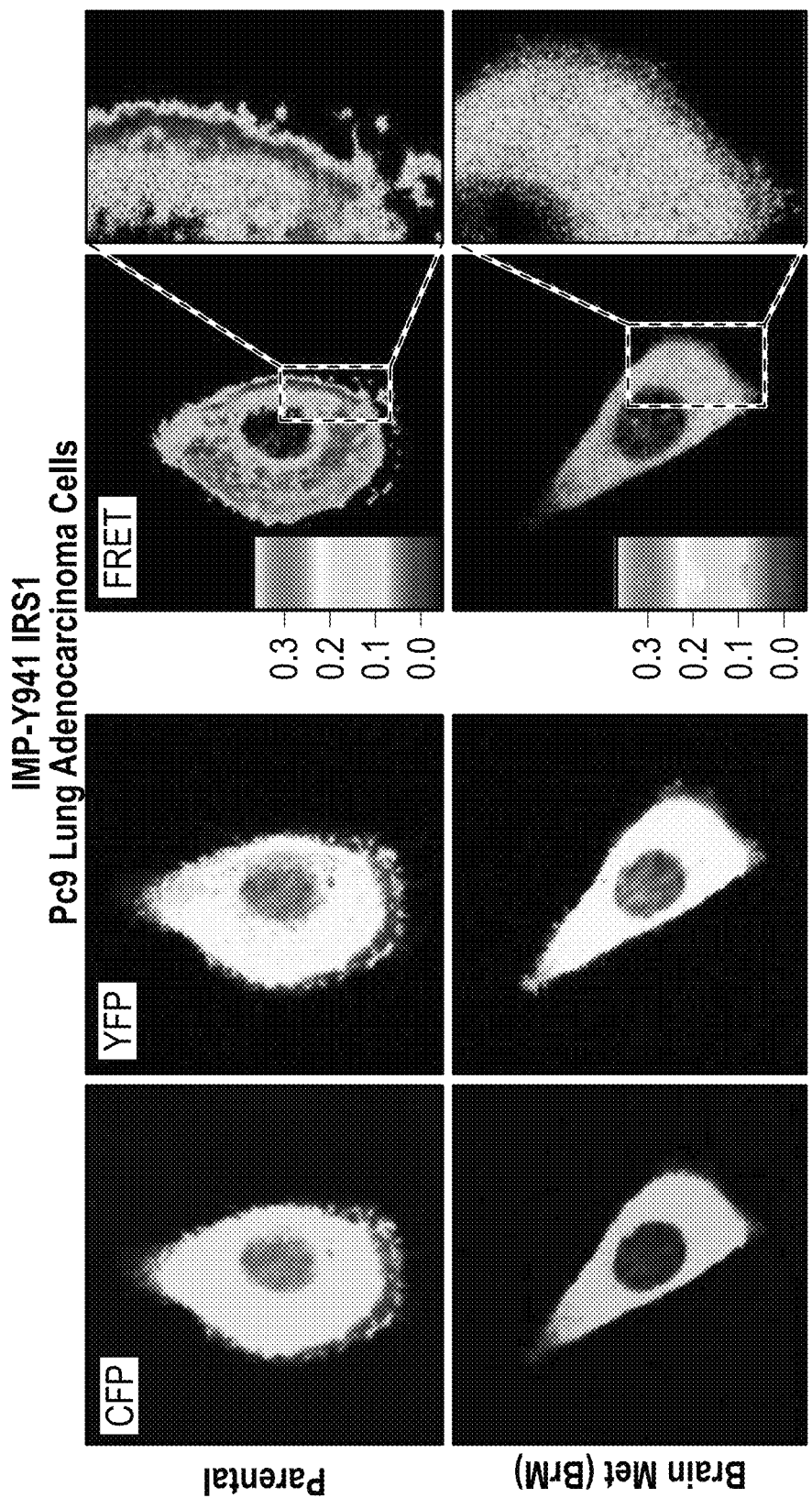
Figure 11F:
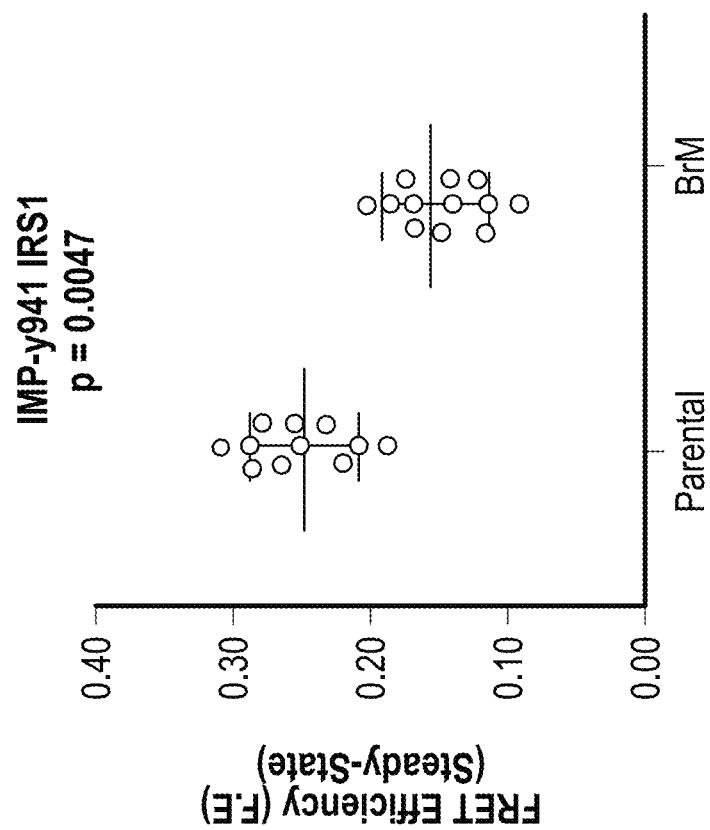

The ability of the IMPs to measure steady-state ambient multi-receptor signaling via the GIV-PI3K axis can serve as a readout of the aberrant prometastatic signaling during the acquisition of metastatic potential was investigated. It was predicted that such measurement should come with three key advantages—1) Eliminate the need to know to which upstream pathways (drivers vs hitchhikers) a given tumor is addicted; 2) Avoid perturbing the intrinsic pathologic pathways with extrinsic ligands that introduce undesired bias; and 3) Ensure continued usefulness despite changes in tumor dependency on a given pathway, as during metastatic progression or development of drug resistance. To test these predictions, the IMPs were validated using three well characterized metastatic breast and lung adenocarcinoma cell lines, MDA-MB-231, PC-9 and H2030, and their corresponding highly metastatic subclones (BrM) that were selected in mice and display ~10-fold enhanced ability to metastasize to the bone and brain (45, 46) (FIG. 6A). Despite their diverse genetic backgrounds (FIG. 6B), all BrM clones consistently displayed one common feature compared to their parental counterparts: higher Akt activity (FIG. 3A-3C), whereas the patterns of immunofluorescence staining for tyrosine-phosphorylated GIV (pY1764GIV) showed only minor differences (FIG. 10). Using the IMP-Y1764 probe, it was found that the steady-state F.E. in individual cells varied over a range in these cells (FIG. 3D-3F); the variance is in keeping with the expected heterogeneity in metastatic potential within a given population of cells (2). However, the mean F.E. of the BrM cells were consistently ~2-fold higher than their parental counterparts (FIG. 3D-3F). Gaussian fits of the histograms of the FRET efficiencies of individual cells from these paired cell lines revealed that parental cells were more heterogeneous (wider spread of F.E with two peaks), whereas their BrM counterparts were less heterogeneous (a single narrow peak), and that a subset of parental cells behaved just like BrM cells (partial overlap between second peak of parental cells and the BrM cells). Because a feature of quantitative single-cell imaging is to allow the measured entity to be quantified by choosing a cut-off value for the histogram of overlap integrals, the data in FIG. 3G suggests that 0.14 is a reasonable cut-off; values below or above 0.14 would indicate that the potential for metastasis is low or high, respectively. Because some cells in the parental population displayed F.E. >0.14 and overlapped with BrM cells, these findings validate that single-cell steady-state F.E. measured using IMP-Y1764 can detect those subpopulations of parental cells that have acquired the metastatic potential, but risk being obscured by averaging (Mean F.E. of parental cells=0.125, which is below the 0.14 cutoff). It was also confirmed that the high F.E. observed in BrM cells required a phosphorylatable tyrosine within the IMP-Y1764 probe (FIG. 11A-11B) but did not merely reflect a generalized hyperactivation of tyrosine-based signaling (FIG. 11C). Furthermore, replacement of the GIV sequence in IMP-Y1764 with a stretch of residues that flank Y941 on IRS1 (FIG. 11D) which is phosphorylated by multiple RTKs and binds p85α(PI3K) (18), abolished the probe's ability to distinguish parental from their BrM counterparts (FIGS. 11E-11F). These results demonstrate the functional specificity of tyrosine phosphorylated GIV as a portal for integration of prometastatic PI3K signaling downstream of multiple receptors; not reproducible by other phosphotyrosine substrates that also serve as ligand for p85α(PI3K).

Figures 12A, 12B:
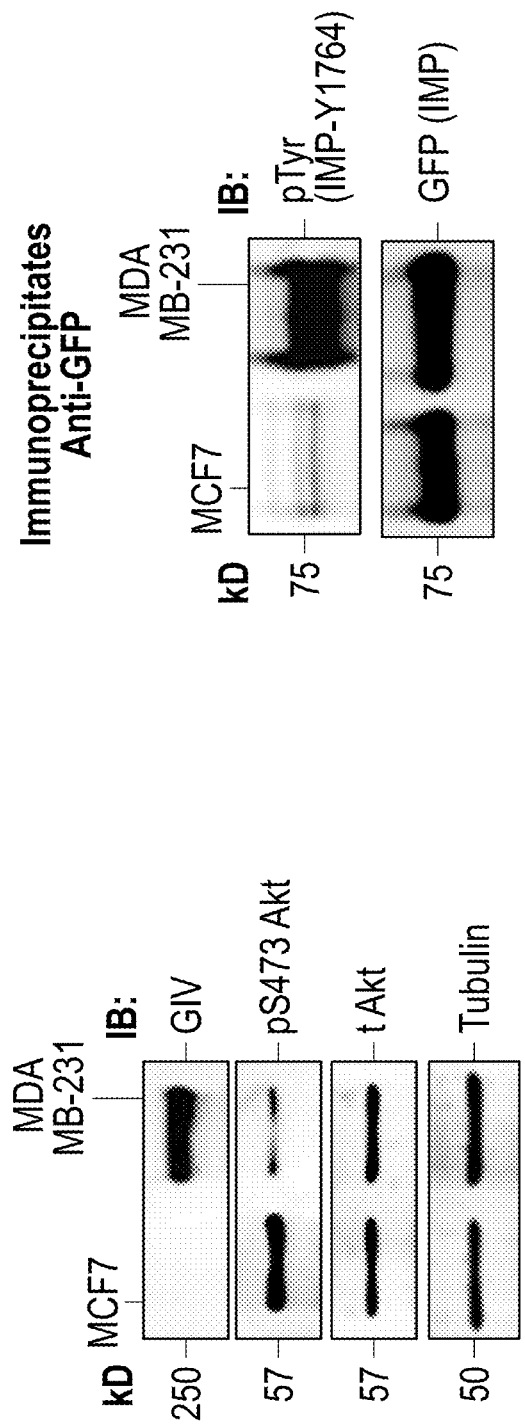
FIGS. 12A-12D show IMP sensors can distinguish between MCF7 and MDA-MB-231 cells, two breast cancer cell lines with contrasting metastatic proclivities.
Figure 12C:
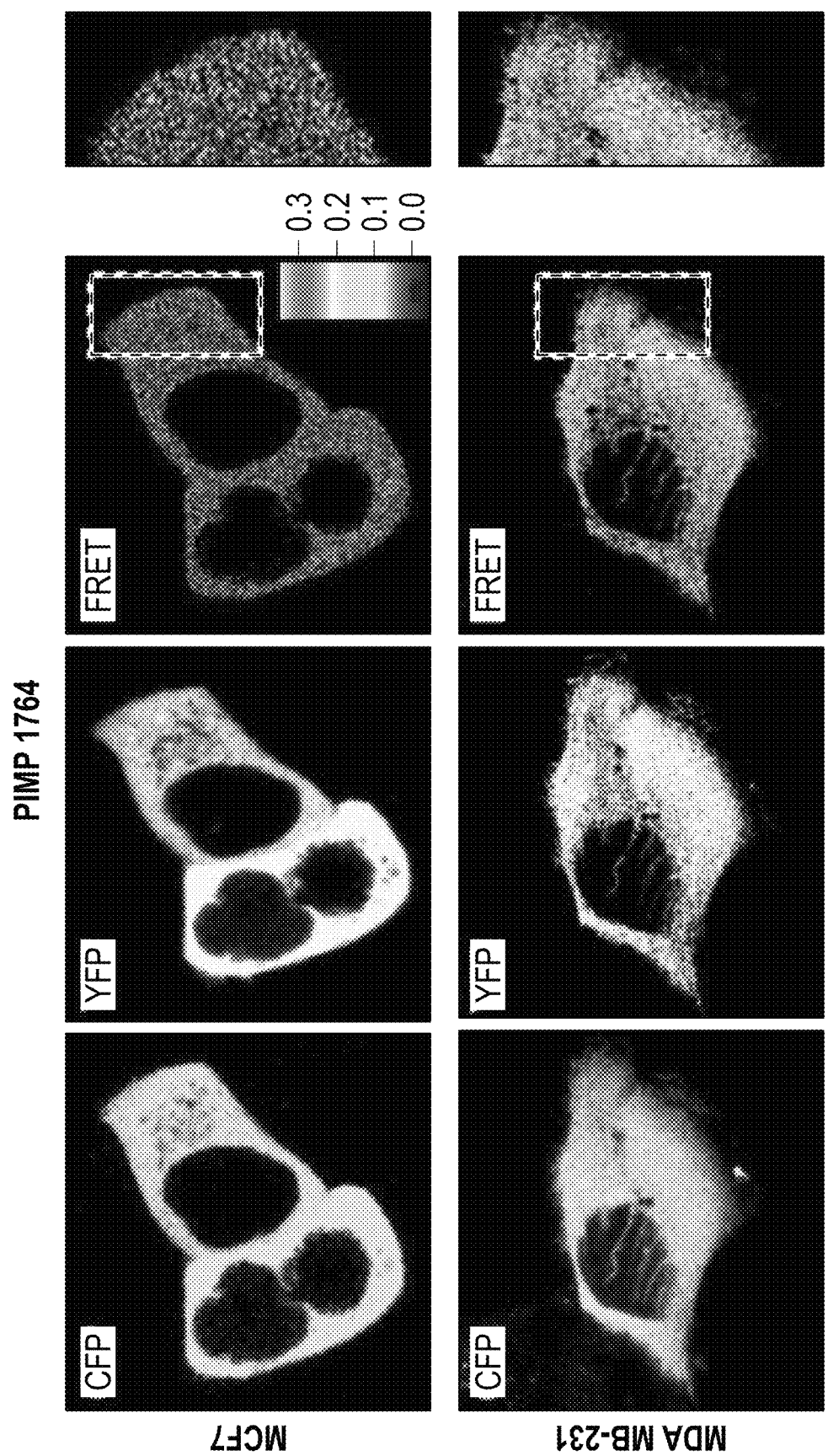
Figure 12D:
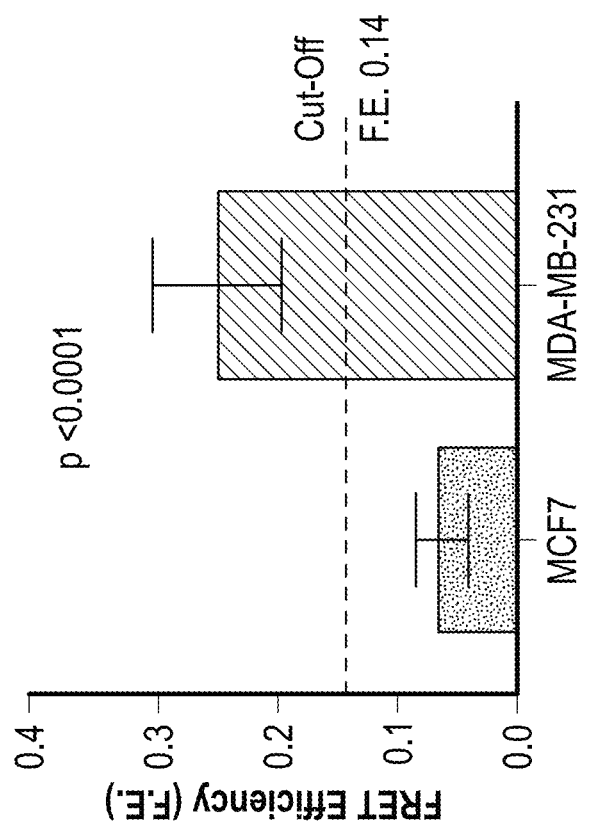

The ability of the IMP-Y1764 probe to distinguish between the MCF7 and MDA-MB-231 cells was interrogated; 2 lines frequently studied for their contrasting metastatic potential (14). MDA-MB-231 cells express full-length GIV (FIG. 12A) and metastasize at a frequency approaching ~100% (100% to LN, 40-70% to lungs), whereas the MCF7 cells do not metastasize (47-49). It was found that the extent of phosphorylation of IMP-Y1764 (FIG. 12B) and the mean F.E. in MCF7 (0.06±0.01) and MDA-MB-231 cells (0.24±0.05) (FIGS. 12C-12D) were in keeping with their contrasting metastatic potentials. That F.E. in MCF7 cells was low, despite high levels of Akt phosphorylation (FIG. 12A) indicates that F.E of IMP-Y1764 can distinguish prometastatic GIV-PI3K-Akt signals from other Akt signals.

Figure 3H:
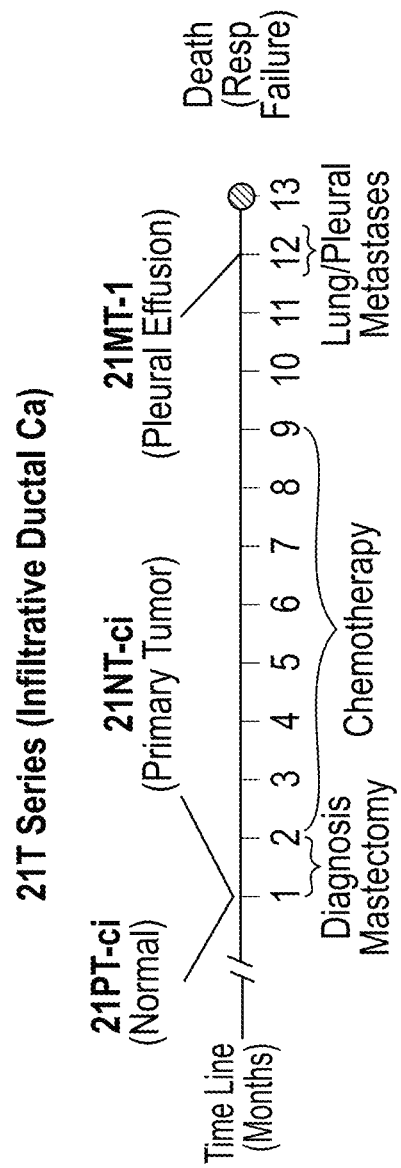
Figure 3I:
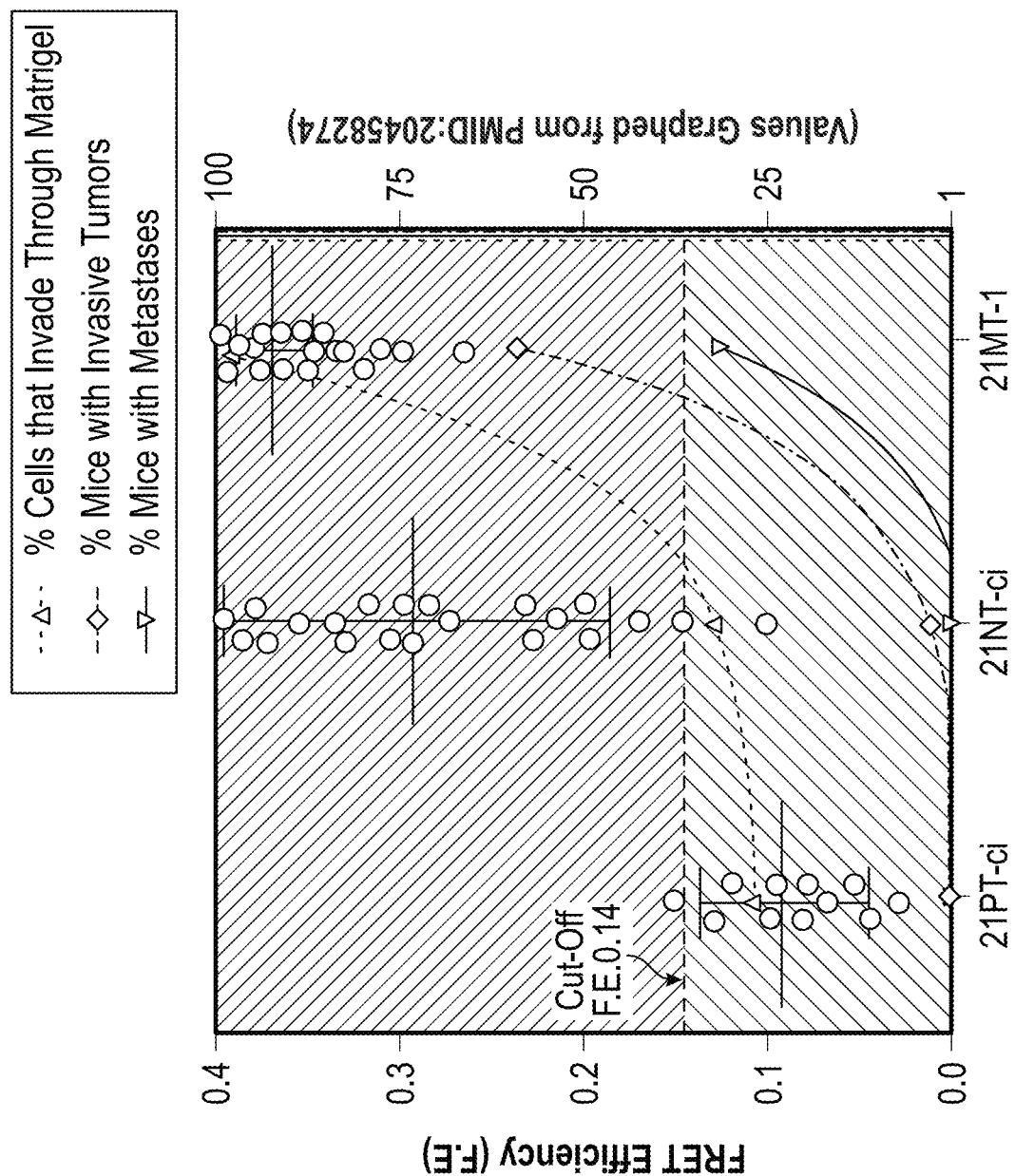
Figure 13A:
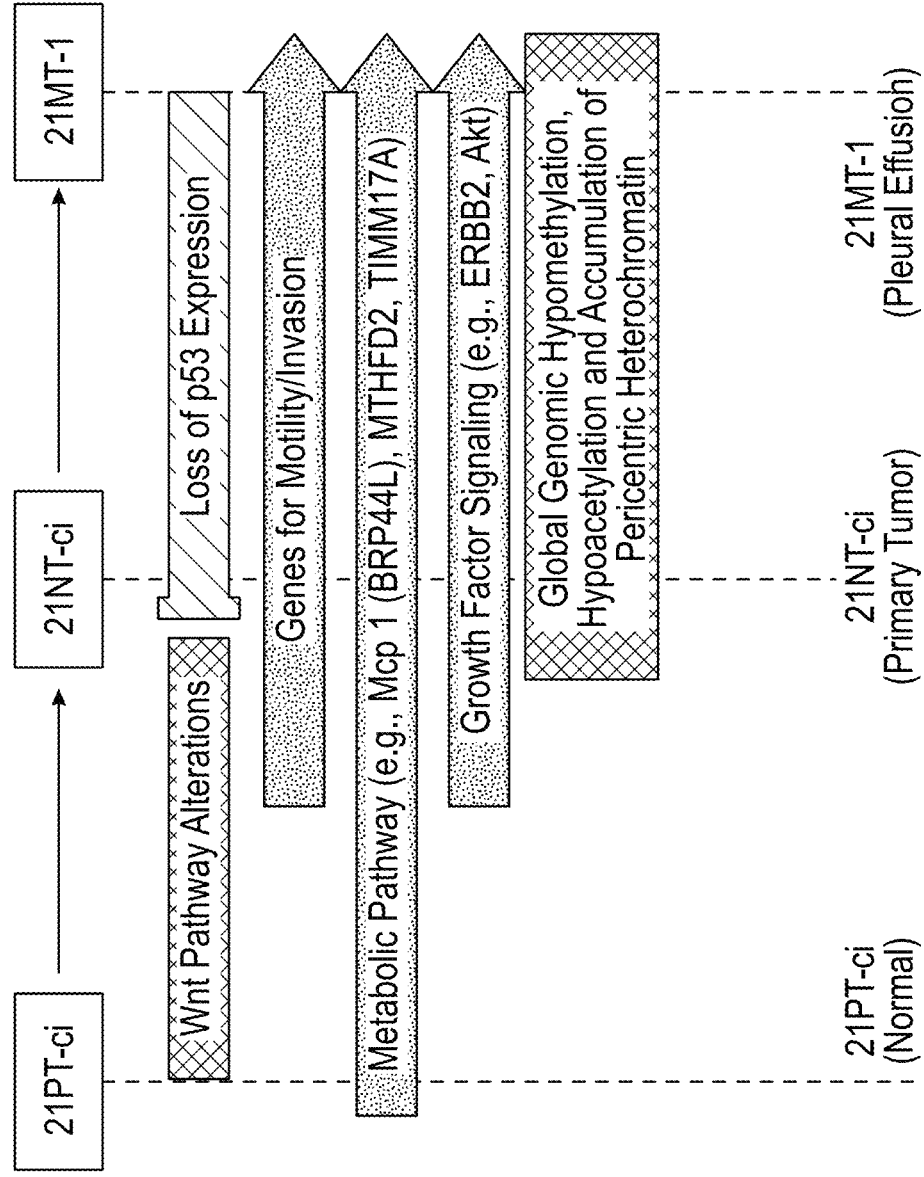
FIGS. 13A-13B depict the IMPY1764 sensor retains its ability to detect metastatic proclivity despite the evolving genetic and epigenetic shifts in tumor cells during the course of metastatic progression.
Figure 13B:
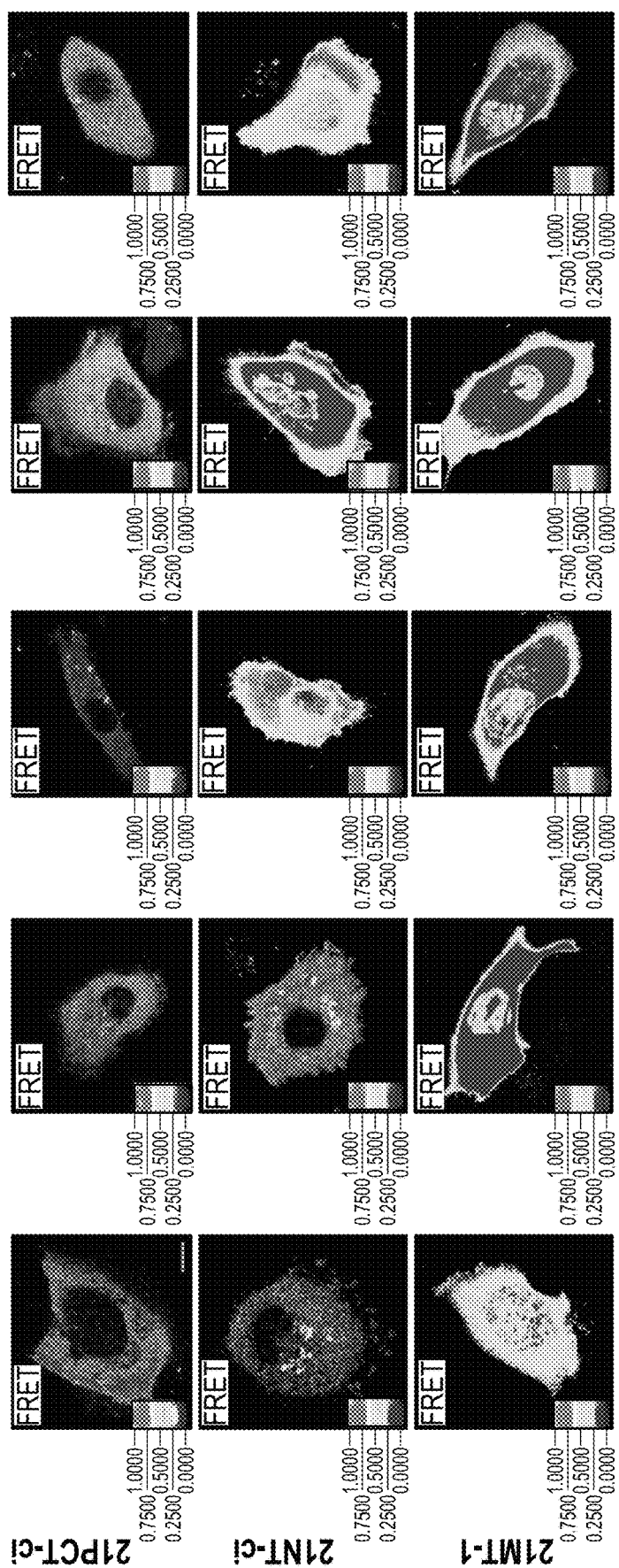
Figure 14:
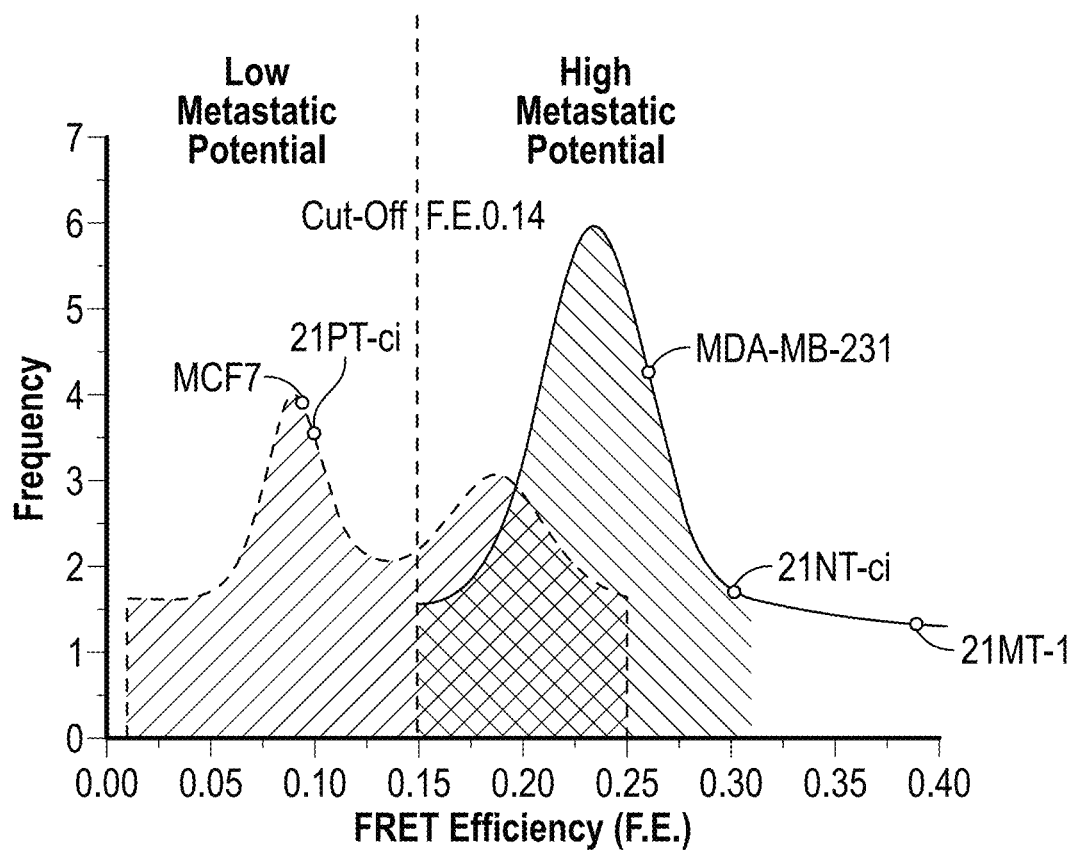
FIG. 14 depicts Gaussian fits of the cumulative histogram in FIG. 3g the position of various cell lines (mean FRET) studied in this work indicated on the Gaussian curve.

Whether the IMP-Y1764 probe retains its ability to detect the metastatic potential of tumor cells despite evolving signaling programs and tumor biology was investigated. Such evolution is encountered under two circumstances—1) during metastatic progression in humans, and 2) during the development of drug resistance. To study the first, the 21T lines that were derived from the same patient during breast cancer progression (50) (FIG. 3H) and display an array of changing epigenetic, proteomic and signaling programs during progressive acquisition of metastatic potential (FIG. 13A) were used. Enhanced Akt signaling during metastatic progression in 21T cells (51) has previously been shown to track well with increased expression of GIV mRNA and protein (49) as well as enhanced tyrosine phosphorylation of GIV at Y1764/98 (35). It was found that F.E using the IMP-Y1764 probe was low in normal (PT-ci; 0.08±0.01), but high in primary (NT-ci; 0.28±0.07) and metastasized (MT-1; 0.38±0.03) cells (FIGS. 3I and 13B), indicating that the probe could effectively categorize both NT-ci and MT-1 as cells with 'high' potential for metastasis regardless of the changes in tumor biology incurred during disease progression over 1 y and cytotoxic chemotherapy received by the patient (50). Furthermore, as in the case of MCF7 and MDA-MB-231 cells, the chosen cutoff F.E. of 0.14 was effective in accurately detecting the metastatic potential of 21T cells (FIG. 14).

Figures 4A, 4B, 4C:
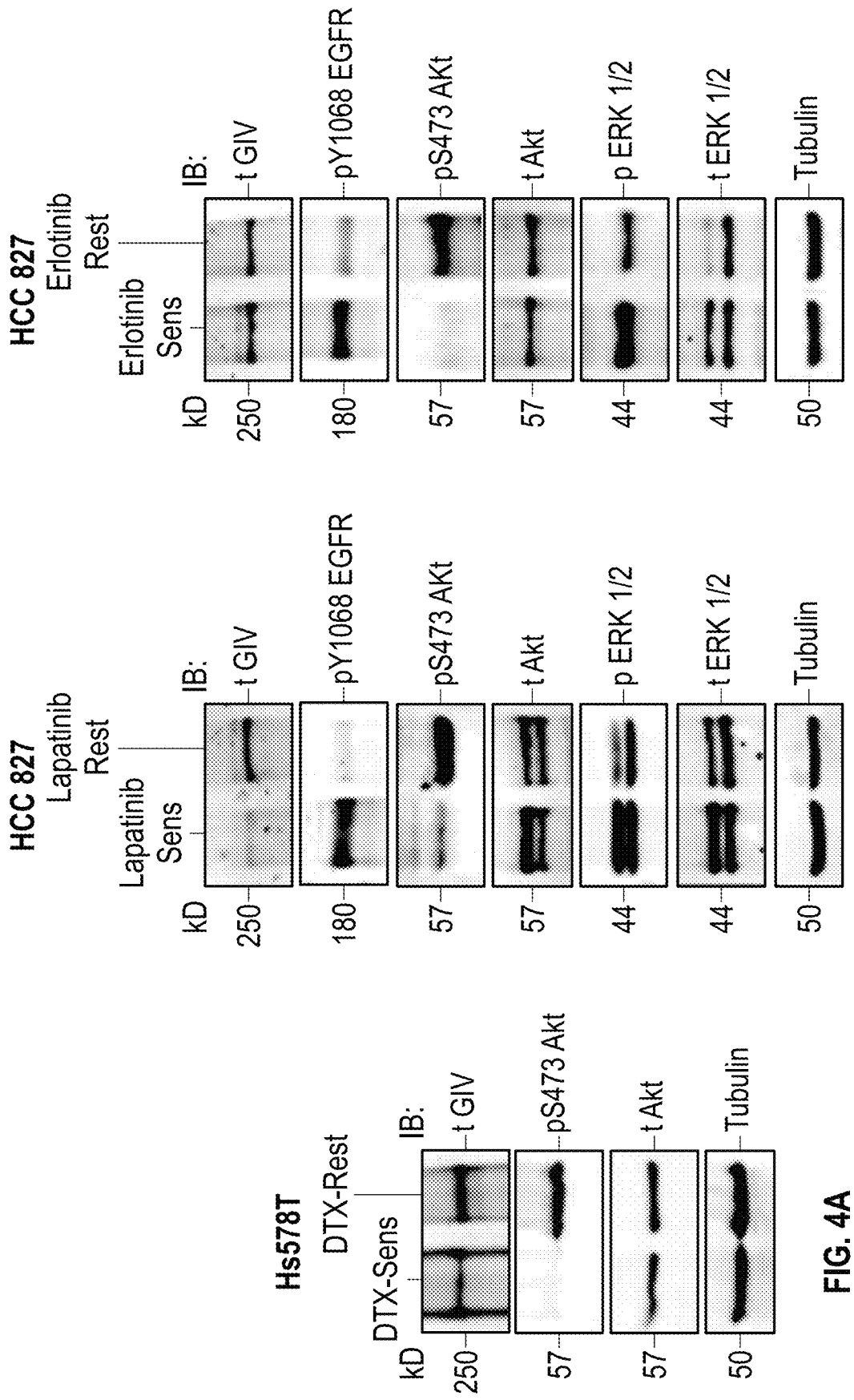
FIGS. 4A-4H provide a steady-state FRET imaging using IMP-Y1764 before and after the emergence of drug resistance.
Figure 4D:
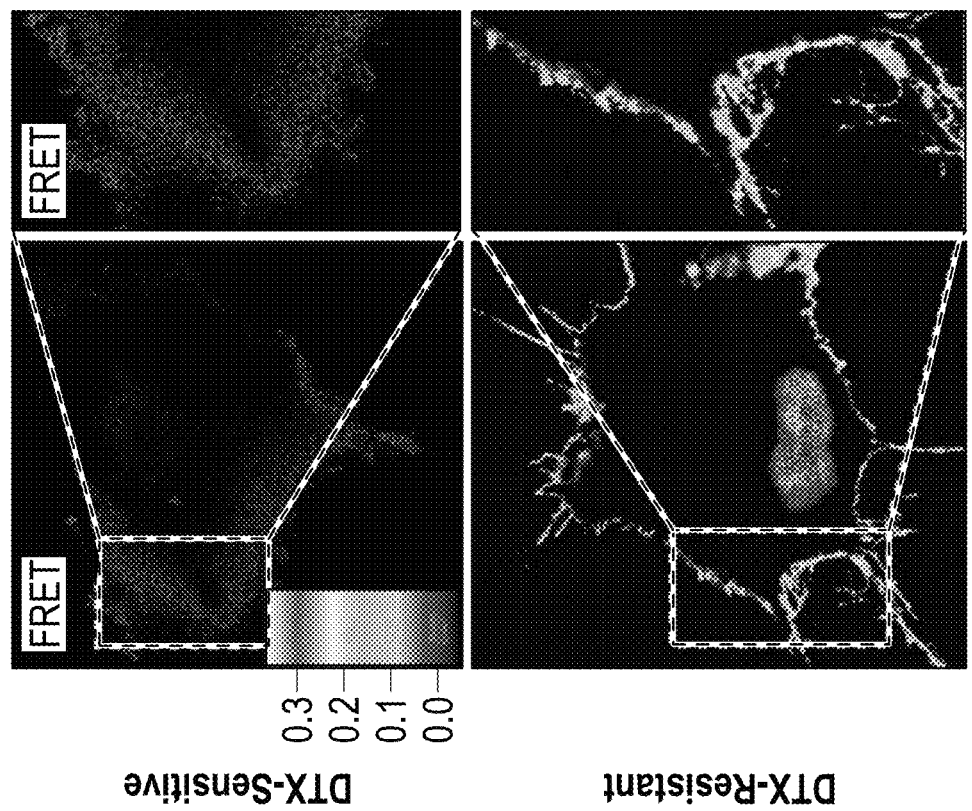
Figure 4E:
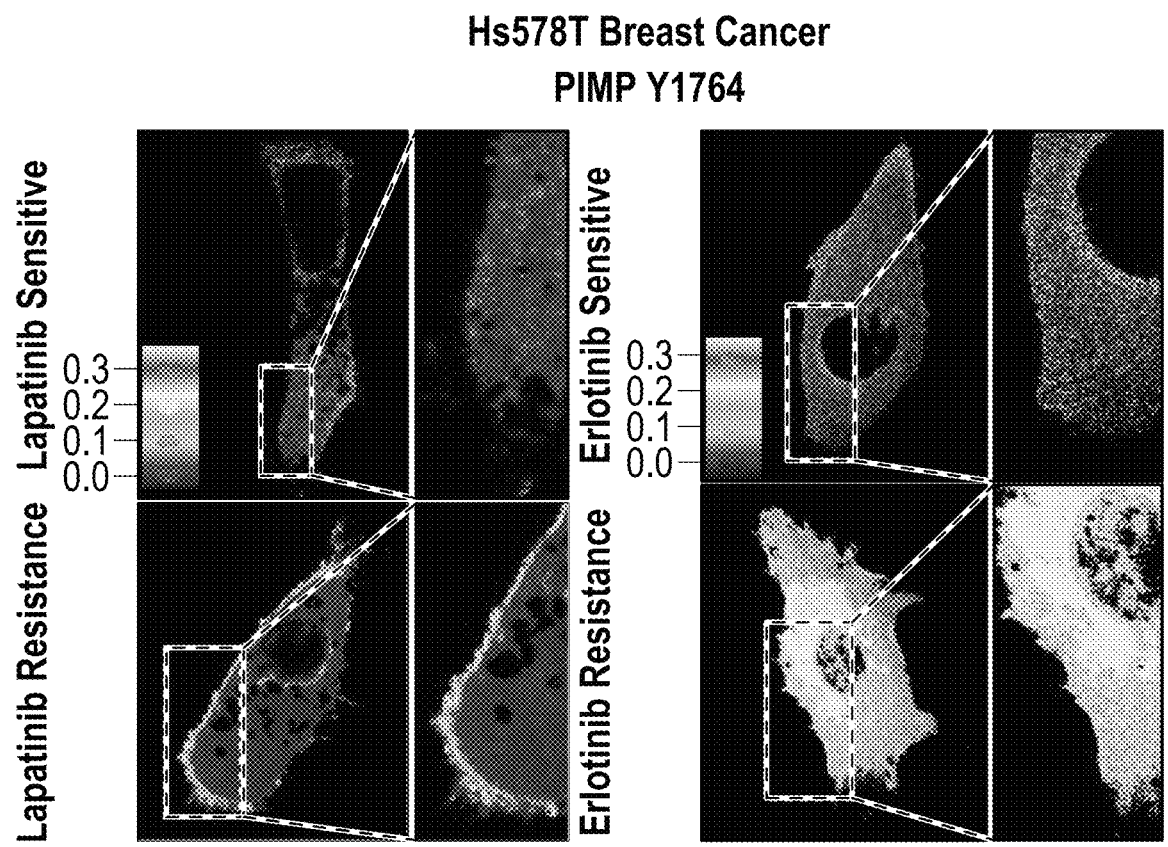
Figure 4F:
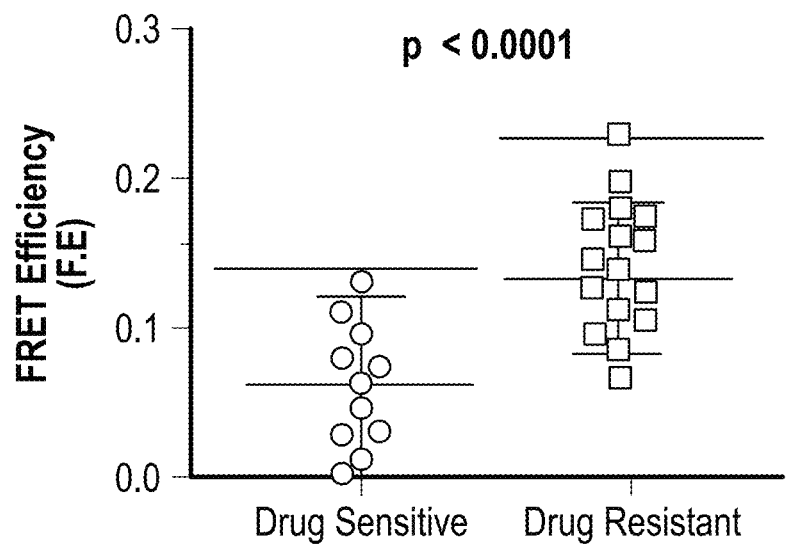
Figure 15B:
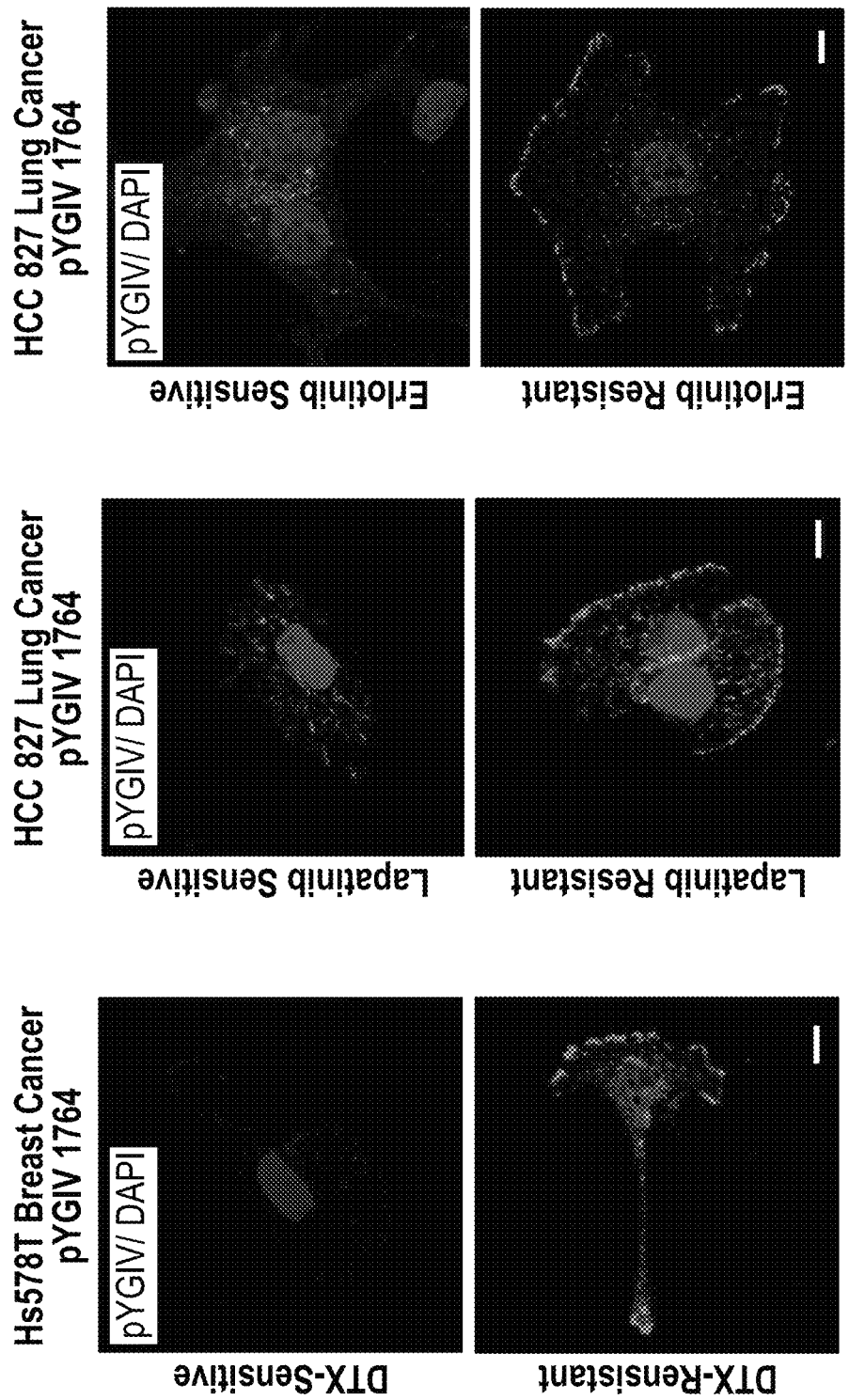

To study the impact of changing tumor biology during the acquisition of drug resistance, three breast and lung cancer lines (FIG. 15A, FIG. 4A-4C) with variable resistance to cytotoxic chemotherapy (docetaxel) or inhibitors of RTKs (Erlotinib and Lapatinib) were used. Compared to the sensitive clones, both pY1764GIV (FIG. 15B) and Akt phosphorylations (FIGS. 4A-4C) were consistently enhanced and their expressions were upregulated in their resistant counterparts. This is in keeping with the fact that invasiveness/EMT and sternness, two features of drug resistance are both modulated by GIV (52). The F.E measured using IMP-Y1764 were similarly elevated ~2-3 fold in the resistant clones (FIGS. 4D-4F), indicating that the probe accurately detected the acquisition of higher metastatic potential that coincides with drug resistance. Such detection was possible regardless of the unknown-unknowns of evolving tumor biology during the acquisition of resistance (FIG. 15A).

Figure 4G:
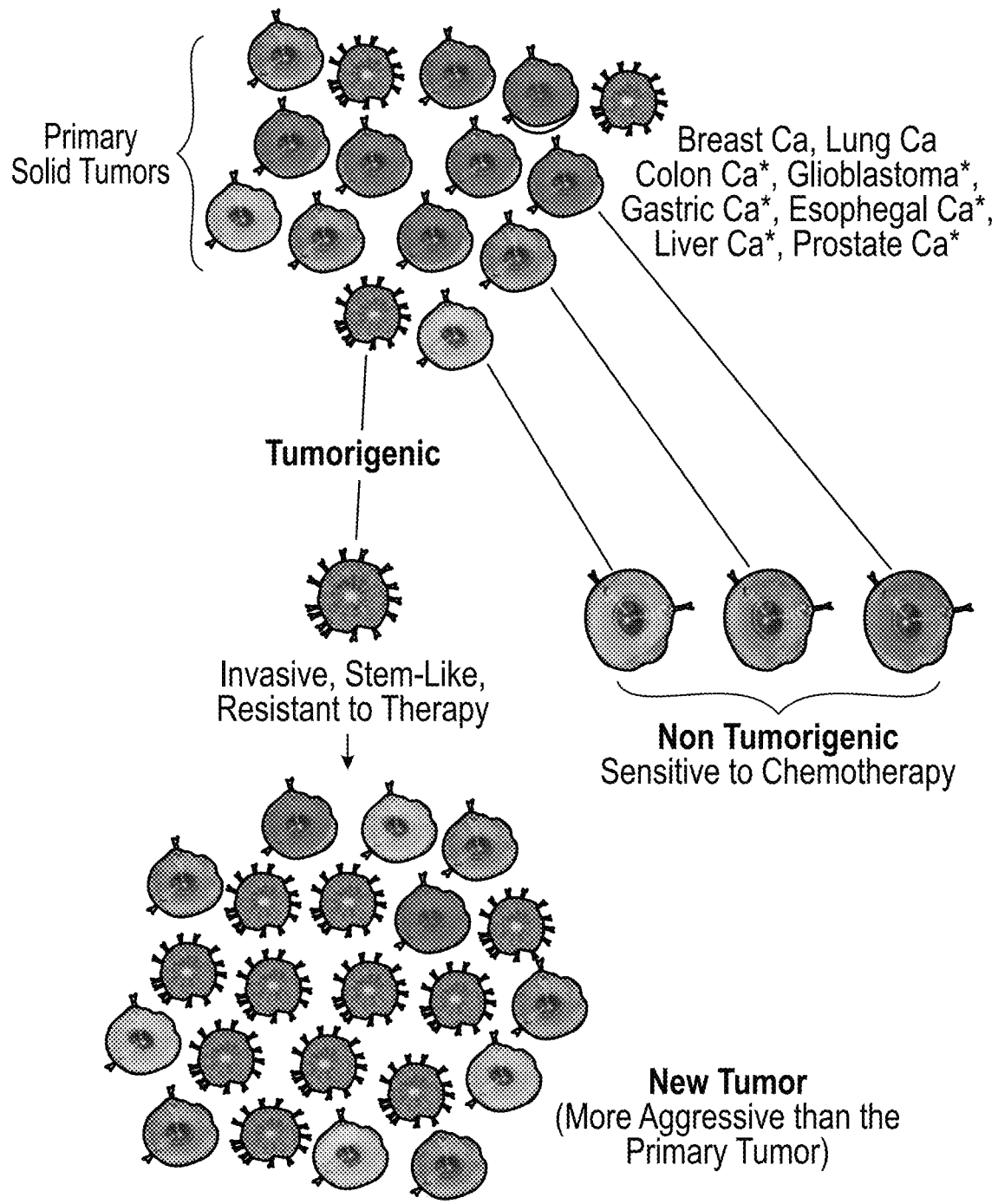
Figure 4H:
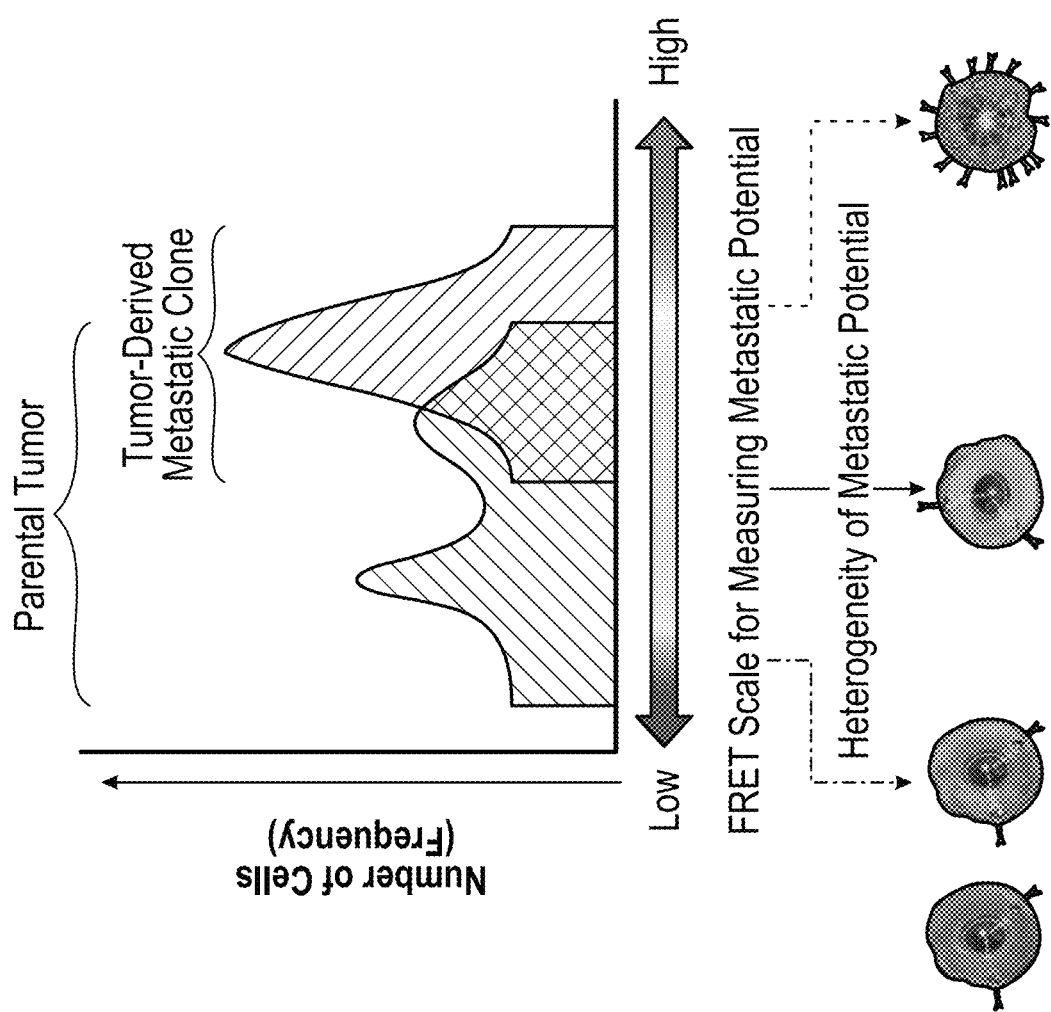
Figure 4H:
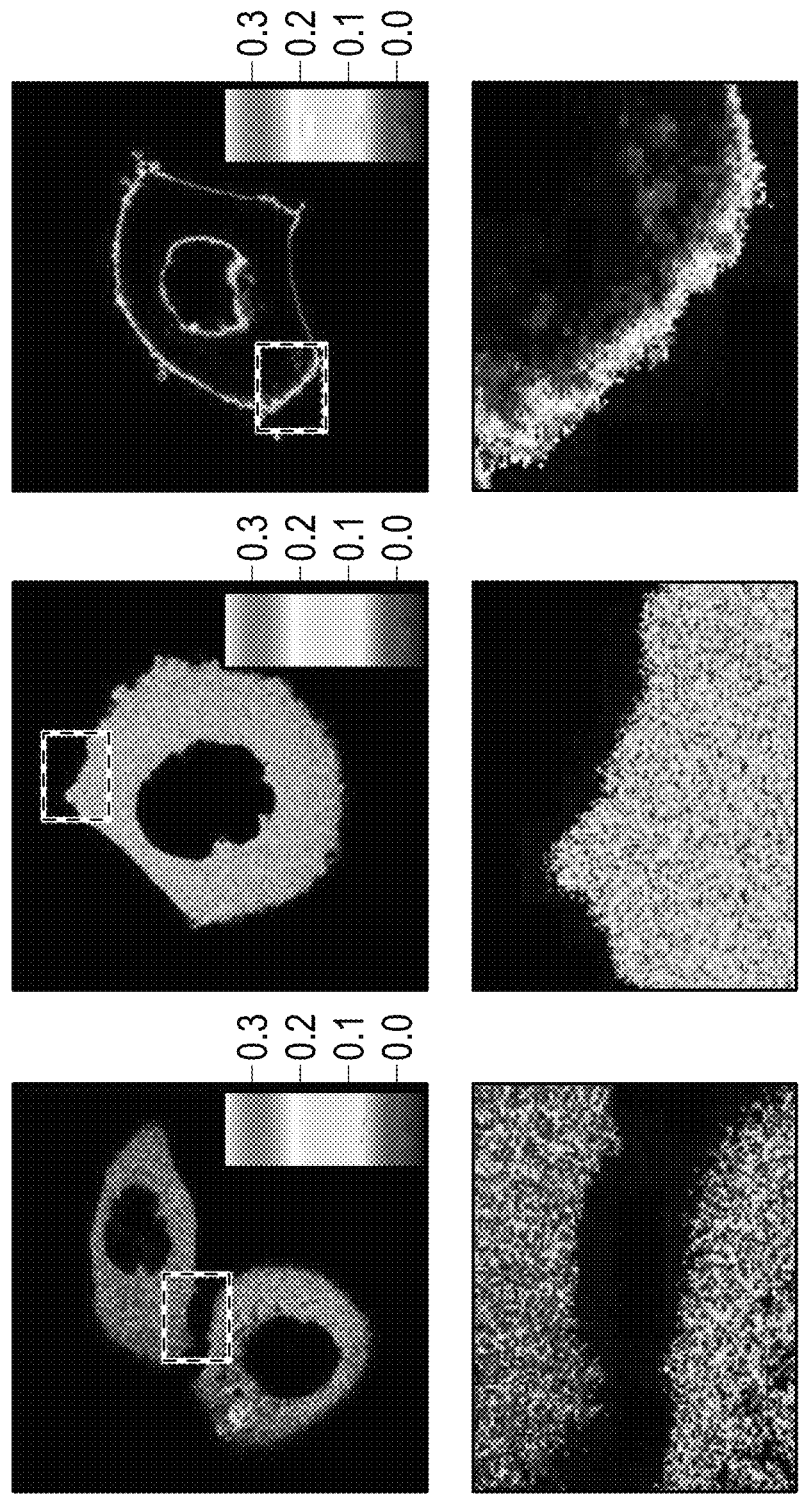

In conclusion, IMP-Y1764 features three properties that make it ideal for molecular imaging; 1) a unique target, i.e., GIV, whose functional phosphorylation broadly reflects the intensity of convergent signaling from multiple upstream pathways via the prometastatic PI3K-Akt pathway; 2) usefulness in a FRET-based approach that retains single-cell information; and 3) ability to fulfill an urgent and unmet need, i.e., measure metastatic potential in a sensitive, specific, objective and unbiased way by overcoming the limitations of the unknown (FIGS. 4G-4H). That IMP-Y1764 detected the 'high' potential for metastasis of 21T-NT-ci cells at diagnosis and 1 y before metastasis to the lungs/pleura (50) indicates that F.E readouts using the IMP-Y1764 probe and the cutoff of 0.14 can be used for ex vivo or in vitro in assays investigating personalized cancer therapeutics response, such that the sensitivity of any tumor to any small-molecule can be studied specifically against those cells with the highest metastatic proclivity in any given tumor.

Methods and Materials

Reagents and Antibodies: All reagents used in this study are of research grade and obtained from Sigma-Aldrich (St. Louis, MO) unless otherwise specified. Cell culture media were purchased from Invitrogen (Carlsbad, CA). EGF (Invitrogen), Insulin (Novagen), Lysophosphatidic Acid (LPA) (Sigma) and PDGF (Invitrogen) were obtained commercially. The Src inhibitor PP2 was obtained from Calbiochem. Receptor Tyrosine Kinase inhibitors Erlotinib (ChemieTek, Indianapolis, IN. Cat #CT-EL002) and Lapatinib (LC laboratories. Cat #L-4899) drugs were generously donated by Frank Furnari (Ludwig Cancer Institute—UCSD). Docetaxel was commercially obtained from Sigma Aldrich (cat #01885). Mouse monoclonal antibodies against pTyr (BD Biosciences, cat #610000), GFP (Santa Cruz Biotechnology), HA (Covance), total (t)ERK (Cell Signaling) and tubulin (Sigma) were purchased from commercial sources. Rabbit polyclonal antibodies against GIV-CT (Girdin T-13, Santa Cruz Biotechnology), phospho-Akt S473 (Cell Signaling), and phospho-ERK 1/2 (Cell Signaling) were obtained commercially. Rabbit monoclonal antibodies against pY1068 EGFR and total (t)Akt were obtained from Cell Signaling and anti-pY1764 GIV antibodies were obtained from Spring Biosciences (1). Anti-mouse and anti-rabbit Alexa-594- and Alexa-488-coupled goat secondary antibodies were used for immunofluorescence. Goat anti-rabbit and goat anti-mouse Alexa Fluor 680 or IRDye 800 F(ab')2 for immunoblotting were from Li—COR Biosciences (Lincoln, NE). Rabbit or mouse IgGs used as negative controls in immunoprecipitation was purchased from Bio-Rad (Hercules, CA) and Sigma (St. Louis, MO), respectively.

Plasmid Constructs: IMP-FRET probes encoding different stretches of GIV's C-terminus encompassing either one or both critical tyrosines, Y1764 and Y1798 of GIV were generated using the cloning strategy previously described for the 'phocus-2nes' FRET probe that was used to measure functional phosphorylation of the adaptor protein IRS-1 (2). Briefly, fragment cDNAs of oligomerization-deficient mutant ECFP (mutations are F64L, S65T, Y66W, N146I, M153T, V163A and N212K), oligomerization-deficient mutant EYFP (mutations are S65G, V68L, Q69K, S72A and T203Y), various stretches of substrate domain from human GIV (Accession #BAE44387; see FIG. 5B), phosphorylation recognition domain [the N-terminal SH2 domain, residues 330-429 from the p85α subunit of bovine PI3K (Accession #NM_174575), which is reported to bind both critical tyrosines within GIV's C-terminus (3)] were generated by standard PCR and cloned into the restriction sites shown in FIG. 1C. A nuclear-export signal sequence (NES)– (4), was inserted to retain the IMP probe in cytosol. Amino acid sequences of flexible linker LnL10 and LnL20 were used, respectively. Various IMP constructs, as illustrated in FIG. 5B, were subcloned between HindIII and XbaI sites of pcDNA 3.1(+) vector (Invitrogen Co., Carlsbad, CA) using Fast Cloning Technique (5). The sequences of primers that were used for cloning IMP constructs are available upon request. GFP-Akt-PH was obtained from R. Tsien (UCSD) and previously used as a reporter to study GIV-dependent activation of PI3K in cells (3). C-terminal HA-tagged c-Src for mammalian expression was generated by cloning the entire coding sequence into pcDNA 3.1 between Xho I and Eco RI. HA tagged SHP-1 was used and validated previously (6). All constructs were checked by DNA sequencing prior to their use in various assays.

Cell Lines: MDA-MB-231, PC-9 and H2030 parental and their brain metastatic (BrM) counterparts listed in FIG. 6B were generous gifts from Joan Massagué (Memorial Sloan Kettering Cancer Center, New York). Briefly, metastatic cells were isolated from either lymph node or pleural effusions of cancer patients and selected in nude mice to generate the BrM subclones, which are known to exhibit higher invasiveness and metastatic proclivity to brain and bone (7, 8). The 21T series (16N, NT and MT2) cancer cell lines isolated from different stages of breast cancer progression were generous gifts from Arthur B. Pardee (Dana-Farber Cancer Institute, Harvard Medical School) and cultured as described earlier (9, 10). Hs578T cells were obtained from ATCC, and their Docetaxel-resistant subclones were generated according to the protocol developed by Andrew C. Schofield et al (11). Briefly, cells were exposed to incremental concentrations of sub-lethal doses of docetaxel on a daily-basis for 1 hr, followed by splitting and recovery until stable revival of growth in media with drug concentration of 30 µM was achieved. Erlotinib and Lapatinib resistant HCC827 were generous gifts from Frank Furnari (Ludwig Cancer Institute—UCSD). Unless mentioned otherwise, cell lines used in this work were cultured according to ATCC guidelines, or guidelines previously published for each line.

Transfection and Cell Lysis: Transfection was carried out using Genejuice (Novagen) or Mirus LT1 (Mirus) for DNA plasmids as previously described (12, 13). Lysates were prepared by resuspending cells in lysis buffer [20 mM HEPES, pH 7.2, 5 mM Mg-acetate, 125 mM K-acetate, 0.4% Triton X-100, 1 mM DTT, supplemented with sodium orthovanadate (500 µM), phosphatase (Sigma) and protease (Roche) inhibitor cocktails], after which they were passed through a 30G needle at 4° C., and cleared (10-14,000 g for 10 min) before being used in subsequent experiments.

In cellulo phosphorylation assays: Cos7 cells expressing the indicated IMP probes in various assays were starved overnight at ~30 h after transfection, and subsequently treated with 0.2 mM $Na_3VO_4$ for 1 h prior to stimulation with growth factors or GPCR ligands. Cells were then washed with chilled PBS at 4° C. that was supplemented with 500 µM $Na_3VO_4$, lysed using ~400 µl of lysis buffer, and equal aliquots of lysates (~1-2 mg of total protein) were incubated for 4 hours at 4° C. with either anti-GFP mouse monoclonal antibody (1 µg) (14) or control mouse IgG. Protein G Sepharose beads (GE Healthcare) were then added to the lysates and incubated at 4° C. for additional 60 min. Beads were then washed 3 times using 1 ml of lysis buffer, and immune complexes were eluted by boiling in Laemmli's sample buffer. For steady state in vivo phosphorylation assays, IMP probes were co-transfected with Src or SHP1 constructs, and after 48 h of transfection cells were lysed and immunoprecipitated with anti-GFP mAb exactly as described for assays using ligand stimulation. In all assays tyrosine phosphorylation of IMP probes was detected by dual color immunoblotting with anti-pTyr mAb (BD Biosciences; Cat #610000) and rabbit polyclonal anti-GFP using LiCOR Odyssey. Presence of yellow pixels on overlay of pTyr (green) and GFP (red) was interpreted as tyrosine phosphorylation of the IMP probe.

Fluorescence Resonance Energy Transfer (FRET) studies: Intramolecular FRET studies were performed as previously reported by Midde et al (15). Briefly, cells were sparsely split into sterile 35 mm MatTek glass bottom dishes. 1 µg of various IMP constructs illustrated in FIG. 5B was transfected with Trans-IT®-LT1 tansfection reagent (Mirus Bio LLC) using manufacturer's protocol. An Olympus FV1000 inverted confocal laser scanning microscope was used for live cell FRET imaging (UCSD-Neuroscience core facility). The microscope is stabilized on a vibration proof platform, caged in temperature controlled (37° C.) and CO2 (5%) supplemented chamber. A 60× 1.49 N.A oil immersed objective designed to minimize chromatic aberration and enhance resolution for 405-605 nm imaging was used. Olympus Fluoview inbuilt software was used for data acquisition through the method of sensitized emission. A 405 nm laser diode was used to excite ECFP and a 515 nm Argon-ion laser was used to excite EYFP. The 405 laser was used because in a recently published work (16) Claire Brown's group has described in great detail why 405 nm excitation is preferred for CFP, when all the controls are performed. Those guidelines have been strictly followed in designing controls in the present study. The bandwidth of spectral emission was adjusted through gating to minimize bleed through. Enhanced CFP emission was collected from 425-500 nm and EYFP emission was collected through 535-600 nm and passed through a 50 nm confocal pinhole before being sent to a photomultiplier tube to reject out of plane focused light. Every field of view is imaged sequentially through ECFPex/ECFPem, ECFPex/EYFPem and EYFPex/EYFPem (3 excitation and emission combinations) and saved as donor, transfer and acceptor image files through an inbuilt wizard. To obtain the FRET images and efficiency of energy transfer values a RiFRET plugin in Image J software was used (17). FRET images were obtained by pixel-by-pixel ratiometric intensity method and efficiency of transfer was calculated by the ratio of intensity in transfer channel to the quenched (corrected) intensity in the donor channel. Cells transfected with CFP and YFP alone were imaged under all three previously mentioned excitation and emission combinations and are used to correct for cross-talk. Furthermore, untransfected cells and a field of view without cells were imaged to correct for background, autofluorescence and light scattering. All fluorescence microscopy assays were performed on single cells in mesoscopic regime to avoid inhomogeneities from samples as shown previously by Midde et al (18, 19). FRET efficiency was quantified from 3-4 Regions of Interests (ROI) per cell drawn exclusively along the P.M.

Statistical Analyses: Data presented is representative of at-least 3 independent experiments and statistical significance was assessed by student t test, where p value<0.05 at 95% was considered statistically significant. Statistical plots, including the Gaussian kernel density plot to the histogram were generated using GRAPHPAD or ORIGINLAB softwares.

REFERENCES

1. S. S. McAllister, R. A. Weinberg, The tumour-induced systemic environment as a critical regulator of cancer progression and metastasis. *Nature cell biology* 16, 717-727 (2014).
2. D. Hanahan, R. A. Weinberg, Hallmarks of cancer: the next generation. *Cell* 144, 646-674 (2011).
3. I. B. Weinstein, Cancer. Addiction to oncogenes—the Achilles heal of cancer. *Science* 297, 63-64 (2002).
4. A. Lorentzen et al., Single cell polarity in liquid phase facilitates tumour metastasis. *Nature communications* 9, 887 (2018).
5. S. I. Kubota et al., Whole-Body Profiling of Cancer Metastasis with Single-Cell Resolution. *Cell Rep* 20, 236-250 (2017).
6. P. Ferronika et al., Copy number alterations assessed at the single-cell level revealed mono- and polyclonal seeding patterns of distant metastasis in a small-cell lung cancer patient. *Ann Oncol* 28, 1668-1670 (2017).
7. D. L. Ellsworth et al., Single-cell sequencing and tumorigenesis: improved understanding of tumor evolution and metastasis. *Clin Transl Med* 6, 15 (2017).
8. H. Kimura et al., Real-time imaging of single cancer-cell dynamics of lung metastasis. *J Cell Biochem* 109, 58-64 (2010).
9. H. Wu et al., Single-cell Transcriptome Analyses Reveal Molecular Signals to Intrinsic and Acquired Paclitaxel Resistance in Esophageal Squamous Cancer Cells. *Cancer Lett* 420, 156-167 (2018).
10. L. Ramapathiran et al., Single-cell imaging of the heat-shock response in colon cancer cells suggests that magnitude and length rather than time of onset determines resistance to apoptosis. *J Cell Sci* 127, 609-619 (2014).
11. W. Chung et al., Single-cell RNA-seq enables comprehensive tumour and immune cell profiling in primary breast cancer. *Nature communications* 8, 15081 (2017).
12. M. C. Lee et al., Single-cell analyses of transcriptional heterogeneity during drug tolerance transition in cancer cells by RNA sequencing. *Proceedings of the National Academy of Sciences of the United States of America* 111, E4726-4735 (2014).
13. Y. Su et al., Single-cell analysis resolves the cell state transition and signaling dynamics associated with melanoma drug-induced resistance. *Proceedings of the National Academy of Sciences of the United States of America* 114, 13679-13684 (2017).
14. P. T. Winnard, Jr. et al., Molecular imaging of metastatic potential. *Journal of nuclear medicine: official publication, Society of Nuclear Medicine* 49 Suppl 2, 96S-112S (2008).
15. J. V. Frangioni, New technologies for human cancer imaging. *Journal of clinical oncology: official journal of the American Society of Clinical Oncology* 26, 4012-4021 (2008).
16. E. Sahai, Illuminating the metastatic process. *Nature reviews. Cancer* 7, 737-749 (2007).
17. S. Veeriah et al., High-throughput time-resolved FRET reveals Akt/PKB activation as a poor prognostic marker in breast cancer. *Cancer research* 74, 4983-4995 (2014).
18. M. Sato, T. Ozawa, K. Inukai, T. Asano, Y. Umezawa, Fluorescent indicators for imaging protein phosphorylation in single living cells. *Nature biotechnology* 20, 287-294 (2002).
19. L. B. Ray, Single-cell biology. Cells go solo. Introduction. *Science* 342, 1187 (2013).
20. R. Zenobi, Single-cell metabolomics: analytical and biological perspectives. *Science* 342, 1243259 (2013).
21. T. Clister, S. Mehta, J. Zhang, Single-cell Analysis of G-protein Signal Transduction. *The Journal of biological chemistry*, (2015).
22. M. R. Philips, Teaching resources. Imaging signal transduction in living cells with fluorescent proteins. *Science's STKE: signal transduction knowledge environment* 2005, tr28 (2005).
23. K. Midde et al., Comparison of orientation and rotational motion of skeletal muscle cross-bridges containing phosphorylated and dephosphorylated myosin regulatory light chain. *The Journal of biological chemistry* 288, 7012-7023 (2013).

24. P. V. Hornbeck et al., PhosphoSitePlus, 2014: mutations, PTMs and recalibrations. *Nucleic Acids Res* 43, D512-520 (2015).

25. P. V. Hornbeck et al., PhosphoSitePlus: a comprehensive resource for investigating the structure and function of experimentally determined post-translational modifications in man and mouse. *Nucleic Acids Res* 40, D261-270 (2012).

26. P. V. Hornbeck, I. Chabra, J. M. Kornhauser, E. Skrzypek, B. Zhang, PhosphoSite: A bioinformatics resource dedicated to physiological protein phosphorylation. *Proteomics* 4, 1551-1561 (2004).

27. H. Mi et al., PANTHER version 11: expanded annotation data from Gene Ontology and Reactome pathways, and data analysis tool enhancements. *Nucleic Acids Res* 45, D183-D189 (2017).

28. E. Eden, R. Navon, I. Steinfeld, D. Lipson, Z. Yakhini, GOrilla: a tool for discovery and visualization of enriched GO terms in ranked gene lists. *BMC Bioinformatics* 10, 48 (2009).

29. F. Supek, M. Bosnjak, N. Skunca, T. Smuc, REVIGO summarizes and visualizes long lists of gene ontology terms. *PLoS One* 6, e21800 (2011).

30. B. Waclaw et al., A spatial model predicts that dispersal and cell turnover limit intratumour heterogeneity. *Nature* 525, 261-264 (2015).

31. N. Aznar, N. Kalogriopoulos, K. K. Midde, P. Ghosh, Heterotrimeric G protein signaling via GIV/Girdin: Breaking the rules of engagement, space, and time. *Bioessays* 38, 379-393 (2016).

32. V. DiGiacomo, A. Marivin, M. Garcia-Marcos, When Heterotrimeric G Proteins Are Not Activated by G Protein-Coupled Receptors: Structural Insights and Evolutionary Conservation. *Biochemistry* 57, 255-257 (2018).

33. P. Ghosh, P. Rangamani, I. Kufareva, The GAPs, GEFs, GDIs and . . . now, GEMs: New kids on the heterotrimeric G protein signaling block. *Cell Cycle* 16, 607-612 (2017).

34. M. Garcia-Marcos, P. Ghosh, M. G. Farquhar, GIV/Girdin transmits signals from multiple receptors by triggering trimeric G protein activation. *The Journal of biological chemistry*, (2015).

35. C. Lin et al., Tyrosine phosphorylation of the Galpha-interacting protein GIV promotes activation of phosphoinositide 3-kinase during cell migration. *Science signaling* 4, ra64 (2011).

36. P. Ghosh, Heterotrimeric G proteins as emerging targets for network based therapy in cancer: End of a long futile campaign striking heads of a Hydra. *Aging (Albany NY)* 7, 469-474 (2015).

37. Y. Mittal, Y. Pavlova, M. Garcia-Marcos, P. Ghosh, Src homology domain 2-containing protein-tyrosine phosphatase-1 (SHP-1) binds and dephosphorylates G(alpha)-interacting, vesicle-associated protein (GIV)/Girdin and attenuates the GIV-phosphatidylinositol 3-kinase (PI3K)-Akt signaling pathway. *The Journal of biological chemistry* 286, 32404-32415 (2011).

38. J. M. Haugh, Live-cell fluorescence microscopy with molecular biosensors: what are we really measuring? *Biophysical journal* 102, 2003-2011 (2012).

39. K. K. Midde et al., Multimodular biosensors reveal a novel platform for activation of G proteins by growth factor receptors. *Proceedings of the National Academy of Sciences*, (2015).

40. C. Lin et al., Structural basis for activation of trimeric Gi proteins by multiple growth factor receptors via GIV/Girdin. *Molecular biology of the cell* 25, 3654-3671 (2014).

41. J. A. Engelman, Targeting PI3K signalling in cancer: opportunities, challenges and limitations. *Nature reviews. Cancer* 9, 550-562 (2009).

42. I. Lopez-Sanchez et al., GIV/Girdin is a central hub for profibrogenic signalling networks during liver fibrosis. *Nature communications* 5, 4451 (2014).

43. M. Garcia-Marcos, P. Ghosh, M. G. Farquhar, GIV is a nonreceptor GEF for G alpha i with a unique motif that regulates Akt signaling. *Proceedings of the National Academy of Sciences of the United States of America* 106, 3178-3183 (2009).

44. P. Jiang et al., An actin-binding protein Girdin regulates the motility of breast cancer cells. *Cancer research* 68, 1310-1318 (2008).

45. D. X. Nguyen et al., WNT/TCF signaling through LEF1 and HOXB9 mediates lung adenocarcinoma metastasis. *Cell* 138, 51-62 (2009).

46. M. Valiente et al., Serpins promote cancer cell survival and vascular co-option in brain metastasis. *Cell* 156, 1002-1016 (2014).

47. D. E. Jenkins, Y. S. Hornig, Y. Oei, J. Dusich, T. Purchio, Bioluminescent human breast cancer cell lines that permit rapid and sensitive in vivo detection of mammary tumors and multiple metastases in immune deficient mice. *Breast cancer research: BCR* 7, R444-454 (2005).

48. P. Ghosh et al., A G{alpha}i-GIV molecular complex binds epidermal growth factor receptor and determines whether cells migrate or proliferate. *Molecular biology of the cell* 21, 2338-2354 (2010).

49. M. Garcia-Marcos et al., Expression of GIV/Girdin, a metastasis-related protein, predicts patient survival in colon cancer. *FASEB journal: official publication of the Federation of American Societies for Experimental Biology* 25, 590-599 (2011).

50. V. Band et al., Tumor progression in four mammary epithelial cell lines derived from the same patient. *Cancer research* 50, 7351-7357 (1990).

51. M. Qiao, J. D. Iglehart, A. B. Pardee, Metastatic potential of 21T human breast cancer cells depends on Akt/protein kinase B activation. *Cancer research* 67, 5293-5299 (2007).

52. A. Singh, J. Settleman, EMT, cancer stem cells and drug resistance: an emerging axis of evil in the war on cancer. *Oncogene* 29, 4741-4751 (2010).

53. K. S. Ullman, M. A. Powers, D. J. Forbes, Nuclear export receptors: from importin to exportin. *Cell* 90, 967-970 (1997).

54. L. H. Souter et al., Human 21T breast epithelial cell lines mimic breast cancer progression in vivo and in vitro and show stage-specific gene expression patterns. *Laboratory investigation; a journal of technical methods and pathology* 90, 1247-1258 (2010).

55. J. C. Wang, J. E. Dick, Cancer stem cells: lessons from leukemia. *Trends Cell Biol* 15, 494-501 (2005).

What is claimed is:

1. A method for detecting metastatic potential and/or chemoresistance in single cells, comprising;
providing within a cell a multi-modular biosensor comprising:
only one stretch of the C-terminus of GIV flanking only one of tyrosines Y1764 and Y1798, wherein the stretch is capable of serving as a target substrate for one or more tyrosine kinases, wherein the stretch of the C-terminus of GIV flanking tyrosine Y1764 or Y1798 consists of 13 amino acids, and wherein the 13 amino acid sequence is selected from the group consisting of RKTEDTYFISSAG (SEQ ID No: 1) and SKDSNPYATLPRA (SEQ ID No: 2),
an N—SH2 domain of p85α (PI3K), and
a fluorescence resonance energy transfer (FRET) pair flanking the one or more stretches of the C-terminus of GIV and the N—SH2 domain of p85α (PI3K), the FRET pair comprising a donor fluorescent protein and an acceptor fluorescent protein; and
detecting FRET signal to measure metastatic potential.

2. The method of claim 1, wherein binding of the N—SH2 domain of p85α (PI3K) to the stretch of the C-terminus of GIV brings the FRET pair in proximity sufficient to generate a FRET signal.

3. The method of claim 1, wherein the N—SH2 domain of p85α (PI3K) binds to the stretch of the C-terminus of GIV after phosphorylation of the tyrosine Y1764 or Y1798.

4. The method of claim 1, wherein the one or more stretches of the C-terminus of GIV and the N—SH2 domain of p85α (PI3K) are separated by a flexible linker.

5. The method of claim 1, wherein the single cells in which metastatic potential and chemoresistance are being detected are cancer cells.

6. The method of claim 1, wherein the single cells in which metastatic potential and chemoresistance are being detected are cells associated with fibrogenesis, diabetes, aging, and/or infertility.

* * * * *

SEQUENCE LISTING

<160> NUMBER OF SEQ ID NOS: 3

<210> SEQ ID NO 1
<211> LENGTH: 13
<212> TYPE: PRT
<213> ORGANISM: Homo sapiens

<400> SEQUENCE: 1

Arg Lys Thr Glu Asp Thr Tyr Phe Ile Ser Ser Ala Gly
1               5                   10

<210> SEQ ID NO 2
<211> LENGTH: 13
<212> TYPE: PRT
<213> ORGANISM: Homo sapiens

<400> SEQUENCE: 2

Ser Lys Asp Ser Asn Pro Tyr Ala Thr Leu Pro Arg Ala
1               5                   10

<210> SEQ ID NO 3
<211> LENGTH: 13
<212> TYPE: PRT
<213> ORGANISM: Homo sapiens

<400> SEQUENCE: 3

Glu Thr Gly Thr Glu Glu Tyr Met Lys Met Asp Leu Gly
1               5                   10